United States Patent
Natchus et al.

(10) Patent No.: US 6,197,770 B1
(45) Date of Patent: Mar. 6, 2001

(54) ALKENYL- AND ALKYNL-CONTAINING METALLOPROTEASE INHIBITORS

(75) Inventors: Michael George Natchus, Glendale; Roger Gunnard Bookland, Cincinnati; Neil Gregory Almstead, Loveland; Stanislaw Pikul, Mason; Biswanath De, Cincinnati; Menyan Cheng, West Chester, all of OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/517,080

(22) Filed: Mar. 1, 2000

Related U.S. Application Data

(60) Provisional application No. 60/122,644, filed on Mar. 3, 1999.

(51) Int. Cl.⁷ .................. A61K 31/5375; A61P 19/02; C07D 295/155
(52) U.S. Cl. ............. 514/238.2; 544/159; 544/383; 544/389; 544/391; 544/394; 544/406; 546/276.4; 546/335; 548/141; 548/163; 548/144; 548/233; 548/492; 548/540; 548/575; 549/444; 562/430; 534/847
(58) Field of Search ............ 544/159; 562/430; 514/238.2

(56) References Cited

U.S. PATENT DOCUMENTS

| | | |
|---|---|---|
| 4,918,105 | 4/1990 | Cartwright et al. |
| 4,954,158 | 9/1990 | Stammer . |
| 4,996,358 | 2/1991 | Handa et al. |
| 5,183,900 | 2/1993 | Galardy et al. |
| 5,189,178 | 2/1993 | Galardy et al. |
| 5,300,674 | 4/1994 | Crimmin et al. |
| 5,310,763 | 5/1994 | Campion et al. |
| 5,442,110 | 8/1995 | Isomura et al. |
| 5,455,258 | 10/1995 | MacPherson et al. |
| 5,506,242 | 4/1996 | MacPherson et al. |
| 5,534,541 | 7/1996 | Drauz et al. |
| 5,552,419 | 9/1996 | MacPherson et al. |
| 5,563,151 | 10/1996 | Bowles et al. |
| 5,753,671 | 5/1998 | Miller et al. |

FOREIGN PATENT DOCUMENTS

| | | |
|---|---|---|
| 4127842 | 2/1993 | (DE) . |
| 0 231 081 | 8/1987 | (EP) . |
| 0 498 665 | 8/1992 | (EP) . |
| 0 575 844 | 12/1993 | (EP) . |
| 0 606 046 | 7/1994 | (EP) . |
| 0 757 984 | 2/1997 | (EP) . |
| 0 769 498 | 4/1997 | (EP) . |
| 0 915 086 | 5/1999 | (EP) . |
| 0 950 656 | 10/1999 | (EP) . |
| 2 268 934 | 1/1994 | (GB) . |
| WO 88/02627 | 4/1988 | (WO) . |
| WO 91/02716 | 3/1991 | (WO) . |
| WO 92/17460 | 10/1992 | (WO) . |
| WO 93/00082 | 1/1993 | (WO) . |
| WO 93/20047 | 10/1993 | (WO) . |
| WO 93/21942 | 11/1993 | (WO) . |
| WO 94/10990 | 5/1994 | (WO) . |
| WO 94/22835 | 10/1994 | (WO) . |
| WO 95/35275 | 12/1995 | (WO) . |
| WO 95/35276 | 12/1995 | (WO) . |
| WO 96/33172 | 10/1996 | (WO) . |
| WO 97/05865 | 2/1997 | (WO) . |
| WO 97/20824 | 6/1997 | (WO) . |
| WO 97/24339 | 7/1997 | (WO) . |
| WO 97/24349 | 7/1997 | (WO) . |
| WO 97/25315 | 7/1997 | (WO) . |
| WO 97/32846 | 9/1997 | (WO) . |
| WO 97/49674 | 12/1997 | (WO) . |
| WO 98/07742 | 2/1998 | (WO) . |
| WO 98/08814 | 3/1998 | (WO) . |
| WO 98/08815 | 3/1998 | (WO) . |
| WO 98/08822 | 3/1998 | (WO) . |
| WO 98/08823 | 3/1998 | (WO) . |
| WO 98/08825 | 3/1998 | (WO) . |
| WO 98/08827 | 3/1998 | (WO) . |

(List continued on next page.)

OTHER PUBLICATIONS

Kahl, J.U. et al., "Synthesis of Two Naturally Occuring Diastereomeric Dihydroxprolines: 2–3–trans–3,4–Dihydroxy–I–proline and 2,3–cis–3,4–trans–3,4–Dihydroxy–I–proline", *Liebigs Ann. Chem.*, 1981, pp. 1445–1450.

(List continued on next page.)

*Primary Examiner*—Robert W. Ramsuer
(74) *Attorney, Agent, or Firm*—Carl J. Roof; Karen F. Clark

(57) ABSTRACT

Disclosed are compounds which are inhibitors of metalloproteases and which are effective in treating conditions characterized by excess activity of these enzymes. In particular, the compounds have a structure according to the following Formula (I):

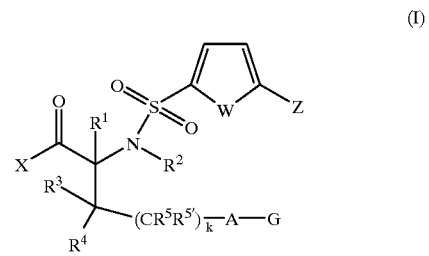

where X, W, Z, A, G, $R^1$, $R^2$, $R^3$, $R^4$, $R^5$, $R^{5'}$ and k have the meanings described in the specification. This invention also includes optical isomers, diastereomers and enantiomers of the formula above, and pharmaceutically-acceptable salts, biohydrolyzable amides, esters, and imides thereof Also described are pharmaceutical compositions comprising these compounds, and methods of treating or preventing metalloprotease-related maladies using the compounds or the pharmaceutical compositions.

45 Claims, No Drawings

FOREIGN PATENT DOCUMENTS

| | | |
|---|---|---|
| WO 98/08850 | 3/1998 | (WO) . |
| WO 98/08853 | 3/1998 | (WO) . |
| WO 98/17645 | 4/1998 | (WO) . |
| WO 98/31664 | 7/1998 | (WO) . |
| WO 98/33768 | 8/1998 | (WO) . |
| WO 98/42659 | 10/1998 | (WO) . |
| WO 98/43963 | 10/1998 | (WO) . |
| WO 99/06340 | 2/1999 | (WO) . |

OTHER PUBLICATIONS

Hudson, C.B. et al., "On the Synthesis of 3,4–Dihydroxprolines I. Cis–Glyolation of 3,4–Dehydroproline Derivatives", *Aust. J. Chem.*, vol. 21, 1968, pp. 769–782.

Andreatta, R.H., "Synthesis of Cis and Trans Isomers of 4–Chloro–$_L$–Proline, 4–Bromo$_L$–Proline and 4–Amino–$_L$–Proline", *Aust. J. Chem.*, vol. 20, 1967, pp. 1493–1509.

Heintzelman, G.R. et al., "Imino Diels–Alder–Based Construction of a Piperidine A–Ring Unit for Total Synthesis of the Marine Hepatotoxin Cylindrospermopsin", *Chemical Abstracts*, vol. 125, No. 5, 1996, Abstract No. 58826.

Edwards, M.L., et al., "Synthesis and Enzymic Resolution of a Carbocyclic Analog of Ribofuranosylamine", *Chemical Abstracts*, vol. 125, No. 1, 1996, Abstract No. 11281.

Herdeis, C., et al., "Amino Acids. XII. (±)–Pipecolic Acid Derivatives. Part 2. An Expedient Synthetic Entry to Substituted Pipecolic Acids", *Chemical Abstracts*, vol. 117, No. 17, 1992, Abstract No. 171989.

Natelson, S. "Preparation of D–, DL–, and L–Homoserine Lactone from Methionine", *Microchemical Journal*, vol. 40, 1989, pp. 226–232.

Hansel, J.G., et al., "Oxazoline Formation via a Palladium–catalyzed Cyclization: A Direct, Stereoselective Approach to cis–5–Amino–2–cyclopenten–1–ol Derivatives", *Tetrahedron Letters*, vol. 36, No. 17, 1995, pp. 2913–2916.

Sarras, M.P., "BMP–1 and the Astacin Family of Metalloproteinases: a Potential Link Between the Extracellular Matrix, Growth Factors, and Pattern Formation", *BioEssays*, vol. 18, No. 6, 1996 (Abstract attached).

Yoneda, N., et al., "Reaction of L–alpha–tosylamido–beta–propiolactone I. Synthesis Reactions with Amines, and Derivation to L–serine", *Yakugaku Zasshi*, vol. 89, No. 1, 1969 (Abstract attached).

Johnson, W.H., et al., "Collagenase Inhibitors: Their Design and Potential Therapeutic Use", *J. Enzyme Inhibition*, vol. 2, 1987, pp. 1–22.

Schwartz, M.A., et al., "8 Synthesis Inhibitors of Bacterial and Mammalian Interstitial Collagenases", *Progress in Medicinal Chemistry*, vol. 29, 1992, pp. 271–334.

Singh, J., et al., "Relationship Between Structure and Bioavailability in a Series of Hydroxamate Based Metalloprotease Inhibitors", *Bioorganic & Medicinal Chemistry Letters*, vol. 5, No. 4, 1995, pp. 337–342.

Tomczuk, B.E., et al., "Hydroxamate Inhibitors of the Matrix Metallo–Proteinases (MMPs) Containing Novel $P_1^1$ Heteroatom Based Modifications", *Bioorganic & Medicinal Chemistry Letters*, vol. 5, No. 4, 1995, pp. 343–348.

Chapman, K.T., et al., "Inhibition of Matrix Metallproteinases by N–Carboxyalkyl Peptides", *J. Med. Chem.*, vol. 36, 1993, pp. 429–43001.

Turbanti, L., et al., "1,2–Cyclomethylenecarboxylic Monoamide Hydroxamic Derivatives. A Novel Class of Non–Amino Acid Angiotensin Converting Enzyme Inhibitors", *J. Med. Chem.*, vol. 36, 1993, pp. 699–707.

Claremon et al, *Chem Abstracts*, vol. 122, No. 291,531, 1995.*

Askew et al, *Chem Abstracts*, vol. 131, No. 58766, 1999.*

Claremon et al, *Chem Abstracts*, vol. 122, No. 31570, 1995.*

* cited by examiner

US 6,197,770 B1

ALKENYL- AND ALKYNL-CONTAINING METALLOPROTEASE INHIBITORS

CROSS REFERENCE TO RELATED APPLICATION

This application claims the benefit of U.S. Provisional Application No. 60/122,644, filed Mar. 3, 1999.

TECHNICAL FIELD

This invention is directed to compounds which are useful in treating diseases associated with metalloprotease activity, particularly zinc metalloprotease activity. The invention is also directed to pharmaceutical compositions comprising the compounds, and to methods of using the compounds or the pharmaceutical compositions.

BACKGROUND

A number of structurally related metalloproteases effect the breakdown of structural proteins. These metalloproteases often act on the intercellular matrix, and thus are involved in tissue breakdown and remodeling. Such proteins are referred to as metalloproteases or MPs.

There are several different families of MPs, classified by sequence homology, disclosed in the art. These MPs include Matrix-Metallo Proteases (MMPs); zinc metalloproteases; many of the membrane bound metalloproteases; TNF converting enzymes; angiotensin-converting enzymes (ACEs); disintegrins, including ADAMs (see Wolfsberg et al, 131 *J. Cell Bio.* 275–78 October, 1995); and the enkephalinases. Examples of MPs include human skin fibroblast collagenase, human skin fibroblast gelatinase, human sputum collagenase, aggrecanse and gelatinase, and human stromelysin. Collagenases, stromelysin, aggrecanase and related enzymes are thought to be important in mediating the symptomatology of a number of diseases.

Potential therapeutic indications of MP inhibitors have been discussed in the literature. See, for example, U.S. Pat. Nos. 5,506,242 (Ciba Geigy Corp.) and 5,403,952 (Merck & Co.); the following PCT published applications: WO 96/06074 (British Bio Tech Ltd.); WO 96/00214 (Ciba Geigy), WO 95/35275 (British Bio Tech Ltd.), WO 95/35276 (British Bio Tech Ltd.), WO 95/33731 (Hoffman-LaRoche), WO 95/33709 (Hoffman-LaRoche), WO 95/32944 (British Bio Tech Ltd.), WO 95/26989 (Merck), WO 9529892 (DuPont Merck), WO 95/24921 (Inst. Opthamology), WO 95/23790 (SmithKline Beecham), WO 95/22966 (Sanofi Winthrop), WO 95/19965 (Glycomed), WO 95 19956 (British Bio Tech Ltd), WO 95/19957 (British Bio Tech Ltd.), WO 95/19961 (British Bio Tech Ltd.), WO 95/13289 (Chiroscience Ltd.), WO 95/12603 (Syntex), WO 95/09633 (Florida State Univ.), WO 95/09620 (Florida State Univ.), WO 95/04033 (Celltech), WO 94/25434 (Celltech), WO 94/25435 (Celltech); WO 93/14112 (Merck), WO 94/0019 (Glaxo), WO 93/21942 (British Bio Tech Ltd.), WO 92/22523 (Res. Corp. Tech Inc.), WO 94/10990 (British Bio Tech Ltd.), WO 93/09090 (Yamanouchi); British patents GB 2282598 (Merck) and GB 2268934 (British Bio Tech Ltd.); published European Patent Applications EP 95/684240 (Hoffman LaRoche), EP 574758 (Hoffman LaRoche) and EP 575844 (Hoffman LaRoche); published Japanese applications JP 08053403 (Fujusowa Pharm. Co. Ltd.) and JP 7304770 (Kanebo Ltd.); and Bird et al., *J. Med. Chem.*, vol. 37, pp. 158–69 (1994).

Examples of potential therapeutic uses of MP inhibitors include rheumatoid arthritis—Mullins, D. E., et al., *Biochim. Biophys. Acta.* (1983) 695:117–214; osteoarthritis—Henderson, B., et al., *Drugs of the Future* (1990) 15:495–508; cancer—Yu, A. E. et al., *Matrix Metalloproteinases—Novel Targets for Directed Cancer Therapy, Drugs & Aging*, Vol. 11(3), p. 229–244 (September 1997), Chambers, A. F. and Matrisian, L. M., *Review: Changing Views of the Role of Matrix Metalloproteinases in Metastasis, J. of the Nat'l Cancer Inst.*, Vol. 89(17), p. 1260–1270 (September 1997), Bramhall, S. R., *The Matrix Metalloproteinases and Their Inhibitors in Pancreatic Cancer, Internat'l J. of Pancreatology,* Vol. 4, p. 1101–1109 (May 1998), Nemunaitis, J. et al., *Combined Analysis of Studies of the Effects of the Matrix Metalloproteinase Inhibitor Marimastat on Serum Tumor Markers in Advanced Cancer: Selection of a Biologically Active and Tolerable Dose for Longer-term Studies, Clin. Cancer Res.,* Vol 4, p. 1101–1109 (May 1998), and Rasmussen, H. S. and McCann, P. P, *Matrix Metalloproteinase Inhibition as a Novei Anticancer Strategy: A Review with Special Focus on Batimastat and Marimastat, Pharmacol. Ther.,* Vol 75(1), p. 69–75 (1997); the metastasis of tumor cells—ibid, Broadhurst, M. J., et al., European Patent Application 276,436 (published 1987), Reich, R., et al., *Cancer Res.* Vol. 48, p. 3307–3312 (1988); multiple sclerosis—Gijbels et al.,*J. Clin. Invest.* vol. 94, p. 2177–2182 (1994); and various ulcerations or ulcerative conditions of tissue. For example, ulcerative conditions can result in the cornea as the result of alkali burns or as a result of infection by *Pseudomonas aeruginosa, Acanthamoeba,* Herpes simplex and vaccinia viruses. Other examples of conditions characterized by undesired metalloprotease activity include periodontal disease, epidermolysis bullosa, fever, inflammation and scleritis (e.g., DeCicco et al., PCT published application WO 95/29892, published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa et al.; U.S. Pat. No. 4,771,038, issued Sep. 13, 1988 to Wolanin et al.; U.S. Pat. No. 4,743,587, issued May 10, 1988 to Dickens et al., European Patent Publication No. 575,844, published Dec. 29, 1993 by Broadhurst et al.; International Patent Publication No. WO 93/09090, published May 13, 1993 by Isomura et al.; World Patent Publication 92/17460, published Oct. 15, 1992 by Markwell et al.; and European Patent Publication No. 498,665, published Aug. 12, 1992 by Beckett et al.

It would be advantageous to inhibit these metalloproteases in treating diseases related to unwanted metalloprotease activity. Though a variety of MP inhibitors have been prepared, there is a continuing need for potent matrix metalloprotease inhibitors useful in treating diseases associated with metalloprotease activity.

SUMMARY OF THE INVENTION

The invention provides compounds which are potent inhibitors of metalloproteases and which are effective in treating conditions characterized by excess activity of these enzymes. In particular, the present invention relates to compounds having a structure according to the following Formula (I):

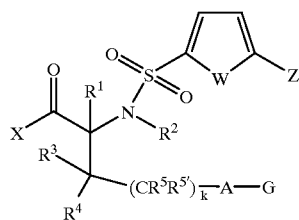

(I)

wherein (A) X is selected from —OH and —NHOH;

(B) W is selected from —S—, —O—, —N($R^{33}$)—, —C($R^{33}$)=C($R^{33'}$)—, —N=C($R^{33}$)—, and —N=N—, where $R^{33}$ and $R^{33'}$ each is independently selected from hydrogen, alkyl, alkenyl, alkynyl, heteroalkyl, aryl, heteroaryl, cycloalkyl, and heterocycloalkyl;

(C) $R^1$ is —($CR^6R^{6'}$)$_l$—$R^{34}$ where l is from 0 to about 4; each $R^6$ and $R^{6'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{34}$ is selected from hydrogen, hydroxyl, alkoxy, alkyl, alkenyl, alkynyl, heteroalkyl, haloalkyl, cycloalkyl, heterocycloalkyl, aryl, heteroaryl, and halogen;

(D) $R^2$ is —($CR^7R^{7'}$)$_m$—$R^{35}$ where m is from 0 to about 4; each $R^7$ and $R^{7'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{35}$ is selected from hydrogen, alkyl, alkenyl, alkynyl, heteroalkyl, haloalkyl, aryl, heteroaryl, cycloalkyl, and heterocycloalkyl;

(E) $R^3$ is —($CR^8R^{8'}$)$_n$—$R^9$ where n is from 0 to about 4; each $R^8$ and $R^{8'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^9$ is selected from hydrogen, hydroxyl, alkoxy, alkyl, alkenyl, alkynyl, aryloxy, heteroalkyl, heteroaryloxy, haloalkyl, cycloalkyl, heterocycloalkyl, aryl, heteroaryl, and halogen;

(F) $R^4$ is —($CR^{10}R^{10'}$)$_z$—A'—($CR^{10''}R^{10'''}$)$_o$—$R^{11}$ where A' is selected from a covalent bond, —O—, —S— and $SO_2$; z is from 0 to about 4; o is from 0 to about 4; each $R^{10}$, $R^{10'}$, $R^{10''}$ and $R^{10'''}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{11}$ is selected from hydrogen, alkyl, alkenyl, alkynyl, heteroalkyl, haloalkyl, cycloalkyl, heterocycloalkyl, aryl, heteroaryl, and halogen;

(G) each $R^5$ and $R^{5'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and k is from 0 to about 4;

(H) A is selected from

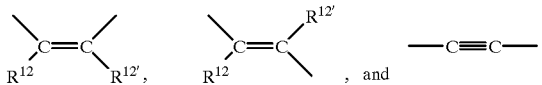

where $R^{12}$ and $R^{12'}$ each is independently selected from hydrogen, alkyl, alkenyl, alkynyl, haloalkyl, aryl, heteroalkyl, heteroaryl, heterocycloalkyl, cycloalkyl, halogen, and —$CONR^{13}R^{13+}$ where (1) $R^{13}$ and $R^{13'}$ each is independently selected from hydrogen, alkyl, alkenyl, alkynyl, heteroalkyl, aryl, and heteroaryl, or (2) $R^{13}$ and $R^{13'}$, together with the nitrogen atom to which they are bonded, join to form an optionally substituted heterocyclic ring containing from 5 to 8 ring atoms of which from 1 to 3 are heteroatoms;

(I) G is selected from (1) hydrogen;

(2) —($CR^{14}R^{14'}$)$_p$—$R^{15}$ where p is from 0 to about 4; each $R^{14}$ and $R^{14'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{15}$ is selected from hydrogen, alkyl, aryl, heteroaryl, cycloalkyl, heterocycloalkyl, arylalkyl, and heteroarylalkyl;

(3) —($CR^{16}R^{16'}$)$_q$—Y—($CR^{17}R^{17'}$)$_r$—$R^{18}$ where q is from 1 to about 4 and r is from 0 to about 4; each $R^{16}$, $R^{16'}$, $R^{17}$, and $R^{17'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; Y is selected from —O— and —S—; and $R^{18}$ is selected from hydrogen, hydroxyl, alkoxy, alkyl, heteroalkyl, haloalkyl, cycloalkyl, heterocycloalkyl, aryl, and heteroaryl; provided that when r=0, $R^{18}$ is not hydroxyl or alkoxy;

(4) —$CONR^{37}R^{37'}$ where (a) $R^{37}$ and $R^{37'}$ each is independently selected from hydrogen, alkyl, alkenyl, alkynyl, heteroalkyl, haloalkyl, aryl, heteroaryl, cycloalkyl, and heterocycloalkyl; or (b) $R^{37}$ and $R^{37'}$, together with the nitrogen atom to which they are bonded, join to form an optionally substituted heterocyclic ring containing from 5 to 8 ring atoms of which from 1 to 3 are heteroatoms; and (5) —($CR^{19}R^{19'}$)$_s$—$NR^{20}R^{20'}$ where s is from 1 to about 4; each $R^{19}$ and $R^{19'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{20}$ and $R^{20'}$ each is independently selected from:

(a) hydrogen, alkyl, alkenyl, alkynyl, heteroalkyl, haloalkyl, aryl, heteroaryl, cycloalkyl, and heterocycloalkyl;

(b) —C(O)$R^{21}$ where $R^{21}$ is selected from hydrogen, alkyl, alkenyl, alkynyl, heteroalkyl, haloalkyl, aryl, heteroaryl, cycloalkyl, and heterocycloalkyl; or $R^{21}$ and $R^{20}$, together with the amide group to which they are bonded, may join to form an optionally substituted heterocyclic ring containing from 5 to 8 ring atoms of which from 1 to 3 are heteroatoms;

(c) —$SO_2$—($CR^{22}R^{22'}$)$_t$—$R^{23}$ where t is from 0 to about 4; each $R^{22}$ and $R^{22'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{23}$ is selected from alkyl, heteroalkyl, haloalkyl, aryl, heteroaryl, cycloalkyl, and heterocycloalkyl; or $R^{23}$ and $R^{20}$, together with the sulfonamide group to which they are bonded, join to form an optionally substituted heterocyclic ring containing from 5 to 8 ring atoms of which from 1 to 3 are heteroatoms;

(d) —C(O)$NR^{24}R^{24'}$ where (i) $R^{24}$ and $R^{24'}$ are independently selected from hydrogen, alkyl, alkenyl, alkynyl, haloalkyl, heteroalkyl, aryl, heteroaryl, cycloalkyl, and heterocycloalkyl; or (ii) $R^{24}$ and $R^{24'}$, together with the nitrogen atom to which they are bonded, join to form an optionally substituted heterocyclic ring containing from 5 to 8 ring atoms of which from 1 to 3 are heteroatoms; and (e) —C(O)OR$^{25}$ where R$^{25}$ is selected from alkyl, alkenyl, alkynyl, heteroalkyl, haloalkyl, aryl, heteroaryl, cycloalkyl, and heterocycloalkyl; or (f) R$^{20}$ and R$^{20'}$, together with the nitrogen atom to which they are bonded, join to form an optionally substituted heterocyclic ring containing from 5 to 8 ring atoms of which from 1 to 3 are heteroatoms; and (J) Z is selected from (1) cycloalkyl and heterocycloalkyl;

(2) —D—(CR$^{26}$R$^{26'}$)$_u$R$^{27}$ where (a) u is from 0 to about 4;

(b) D is selected from —C≡C—, —CH═CH—, —N═N—, —O—, —S— and —SO$_2$—;

(c) each R$^{26}$ and R$^{26'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and (d) R$^{27}$ is selected from aryl, heteroaryl, alkyl, alkenyl, alkynyl, heteroalkyl, haloalkyl, heterocycloalkyl, cycloalkyl and, if D is —C≡C— or —CH═CH—, then R$^{27}$ may also be selected from CONR$^{28}$R$^{28'}$ where (i) R$^{28}$ and R$^{28'}$ are independently selected from hydrogen, alkyl, alkenyl, alkynyl, haloalkyl, heteroalkyl, aryl, heteroaryl, cycloalkyl, and heterocycloalkyl, or (ii) R$^{28}$ and R$^{28'}$, together with the nitrogen atom to which they are bonded, join to form an optionally substituted heterocyclic ring containing from 5 to 8 ring atoms of which from 1 to 3 are heteroatoms;

(3) —NR$^{29}$R$^{29'}$ where (a) R$^{29}$ and R$^{29'}$ each is independently selected from hydrogen; alkyl; alkenyl; alkynyl; heteroalkyl; haloalkyl; aryl; heteroaryl; cycloalkyl; heteroalkyl; and C(O)—Q—(CR$^{30}$R$^{30'}$)$_v$R$^{31}$, where v is from 0 to about 4, Q is selected from a covalent bond and —NR$^{32}$—, each R$^{30}$ and R$^{30'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; R$^{31}$ and R$^{32}$ (i) each is independently selected from hydrogen, alkyl, alkenyl, alkynyl, heteroalkyl, haloalkyl, aryl, heteroaryl, cycloalkyl, and heterocycloalkyl, or (ii) R$^{31}$ and R$^{32}$, together with the nitrogen atoms to which they are bonded, join to form an optionally substituted heterocyclic ring containing from 5 to 8 ring atoms of which from 1 to 3 are heteroatoms; or R$^{29}$ and R$^{32}$, together with the nitrogen atoms to which they are bonded, join to form an optionally substituted heterocyclic ring containing from 5 to 8 ring atoms of which from 1 to 3 are heteroatoms; or (b) R$^{29}$ and R$^{29'}$, together with the nitrogen atom to which they are bonded, join to form an optionally substituted heterocyclic ring containing from 5 to 8 ring atoms of which from 1 to 3 are heteroatoms; and (4)

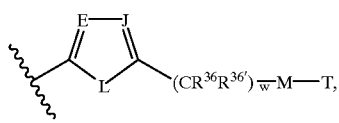

where (a) E and J are independently selected from —CH— and —N—;

(b) L is selected from —S—, —O—, —N(R$^{38}$)—, —C(R$^{38}$)═C(R$^{38'}$)—, N═C(R$^{38}$)—, and —N═N—, where R$^{38}$ and R$^{38'}$ each is independently selected from hydrogen, alkyl, alkenyl, alkynyl, heteroalkyl, aryl, heteroaryl, cycloalkyl, and heterocycloalkyl;

(c) w is from 0 to about 4;

(d) each R$^{36}$ and R$^{36'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;

(e) M is selected from covalent bond, —O—, —SO$_x$—, —C(O)—, —C(O)NR$^{39}$—, —NR$^{39}$—, and —NR$^{39}$C(O)—; where x is from 0 to 2; and R$^{39}$ is selected from hydrogen, alkyl, alkenyl, alkynyl, aryl, heteroaryl, heteroalkyl, heteroaryl, cycloalkyl, heterocycloalkyl, and haloalkyl; and (f) T is —(CR$^{40}$R$^{40'}$)$_y$R$^{41}$ where y is from 0 to about 4; each R$^{40}$ and R$^{40'}$ is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy; and R$^{41}$ is selected from hydrogen, alkyl, alkenyl, alkynyl, halogen, heteroalkyl, haloalkyl, aryl, heteroaryl, cycloalkyl, heterocycloalkyl; or R$^{39}$ and R$^{41}$, together with the atoms to which they are bonded, join to form an optionally substituted heterocyclic ring containing from 5 to 8 atoms of which 1 to 3 are heteroatoms; or R$^{38}$ and R$^{41}$, together with the atoms to which they are bonded, join to form an optionally substituted heterocyclic ring containing from 5 to 8 atoms of which 1 to 3 are heteroatoms; or an optical isomer, diastereomer or enantiomer for Formula (I), or a pharmaceutically-acceptable salt, or biohydrolyzable amide, ester, or imide thereof.

This invention also includes optical isomers, diastereomers and enantiomers of the formula above, and pharmaceutically-acceptable salts, biohydrolyzable amides, esters, and imides thereof.

The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies.

DETAILED DESCRIPTION OF THE INVENTION

I. Terms and Definitions

The following is a list of definitions for terms used herein:
The following is a list of definitions for terms used herein.

"Acyl" or "carbonyl" is a radical formed by removal of the hydroxy from a carboxylic acid (i.e., R—C(═O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkyne" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$—$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems-wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

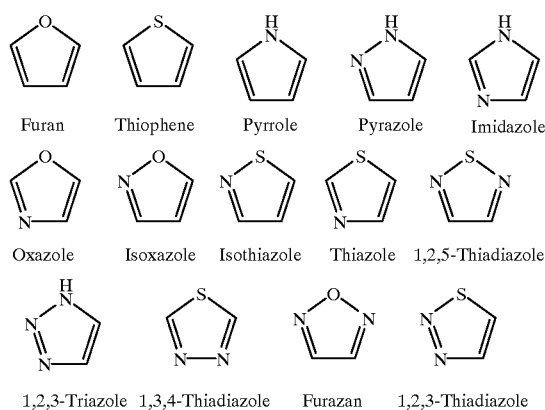

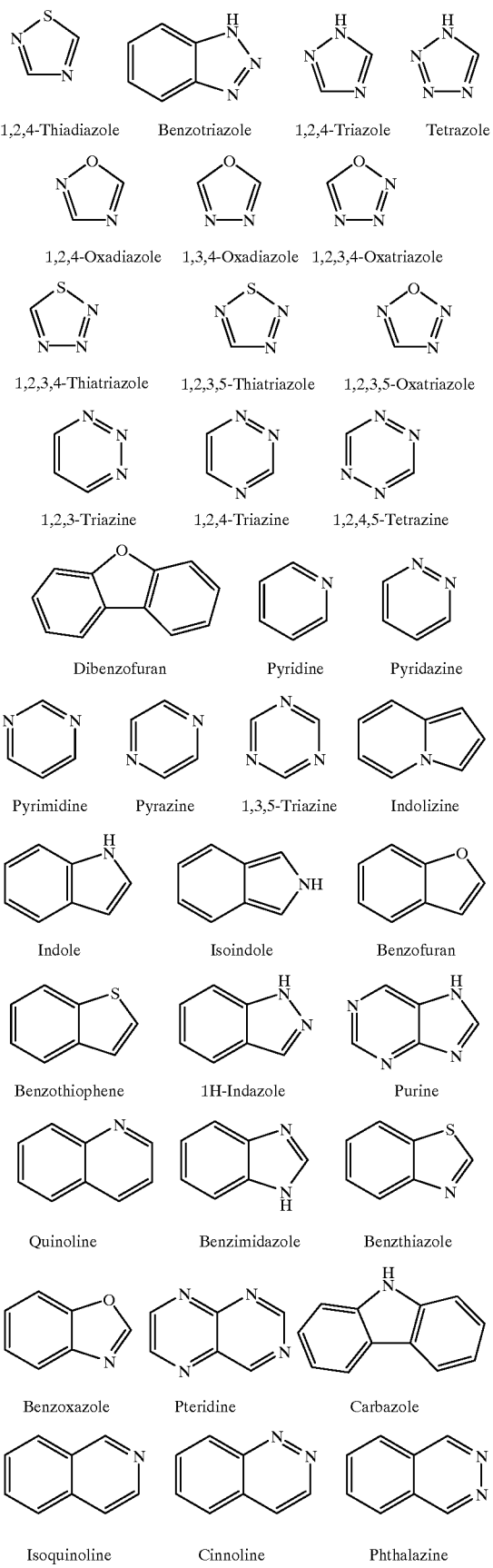
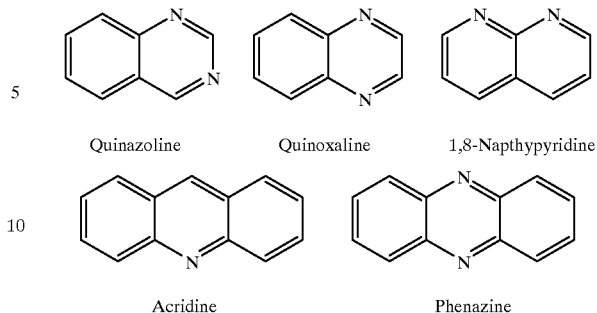

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof Preferred substituents on heterocycloalkyl include halo and haloalkyl. Preferred heterocycloalkyl rings include, but are not limited to, the following:

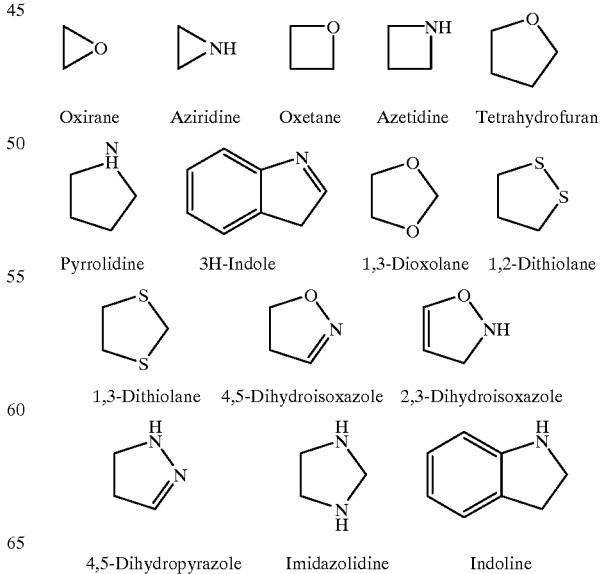

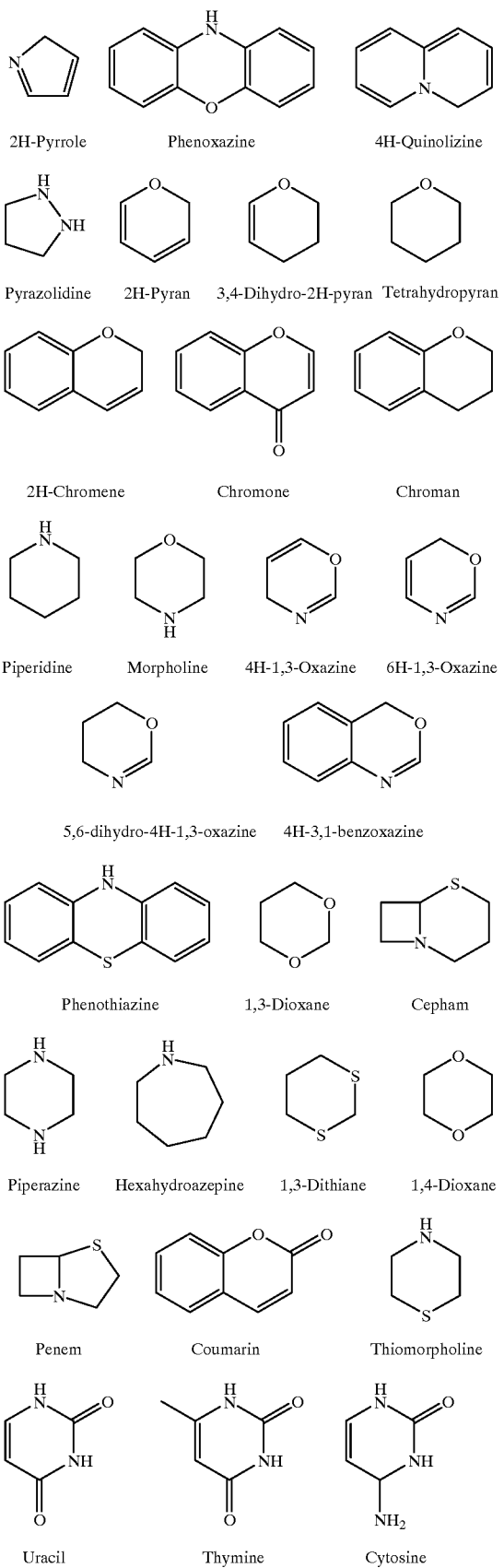
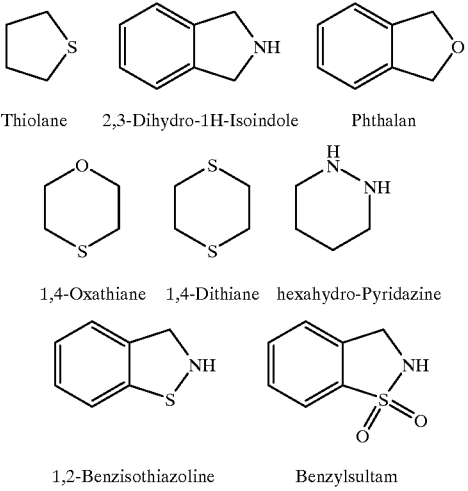

As used herein, "mammalian metalloprotease" refers to the proteases disclosed in the "Background" section of this application. The compounds of the present invention are preferably active against "mammalian metalloproteases", including any metal-containing (preferably zinc-containing) enzyme found in animal, preferably mammalian, sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345; use of a synthetic substrate is described by Weingarten, H., et al., *Biochem. Biophy. Res. Comm.* (1984) 139:1184–1187. See also Knight, C. G. et al., "A Novel Coumarin-Labelled Peptide for Sensitive Continuous Assays of the Matrix Metalloproteases", *FEBS Letters*, Vol. 296, pp. 263–266 (1992). Any standard method for analyzing the breakdown of these structural proteins can, of course, be used. The present compounds are more preferably active against metalloprotease enzymes that are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).

4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide of a hydroxamic acid-containing (i.e., $R^1$ is in Formula (I) is —NHOH) metalloprotease inhibitor that does not interfere with the inhibitory activity of the compound, or that is readily converted in vivo by an animal, preferably a mammal, more preferably a human subject, to yield an active metalloprotease inhibitor. Examples of such amide derivatives are alkoxyamides, where the hydroxyl hydrogen of the hydroxamic acid of Formula (I) is replaced by an alkyl moiety, and acyloxyamides, where the hydroxyl hydrogen is replaced by an acyl moiety (i.e., R—C(=O)—).

A "biohydrolyzable hydroxy imide" is an imide of a hydroxamic acid-containing metalloprotease inhibitor that does not interfere with the metalloprotease inhibitory activity of these compounds, or that is readily converted in vivo by an animal, preferably a mammal, more preferably a human subject to yield an active metalloprotease inhibitor. Examples of such imide derivatives are those where the amino hydrogen of the hydroxamic acid of Formula (I) is replaced by an acyl moiety (i.e., R—C(=O)—).

A "biohydrolyzable ester" is an ester of a carboxylic acid-containing (i.e., $R^1$ in Formula (I) is —OH) metalloprotease inhibitor that does not interfere with the metalloprotease inhibitory activity of these compounds or that is readily converted by an animal to yield an active metalloprotease inhibitor. Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

II. Compounds

The subject invention involves compounds of Formula (I):

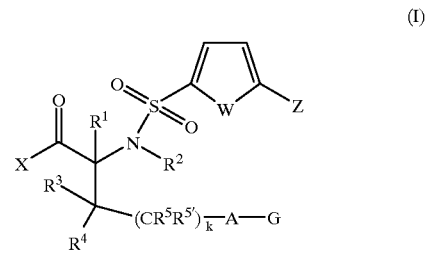

where X, W, Z, A, G, $R^1$, $R^2$, $R^3$, $R^4$, $R^5$, $R^{5'}$ and k have the meanings described above. The following provides a description of particularly preferred moieties, but is not intended to limit the scope of the claims.

X is selected from —OH and —NHOH.

W is selected from —S— —O—, —N($R^{33}$)—, —C($R^{33}$)=C($R^{33'}$)—, —N=C($R^{33}$)—, and —N=N—; in a preferred embodiment, W is —S— or —C($R^{33}$)=C($R^{33'}$)—. Each $R^{33}$ and $R^{33'}$ is independently selected from hydrogen, alkyl, alkenyl, alkynyl, heteroalkyl, aryl, heteroaryl, cycloalkyl, and heterocycloalkyl; preferably at least one of $R^{33}$ and $R^{33'}$ is hydrogen, more preferably both are hydrogen.

$R^1$ is —(CR$^6$R$^{6'}$)$_l$—R$^{34}$. l is from 0 to about 4, preferably 0 or 1, and more preferably 0. Each $R^6$ and $R^{6'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably at least one of each $R^6$ or $R^{6'}$ is hydrogen, more preferably each $R^6$ and $R^{6'}$ is hydrogen. $R^{34}$ is selected from hydrogen, hydroxyl, alkoxy, alkyl, alkenyl, alkynyl, heteroalkyl, haloalkyl, cycloalkyl, heterocycloalkyl, aryl, heteroaryl, and halogen; $R^{34}$ is preferably hydrogen, alkyl, aryl, heteroaryl, or heterocycloalkyl, and more preferably is hydrogen.

$R^2$ is —(CR$^7$R$^{7'}$)$_m$—R$^{35}$. m is from 0 to about 4, preferably m is 0. Each $R^7$ and $R^{7'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably at least one of each $R^7$ or $R^{7'}$ is hydrogen, more preferably each $R^7$ and $R^{7'}$ is hydrogen. $R^{35}$ is selected from hydrogen, alkyl, alkenyl, alkynyl, heteroalkyl, haloalkyl, aryl, heteroaryl, cycloalkyl, and heterocycloalkyl; $R^{35}$ is preferably hydrogen or alkyl, more preferably hydrogen.

$R^3$ is —(CR$^8$R$^{8'}$)$_n$—R$^9$. n is from 0 to about 4, preferably n is 0 or 1. Each $R^8$ and $R^{8'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably at least one of each $R^8$ or $R^{8'}$ is hydrogen, more preferably each $R^8$ and $R^{8'}$ is hydrogen. $R^9$ is selected from hydrogen, hydroxyl, alkoxy, alkyl, alkenyl, alkynyl, aryloxy, heteroalkyl, heteroaryloxy, haloalkyl, cycloalkyl, heterocycloalkyl, aryl, heteroaryl, and halogen; $R^9$ is preferably hydrogen, hydroxyl, alkoxy, alkyl, aryloxy, or aryl.

$R^4$ is —$(CR^{10}R^{10'})_z$—A'—$(CR^{10"}R^{10'''})_o$—$R^{11}$. z is from 0 to about 4. A' is selected from a covalent bond, —O—, —S— and $SO_2$; o is from 0 to about 4 and preferably is 0. Each $R^{10}$, $R^{10'}$, $R^{10"}$ and $R^{10'''}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy. $R^{11}$ is selected from hydrogen, alkyl, alkenyl, alkynyl, heteroalkyl, haloalkyl, cycloalkyl, heterocycloalkyl, aryl, heteroaryl, and halogen; $R^{11}$ is preferably hydrogen or lower alkyl.

Each $R^5$ and $R^{5'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably at least one of each $R^5$ or $R^{5'}$ is hydrogen, more preferably each $R^5$ and $R^{5'}$ is hydrogen.

k is from 0 to about 4; k is preferably 0 or 1, more preferably 0.

A is selected from a cis double bond containing moiety, a trans double bond containing moiety, or a triple bond containing moiety, as follows:

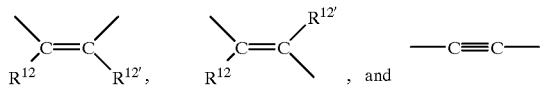

$R^{12}$ and $R^{12'}$ each is independently selected from hydrogen, alkyl, alkenyl, alkynyl, haloalkyl, aryl, heteroalkyl, heteroaryl, heterocycloalkyl, cycloalkyl, halogen, and —$CONR^{13}R^{13'}$; preferred is where $R^{12}$ and $R^{12'}$ each are hydrogen or lower alkyl. $R^{13}$ and $R^{13'}$ each is independently selected from hydrogen, alkyl, alkenyl, alkynyl, heteroalkyl, aryl, and heteroaryl; preferably hydrogen, lower alkyl or aryl. Alternatively, $R^{13}$ and $R^{13'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms.

G is selected from hydrogen; —$(CR^{14}R^{14'})_p$—$R^{15}$; —$(CR^{16}R^{16'})_q$—Y—$(CR^{17}R^{17'})_r$—$R^{18}$; —$CONR^{37}R^{37'}$; and —$(CR^{19}R^{19'})_s$—$NR^{20}R^{20'}$.

When G is —$(CR^{14}R^{14'})_p$—$R^{15}$, p is from 0 to about 4, preferably 0 to 2. Each $R^{14}$ and $R^{14'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{14}$ is hydrogen and each $R^{14'}$ is independently hydrogen or lower alkyl. $R^{15}$ is selected from hydrogen, alkyl, aryl, heteroaryl, cycloalkyl, heterocycloalkyl, arylalkyl, and heteroarylalkyl, preferably alkyl, aryl, heteroaryl, cycloalkyl, heterocycloalkyl, arylalkyl, and heteroarylalkyl.

When G is —$(CR^{16}R^{16'})_q$—Y—$(CR^{17}R^{17'})_r$—$R^{18}$, q is from 1 to about 4, preferably 1 to 2 more preferably 1. r is from 0 to about 4, preferably 0 or 1. Each $R^{16}$, $R^{16'}$, $R^{17}$, and $R^{17'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{16}$, $R^{16'}$, $R^{17}$, and $R^{17'}$ is hydrogen or lower alkyl. Y is selected from —O— and —S—. $R^{18}$ is selected from hydrogen, hydroxyl, alkoxy, alkyl, heteroalkyl, haloalkyl, cycloalkyl, heterocycloalkyl, aryl, and heteroaryl; provided that when r=0, $R^{18}$ is not hydroxyl or alkoxy.

When G is —$CONR^{37}R^{37'}$, $R^{37}$ and $R^{37'}$ each is independently selected from hydrogen, alkyl, alkenyl, alkynyl, heteroalkyl, haloalkyl, aryl, heteroaryl, cycloalkyl, and heterocycloalkyl; preferably hydrogen, alkyl, heteroalkyl, aryl or heteroaryl. Alternatively, $R^{37}$ and $R^{37'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms. In a particularly preferred embodiment, $R^{37}$ and $R^{37'}$ join to form a ring.

When G is —$(CR^{19}R^{19'})_s$—$NR^{20}R^{20'}$ s is from 1 to about 4, preferably s 1 or 2. Each $R^{19}$ and $R^{19'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{19}$ is hydrogen and each $R^{19'}$ is independently hydrogen or lower alkyl. $R^{20}$ and $R^{20'}$ each is independently selected from:

(a) hydrogen, alkyl, alkenyl, alkynyl, heteroalkyl, haloalkyl, aryl, heteroaryl, cycloalkyl, and heterocycloalkyl; preferably alkyl or aryl;

(b) —$C(O)R^{21}$ where $R^{21}$ is selected from hydrogen, alkyl, alkenyl, alkynyl, heteroalkyl, haloalkyl, aryl, heteroaryl, cycloalkyl, and heterocycloalkyl; preferably lower alkyl, aryl or heteroaryl. Alternatively, $R^{21}$ and $R^{20}$, together with the amide group to which they are bonded, may join to form an optionally substituted heterocyclic ring containing from 5 to 8 (preferably 5 or 6) ring atoms of which from 1 to 3 (preferably 1 or 2) are heteroatoms;

(c) —$SO_2$—$(CR^{22}R^{22'})_t$—$R^{23}$ where t is from 0 to about 4, preferably 0. Each $R^{22}$ and $R^{22'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably hydrogen or lower alkyl. $R^{23}$ is selected from alkyl, heteroalkyl, haloalkyl, aryl, heteroaryl, cycloalkyl, and heterocycloalkyl; preferably $R^{23}$ is lower alkyl, aryl, or heteroaryl. Alternatively, $R^{23}$ and $R^{20}$, together with the sulfonamide group to which they are bonded, join to form an optionally substituted heterocyclic ring containing from 5 to 8 (preferably 5 or 6) ring atoms of which from 1 to 3 (preferably 1 or 2) are heteroatoms;

(d) —$C(O)NR^{24}R^{24'}$ where $R^{24}$ and $R^{24'}$ are independently selected from hydrogen, alkyl, alkenyl, alkynyl, haloalkyl, heteroalkyl, aryl, heteroaryl, cycloalkyl, and heterocycloalkyl; preferably hydrogen or lower alkyl. Alternatively, $R^{24}$ and $R^{24'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms; and (e) —$C(O)OR^{25}$ where $R^{25}$ is selected from alkyl, alkenyl, alkynyl, heteroalkyl, haloalkyl, aryl, heteroaryl, cycloalkyl, and heterocycloalkyl; preferably alkyl, aryl or heteroaryl.

Alternatively $R^{20}$ and $R^{20'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms.

Z is selected from cycloalkyl and heterocycloalkyl; —D—$(CR^{26}R^{26'})_u R^{27}$;

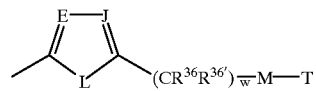

$NR^{29}R^{29'}$; and

When Z is cycloalkyl or heterocycloalkyl, preferred is where Z is an optionally substituted piperidine or piperazine.

When Z is —D—$(CR^{26}R^{26'})_uR^{27}$ u is from 0 to about 4, preferably 0 or 1. D is selected from —C≡C—, —CH=CH—, —N=N—, —O—, —S— and —$SO_2$—. Preferred is where D is —C≡C—, —CH=CH—, —N=N—, —O— or —S—; more preferred is —C≡C—, —CH=CH—, or —N=N—. Each $R^{26}$ and $R^{26'}$ each is independently selected from hydrogen, alkyl, alkenyl, alkynyl, aryl, heteroalkyl, heteroaryl, cycloalkyl, heterocycloalkyl, halogen, haloalkyl, hydroxy, and alkoxy preferably each $R^{26}$ is hydrogen and each $R^{26'}$ is independently hydrogen or lower alkyl. $R^{27}$ is selected from aryl, heteroaryl, alkyl, alkenyl, alkynyl, heteroalkyl, haloalkyl, heterocycloalkyl and cycloalkyl; preferably $R^{27}$ is aryl, heteroaryl, heterocycloalkyl or cycloalkyl. However, if D is —C≡C— or —CH=CH—, then $R^{27}$ may also be selected from —$CONR^{28}R^{28'}$ where (i) $R^{28}$ and $R^{28'}$ are independently selected from hydrogen, alkyl, alkenyl, alkynyl, haloalkyl, heteroalkyl, aryl, heteroaryl, cycloalkyl, and heterocycloalkyl, or (ii) $R^{28}$ and $R^{28'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms.

When Z is —$NR^{29}R^{29'}$, $R^{29}$ and $R^{29'}$ each is independently selected from hydrogen, alkyl, alkenyl, alkynyl, heteroalkyl, haloalkyl, aryl, heteroaryl, cycloalkyl, heteroalkyl, and —C(O)—Q—$(CR^{30}R^{30'})_vR^{31}$; preferably $R^{29}$ and $R^{29'}$ each is hydrogen, alkyl or aryl. When $R^{29}$ and/or $R^{29'}$ is —C(O)—Q—$(CR^{30}R^{30'})_vR^{31}$, v is from 0 to about 4; v is preferably 0 or 1. Q is selected from a covalent bond and —$NR^{32}$—; Q is preferably a covalent bond. Each $R^{30}$ and $R^{30'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{30}$ is hydrogen and each $R^{30'}$ is independently hydrogen or lower alkyl. $R^{31}$ and $R^{32}$ (i) each is independently selected from hydrogen, alkyl, alkenyl, alkynyl, heteroalkyl, haloalkyl, aryl, heteroaryl, cycloalkyl, and heterocycloalkyl, or (ii) $R^{31}$ and $R^{32}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms; preferably $R^{31}$ is alkyl, aryl, heteroaryl, cycloalkyl or heterocycloalkyl. Alternatively, $R^{29}$ and $R^{32}$, together with the nitrogen atoms to which they are bonded, join to form an optionally substituted heterocyclic ring containing from 5 to 8 ring atoms of which from 1 to 3 are heteroatoms.

Alternatively, $R^{29}$ and $R^{29'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms.

When Z is

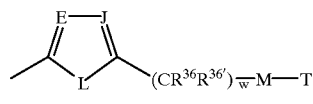

(referred to herein as Formula (A)), E and J are independently selected from —CH— and —N—; preferred is where E is —CH and J is —CH. L is selected from —S—, —O—, —$N(R^{38})$—, —$C(R^{38})$=$C(R^{38'})$—, —$N$=$C(R^{38})$—, and —N=N—; preferably L is —N=$C(R^{38})$— or —$C(R^{38})$=$C(R^{38'})$—. $R^{38}$ and $R^{38'}$ each is independently selected from hydrogen, alkyl, alkenyl, alkynyl, heteroalkyl, aryl, heteroaryl, cycloalkyl, and heterocycloalkyl; preferably hydrogen or lower alkyl. w is from 0 to about 4, preferably 0 or 1. Each $R^{36}$ and $R^{36'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; preferably each $R^{36}$ is hydrogen and each $R^{36'}$ is independently hydrogen or lower alkyl. M is selected from a covalent bond, —O—, —$SO_x$—, —C(O)—, —$C(O)NR^{39}$—, —$NR^{39}$—, and $NR^{39}C(O)$—; preferably M is —O—, —S—, $SO_2$—, —$C(O)NR^{39}$—, —$NR^{39}$—, and —$NR^{39}C(O)$—; more preferably M is —O—. x is from 0 to 2. $R^{39}$ is selected from hydrogen, alkyl, alkenyl, alkynyl, aryl, heteroaryl, heteroalkyl, heteroaryl, cycloalkyl, heterocycloalkyl, and haloalkyl; $R^{39}$ is preferably lower alkyl or aryl. T is —$(CR^{40}R^{40'})_y$—$R^{41}$. y is from 0 to about 4, preferably 0 or 1. Each $R^{40}$ and $R^{40'}$ is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy preferably each $R^{40}$ is hydrogen and each $R^{40'}$ is independently hydrogen or lower alkyl. $R^{41}$ is selected from hydrogen, alkyl, alkenyl, alkynyl, halogen, heteroalkyl, haloalkyl, aryl, heteroaryl, cycloalkyl, and heterocycloalkyl; preferably $R^{41}$ is lower alkyl or aryl. Alternatively, $R^{39}$ and $R^{41}$, together with the atoms to which they are bonded, join to form an optionally substituted heterocyclic ring containing from 5 to 8 (preferably 5 or 6) atoms of which 1 to 3 (preferably 1 or 2) are heteroatoms. Alternatively, $R^{38}$ and $R^{41}$, together with the atoms to which they are bonded, join to form an optionally substituted heterocyclic ring containing from 5 to 8 (preferably 5 or 6) atoms of which 1 to 3 (preferably 1 or 2) are heteroatoms.

III. Compound Preparation

The compounds of the invention can be prepared using a variety of procedures.

The starting materials used in preparing the compounds of the invention are known, made by known methods, or are commercially available. Particularly preferred syntheses are described in the following general reaction schemes. (The R groups used to illustrate the reaction schemes do not necessarily correlate to the respective R groups used describe the various aspects of the Formula I compounds. That is, for example, $R^1$ in Formula (I) does not represent the same moiety as $R_1$ here.) Specific examples for making the compounds of the present invention are set forth in Section VIII, below.

Scheme 1

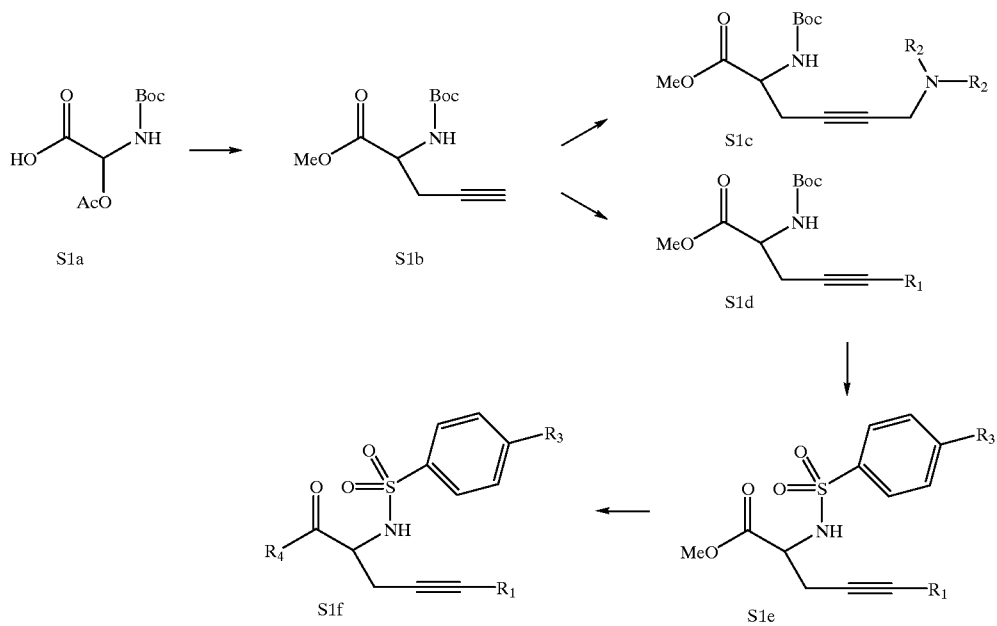

In Scheme 1, the acetate S1a depicted as starting material can be prepared from commercially available sources and converted to various alkenyl- and alkynyl-methyl derivatives such as S1b as described in *Tetrahedron Lett.* 1994, 35 (22), 3669. These alkenes and alkynes can then be further functionalized using any of the methods known to artisans skilled in the art which allow manipulations of such moieties. One preferred method includes a Mannich type process to provide aminomethyl compounds of type S1c.

Another preferred process includes, but is not limited to, metal catalyzed coupling reactions well known to the skilled artisan which provide a wide range of functionalities (S1d) including aromatic and heteroaromatic rings, as well as olefin-containing substituents.

The amino functionality contained in the alkenes or alkynes of choice can be deprotected and then acylated using methods well known to the skilled artisan. Such a process can be used to access a wide range of functionalities including but not limited to amides, ureas, carbamates or sulfonamides such as S1e depicted in Scheme 1. These acyl type derivatives can again be further functionalized using well known methods if desired.

If desired, the ester functionality in compounds of type S1e can be transesterified, saponified to an acid or treated with basic hydroxyl amine to give hydroxamic acid.

Scheme 2

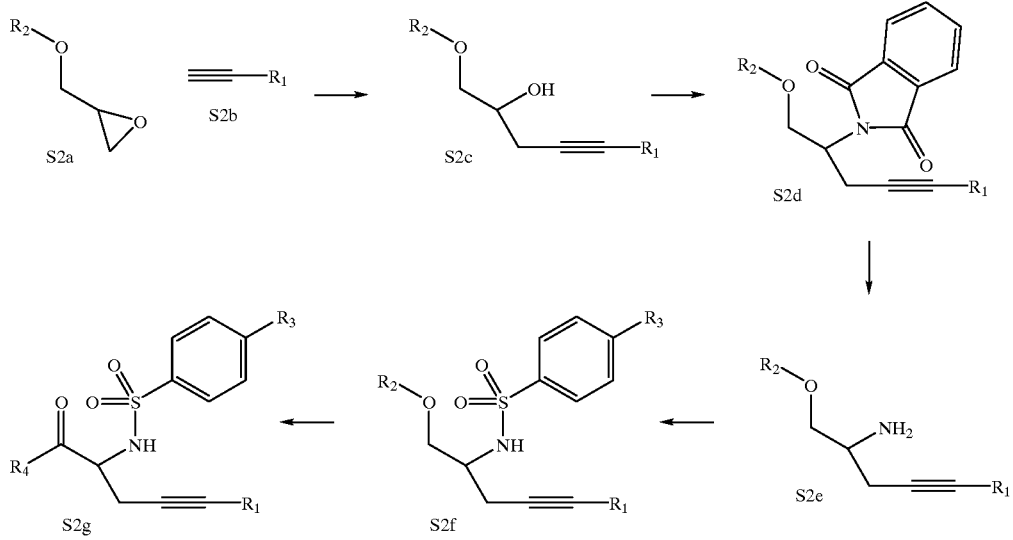

The epoxide S2a depicted as starting material is available in both enantiomeric forms from commercial sources with $R^2$ present as a variety of removable protecting groups. Nucleophillic opening of this epoxide with alkynyl lithium nucleophiles is well known and provides compounds of type S2c. Many other alkyl, alkenyl, aryl, and heteroaryl anion nucleophiles as well as moieties containing heteroatom nucleophiles are well known to open epoxides in a similar manner and any of these can be used to derivatise the system similarly.

Replacement of the hydroxyl group in S2c with an amino moiety can be accomplished according to a number of well known protocols including a Mitsunobu inversion with phthalimide to give S2d followed by decomposition with hydrazine to give the free amine S2e.

Compounds of this invention then can be accessed by first sulfonylating the free amine. The resulting sulfonamide can then be further manipulated to give more complex forms of S2f. Finally, the $R^2$ protecting group is removed and the resulting primary alcohol transformed to the carboxylic acid derivative of choice via any of the well known oxidative methods including Jones oxidation to give S2g.

Scheme 3

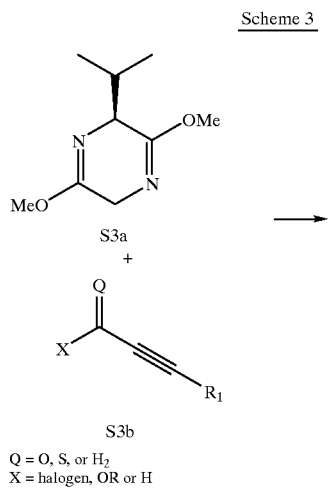

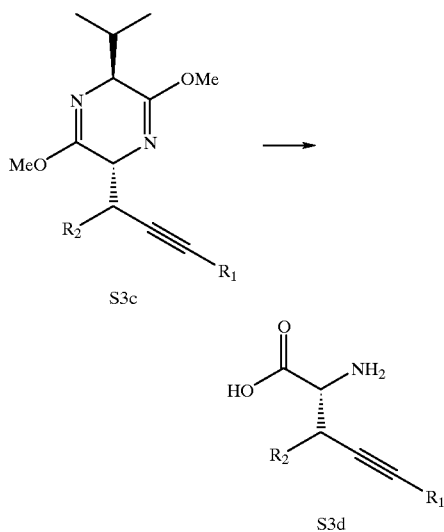

Nucleophillic additions of the anion generated from amino acid condensate S3a into various nucleophiles such as S3b are a well known method for generating amino acids of type S3d in an asymmetric way (*Synthesis of Optically Active a-Amino Acids*. Robert M. Williams; Pergamon Press, New York, 1989). These can then be functionalized according to known methods and carried forward as described above to generate a variety of compounds which fall within the scope of this invention.

Scheme 4

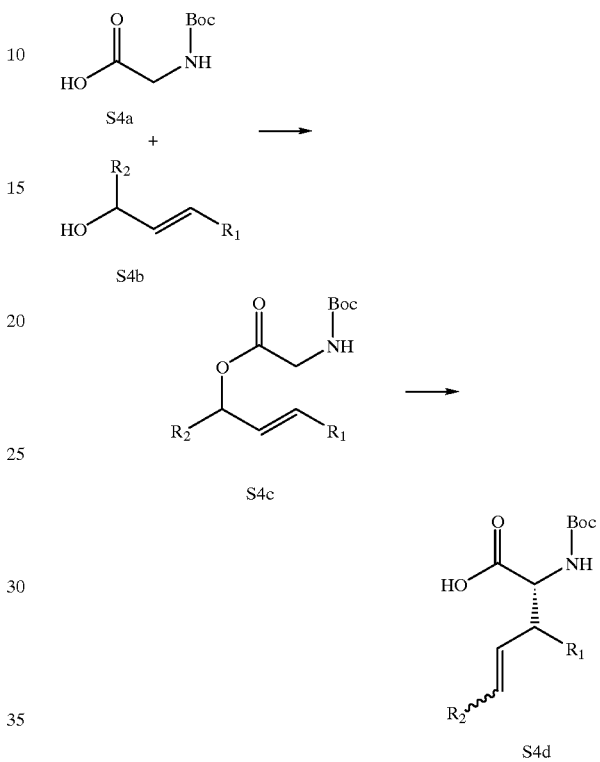

The esters of allylic alcohols and Boc-Glycein can be coupled according to known methods to give esters of type S4c. When treated with two equivalents of strong base in the presence of certain bidentate chelating agents such as $Zn^{++}$, these molecules undergo a Claisen rearrangement to give amino acids of type S4d which can then be functionalized according to known methods and then carried forward to generate a variety of compounds which fall within the scope of this invention (Synlett, 1996, 975).

A variety of compounds can be generated in a similar fashion, using the guidance of the schemes above.

It is recognized that it is preferable to use a protecting group for any reactive functionality such as a carboxyl, hydroxyl and the like, during the formation of the sultamester. This is standard practice, well within the normal practice of the skilled artisan.

In the above scheme, where R is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

These steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

IV. Methods of Use

Metalloproteases (MPs) found in the body operate, in part, by breaking down the extracellular matrix, which comprises extracellular proteins and glycoproteins. Inhibitors of metalloproteases are useful in treating diseases caused, at least in part, by the breakdown of such proteins and glycoproteins. These proteins and glycoproteins play an important role in maintaining the size, shape, structure and stability of tissue in the body. Thus, MPs are intimately involved in tissue remodeling.

As a result of this activity, MPs have been said to be active in many disorders involving either the: (1) breakdown of tissues including opthalmic diseases; degenerative diseases, such as arthritis, multiple sclerosis and the like; and metastasis or mobility of tissues in the body; or (2) remodeling of tissues including cardiac disease, fibrotic disease, scarring, benign hyperplasia, and the like.

The compounds of the present invention prevent or treat disorders, diseases and/or unwanted conditions which are characterized by unwanted or elevated activity by MPs. For example, the compounds can be used to inhibit MPs which:

1. destroy structural proteins (i.e. the proteins that maintain tissue stability and structure);
2. interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561]; and
3. facilitate processes which are undesired in the subject being treated, for example, the processes of sperm maturation, egg fertilization and the like.

As used herein, an "MP related disorder" or "MP related disease" is one that involves unwanted or elevated MP activity in the biological manifestation of the disease or disorder; in the biological cascade leading to the disorder; or as a symptom of the disorder. This "involvement" of the MP includes:

1. The unwanted or elevated MP activity as a "cause" of the disorder or biological manifestation, whether the activity is elevated genetically, by infection, by autoimmunity, trauma, biomechanical causes, lifestyle [e.g. obesity] or by some other cause;
2. The MP as part of the observable manifestation of the disease or disorder. That is, the disease or disorder is measurable in terms of the increased MP activity. From a clinical standpoint, unwanted or elevated MP levels indicate the disease, however, MPs need not be the "hallmark" of the disease or disorder; or
3. The unwanted or elevated MP activity is part of the biochemical or cellular cascade that results or relates to the disease or disorder. In this respect, inhibition of the MP activity interrupts the cascade, and thus controls the disease.

The term "treatment" is used herein to mean that, at a minimum, administration of a compound of the present invention mitigates a disease associated with unwanted or elevated MP activity in a mammalian subject, preferably in humans. Thus, the term "treatment" includes: preventing an MP-mediated disease from occurring in a mammal, particularly when the mammal is predisposed to acquiring the disease, but has not yet been diagnosed with the disease; inhibiting the MP-mediated disease; and/or alleviating or reversing the MP-mediated disease. Insofar as the methods of the present invention are directed to preventing disease states associated with unwanted MP activity, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to MP-related disorders, such that administration of the compounds of the present invention may occur prior to onset of the disease. The term does not imply that the disease state be completely avoided. For example, osteoarthritis (OA) is the most common rhueumatological disease with some joint changes radiologically detectable in 80% of people over 55 years of age.

Fife, R. S., "A Short History of Osteoarthritis", Osteoarthritis: Diagnosis and Medical/Surgical Management, R. W. Moskowitz, D. S. Howell, V. M. Goldberg and H. J. Mankin Eds., p 11–14 (1992). A common risk factor that increases the incidence of OA is traumatic injury of the joint. Surgical removal of the meniscus following knee injury increases the risk of radiographically detectable OA and this risk increases with time. Roos, H et al. "Knee Osteoarthritis After Menisectomy: Prevalence of Radiographic Changes After Twenty-one Years, Compared with Matched Controls." Arthritis Rheum., Vol.41, pp 687–693; Roos, H et al. "Osteoarthritis of the Knee After Injury to the Anterior Cruciate Ligament or Meniscus: The Influence of Time and Age." Osteoarthritis Cartilege., Vol. 3, pp 261–267 (1995). Thus, this patient population is identifiable and could receive administration of a compound of the present invention before progression of the disease. Thus, progression of OA in such individuals would be "prevented".

Advantageously, many MPs are not distributed evenly throughout the body. Thus, the distribution of MPs expressed in various tissues are often specific to those tissues. For example, the distribution of metalloproteases implicated in the breakdown of tissues in the joints is not the same as the distribution of metalloproteases found in other tissues. Though not essential for activity or efficacy, certain diseases, disorders, and unwanted conditions preferably are treated with compounds that act on specific MPs found in the affected tissues or regions of the body. For example, a compound which displays a higher degree of affinity and inhibition for an MP found in the joints (e.g. chondrocytes) would be preferred for treatment of a disease, disorder, or unwanted condition found there than other compounds which are less specific.

In addition, certain inhibitors are more bioavailable to certain tissues than others. Choosing an MP inhibitor which is more bioavailable to a certain tissue and which acts on the specific MPs found in that tissue, provides for specific treatment of the disease, disorder, or unwanted condition. For example, compounds of this invention vary in their ability to penetrate into the central nervous system. Thus, compounds may be selected to produce effects mediated through MPs found specifically outside the central nervous system.

Determination of the specificity of an inhibitor of a specific MP is within the skill of the artisan in that field. Appropriate assay conditions can be found in the literature. Specifically, assays are known for stromelysin and collagenase. For example, U.S. Pat. No. 4,743,587 references the procedure of Cawston, et al., *Anal Biochem* (1979) 99:340–345. See also, Knight, C. G. et al., "A Novel Coumarin-Labelled Peptide for Sensitive Continuous Assays of the Matrix Metalloproteases", *FEBS Letters,* Vol. 296, pp. 263–266 (1992). The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

The compounds of this invention are also useful for prophylactic or acute treatment. They are administered in any way the skilled artisan in the fields of medicine or pharmacology would desire. It is immediately apparent to the skilled artisan that preferred routes of administration will depend upon the disease state being treated and the dosage form chosen. Preferred routes for systemic administration include administration perorally or parenterally.

However, the skilled artisan will readily appreciate the advantage of administering the MP inhibitor directly to the affected area for many diseases, disorders, or unwanted conditions. For example, it may be advantageous to administer MP inhibitors directly to the area of the disease, disorder, or unwanted condition such as in the area affected by surgical trauma (e.g., angioplasty), scarring, burning (e.g., topical to the skin), or for opthalmic and periodontal indications.

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury; to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultaviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus [CMV]; retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response and in the processing of cytokines, the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

V. Compositions

The compositions of the invention comprise:

(a) a safe and effective amount of a compound of the invention; and (b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit metalloproteases at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel" RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit" coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

VI. Methods of Administration

This invention also provides methods of treating or preventing disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating or preventing disorders described above.

Compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by, using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. For treatment of oral diseases, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

VII. Preparation and Use of Antibodies

Metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease in vivo or in vitro cell culture.

In addition, the compounds of Formula (I) can be conjugated to carriers which permit the use of these compounds in immunization protocols to prepare antibodies, specifically immunoreactive with the compounds of the invention. Typical conjugation methods are known in the art. These antibodies are then useful both in therapy and in monitoring the dosage of the inhibitors.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

VIII. EXAMPLES

Compound Preparation

Compounds are analyzed using $^1$H and $^{13}$CNMR, elemental analysis, mass spectra and/or infrared spectra, as appropriate.

Typically tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:

| | |
|---|---|
| MeOH: methanol | Et$_3$N: triethylamine |
| EtOAc: ethylacetate | Et$_2$O: diethylether |
| Ph: phenyl | boc: t-butyloxycarbonyl |
| DMF: N,N-dimethylformamide | acac: acetyl acetate |
| DME: dimethoxyethane | dil.: dilute |
| conc.: concentrated | wrt.: with respect to |
| DCC: 1,3-Dicyclohexylcarbodiimide | HOBT: 1-Hydroxybenzotriazole |

The R groups used to illustrate the compound examples do not correlate to the respective R groups used to describe the various moieties of Formula (I). That is, for example R$^1$, R$^2$ and R$^3$ used to describe Formula (I) in the Summary of the Invention and Section II of the Detailed Description do not represent the same moieties as R$_1$, R$_2$, and R$_3$ in this Section VIII.

Examples 1–24

The following chemical formula along with Table 1 shows the structure of compounds made according to the description in Examples 1–24 described below:

TABLE 1

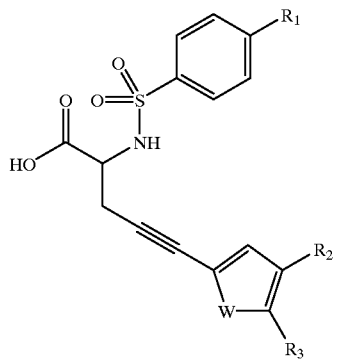

| Example | R$_1$ | W | R$_2$ | R$_3$ |
|---|---|---|---|---|
| 1 | 4-F-phenyl | —CH=CH— | —H | —H |
| 2 | 2-phenoxy-phenyl | —CH=CH— | —H | —H |
| 3 | 4-OMe-phenyl | —CH=CH— | —H | —H |
| 4 | 4-OMe-phenyl | —CH=CH— | —H | —N—Morpholine |

TABLE 1-continued
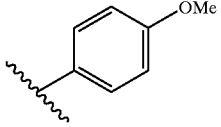
| Example | R₁ | W | R₂ | R₃ |
|---|---|---|---|---|
| 5 | 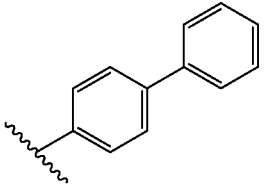 (OMe) | —CH=CH— | —N— Morpholine | —H |
| 6 | 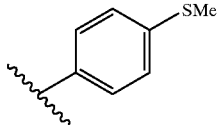 (biphenyl) | —CH=CH— | —H | —H |
| 7 | 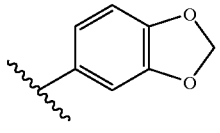 (SMe) | —CH=CH— | —H | —H |
| 8 | 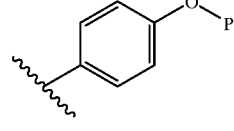 (benzodioxole) | —CH=CH— | —H | —H |
| 9 | 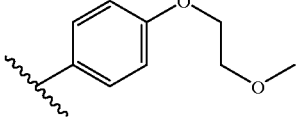 (O-Ph) | —CH=CH— | —H | —H |
| 10 | 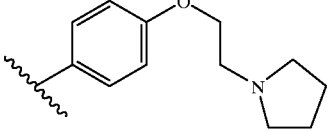 (O-CH₂CH₂-OMe) | —CH=CH— | —H | —H |
| 11 | (O-CH₂CH₂-pyrrolidine) | —CH=CH— | —H | —H |

TABLE 1-continued

| Example | R₁ | W | R₂ | R₃ |
|---------|----|----|----|----|
| 12 | 3-ethoxyphenyl | —CH=CH— | —H | —H |
| 13 | 4-methylphenyl-C≡C— | —CH=CH— | —H | —H |
| 14 | 4-methoxyphenyl-C≡C— | —CH=CH— | —H | —H |
| 15 | phenyl-N=N— | —CH=CH— | —H | —H |
| 16 | 4-phenoxyphenyl | —CH=CH— | —H | —H |
| 17 | 4-methoxyphenyl-C≡C— | —CH=CH— | —H | —H |
| 18 | 4-methoxyphenyl | —CH=CH— | —H | —H |

TABLE 1-continued

[Structure: 4-R₁-phenylsulfonyl-NH-CH(COOH)-CH₂-C≡C-[5-membered heterocycle with W, R₂ at 3-position, R₃ at 4-position]]

| Example | R₁ | W | R₂ | R₃ |
|---|---|---|---|---|
| 19 | 4-MeO-phenyl | —O— | —H | —H |
| 20 | 4-(2-methoxyethoxy)-phenyl | —O— | —H | —H |
| 21 | 4-(2-(pyrrolidin-1-yl)ethoxy)-phenyl | —O— | —H | —H |
| 22 | 4-MeO-phenyl | —S— | —H | —H |
| 23 | 4-MeO-phenyl | —NMe— | —H | —H |
| 24 | 4-(butoxy)-phenyl | —CH═CH— | —H | —H |

Example 1
Preparation of 2-{[4'-Fluoro-(1,1'-biphenyl)-4-yl]-sulfonyl}-amino-5-phenylpent-4-ynoic acid a. Methyl 2-{[4'-fluoro-(1,1'-biphenyl)-4-yl]-sulfonyl}-amino-5-phenylpent-4-ynoate:

The starting Methyl 2-N-boc-amino-5-phenylpent-4-ynoate 1c (382 mg, 1.26 mmol, prepared as described in *Tetrahedron Lett.*, 1994, 35, 3669), is taken in 10 mL of MeOH and treated with 0.5 mL of SO₂Cl. The resulting mixture is stirred for 4 hr and then evaporated to dryness. The resulting solid is taken in 6 mL of CH₂Cl₂ in the presence of 0.5 mL of Et₃N and treated with 2-4'-fluorobiphenylsulfonyl chloride (306 mg, 1.13 mmol.) and the resulting mixture is stirred at room temperature ("rt") for 18 hr and then partitioned between 1N HCl and EtOAc. The organic layer is then washed with brine, dried over MgSO₄, filtered and evaporated to give a pale yellow solid which is recrystallized from EtOAc:Hexanes to give a white solid.

ESI MS: m/z (rel intensity) 455.0 (100, M+NH₄⁺), 437.7 (20, M+H⁺).

b. The methyl ester 1a (110 mg, 0.25 mmol) is treated with KOH (250 mg, 4.46 mmol) in 15 mL of MeOH:H₂O (10:1)

and stirred for 24 hr at room temperature. A white precipitate comes out of solution. The material is concentrated and partitioned between 1N HCl and EtOAc. The organic layer is washed with brine, dried over MgSO$_4$, filtered and evaporated. The solid residue is recrystallized from EtOAc:Hexanes (2:1) to give the title compound as white crystals.

ESI MS: m/z (rel intensity) 441.0 (100, M+NH$_4^+$), 424.0 (85, M+H$^+$).

Example 2

Preparation of 2-(4-Phenyloxyphenylsulfonyl)-amino-5-phenylpent-4-ynoic acid a. Methyl 2-(4-phenyloxyphenylsulfonyl)-amino-5-phenylpent-4-ynoate:

The starting t-butyl-carbamate 1c (734 mg, 2.42 mmol) is converted to the title sulfonamide as described for example 1a. The crude residue is adsorbed onto silica and then eluted through a column of flash silica with Hexanes:EtOAc (2:1 to 1:2) to give a clear syrup which solidified upon standing.

ESI MS: m/z (rel intensity) 466.9 (80, M+NH$_4^+$), 449.9 (100, M+H$^+$).

b. The methyl ester 2a (308 mg, 0.71 mmol) is hydrolyzed to its relative carboxylic acid as described for example 1b. The solid residue is recrystallized from EtOAc:Hexanes (1:1) to give the title compound as white crystals.

ESI MS: m/z (rel intensity) 453.0 (100, M+NH$_4^+$), 435.9 (75, M+H$^+$).

Example 3

Preparation of 2-{[4'-Methoxy-(1,1'-biphenyl)-4yl]-sulfonyl}-amino-5-phenylpent-4-ynoic acid a. Methyl 2-(4-iodophenylsulfonyl)-amino-5-phenylpent-4-ynoate:

The starting t-butyl-carbamate 1c (3.38 g, 11.2 mmol) is converted to the title sulfonamide upon treatment with 4-iodobenzene sulfonyl chloride (4.05 g, 13.4 mmol) as described for example 1a. The crude residue is adsorbed onto silica and then eluted through a column of flash silica with Hexanes:Et$_2$O (7:3 to 2:3) to give 3.9 g a yellow gum which solidifies upon standing.

ESI MS: m/z (rel intensity) 486.9 (100, M$^+$+NH$_4^+$), 469.8 (25, M+H$^+$).

b. Methyl 2-{[4'-methoxy-(1,1'-biphenyl)-4-yl]-sulfonyl}-amino-5-phenylpent-4-ynoate:

The starting sulfonamide 3a (804 mg, 1.71 mmol) and 4-methoxyphenylboronic acid (391 mg, 2.57 mmol) is taken in 15 mL of benzene, 2 mL of EtOH and 2 mL of water and treated with Pd(PPh$_3$)$_4$ and 100 mg of Na$_2$CO$_3$. The mixture is brought to a mild reflux for 18 hr and then partitioned between EtOAc and 1N HCl. The organic layer is washed with brine, dried over MgSO$_4$, filtered and evaporated. The residue is recrystallized from hexanes:EtOAc (2:1) to give off-white solid.

ESI MS: m/z (rel intensity) 449.9 (100, M+NH$_4^+$), 466.9 (75, M+H).

c. The methyl ester 3b (286 mg, 0.64 mmol) is hydrolyzed to its relative carboxylic acid as described for example 1b. The solid residue is recrystallized from EtOAc:Hexanes, (1:1) to give white crystals.

ESI MS: m/z (rel intensity) 453.0 (100, M+NH$_4^+$), 436.0 (60, M+H$^+$).

Example 4

Preparation of 2-{[4'-Methoxy-(1,1'-biphenyl)-4-yl]-sulfonyl}-amino-5-(4-morpholino-phenyl)-pent-4ynoic acid a. Methyl 2-N-boc-amino-5-(4-morpholinophenyl)-pent-4-ynoate: 4-Iodoaniline (6.2 g, 28.4 mmol) is taken in 50 mL of DMF in the presence of 8 mL of bromoethyl ether and 10 mL of Et$_3$N and heated to 60° C. for 24 hr. The mixture is then diluted with EtOAc, and washed 3x with dil. NaHCO$_3$, 1x with brine, dried over MgSO$_4$, filtered and evaporated. The residue is then recrystallized from MeOH to give 4.21 g of 4-iodophenylmorpholine as a pale brown solid.

The starting methyl 2-N-boc-amino-5-pent-4-ynoate 4e (1.62 g, 7.14 mmol, *Tetrahedron Lett.*, 1994, 35, 3669) and the 4-iodophenylmorpholine (2.06 g, 7.14 mmol) are taken in 16 mL of DMF in the presence of 1.6 mL of Et$_3$N, Pd(PPh$_3$)$_4$ (650 mg, 0.56 mmol), and CuI (240 mg, 1.26 mmol). The mixture is then heated to 60° C. for 20 hr. and then partitioned between EtOAc and dil. NaHCO$_3$. The organic layer is washed 2x with water, 1x with brine, dried over MgSO$_4$, filtered and evaporated to give a deep red residue, which is adsorbed onto silica and eluted through a column of flash silica with hexanes:EtOAc (4:1 to 1:1) to give a yellow solid.

ESI MS: m/z (rel intensity) 389.1 (100, M+H$^+$).

b. Methyl 2-(4-iodophenylsulfonyl)-amino-5-(4-morpholinophenyl)-pent-4-ynoate:

The starting t-butylcarbamate 4a (1.23 g, 3.17 mmol) is converted to the title sulfonamide upon treatment with 4-iodobenzene sulfonyl chloride (1.15 g, 3.80 mmol) as described for example 1a. The crude residue is adsorbed onto silica and then eluted through a column of flash silica with Hexanes:EtOAc (3:1 to 1:2) to give a pale yellow solid.

ESI MS: m/z (rel intensity) 554.0 (100, M+H$^+$).

c. Methyl 2-{[4'-methoxy-(1,1'-biphenyl)-4-yl]-sulfonyl}-amino-5-(4-morpholino-phenyl)-pent-4-ynoate:

The starting sulfonamide 4b (420 mg, 0.76 mmol) is converted to the title compound with 4-methoxyphenylboronic acid (172 mg, 1.14 mmol) as described for compound 3b. The resulting solid is recrystallized from EtOAc to give a pale yellow solid.

ESI MS: m/z (rel intensity) 535.0 (100, M+H$^+$).

d. The methyl ester 4c (128 mg, 0.24 mmol) is hydrolyzed to its relative carboxylic acid as described for example 1b. The solid residue is recrystallized from EtOAc:MeOH (10:1) to give white crystals.

ESI MS: m/z (rel intensity) 543.0 (40, M+Na$^+$), 521.0 (100, M+H$^+$).

Example 5

Preparation of 2-{[4'-Methoxy-(1,1'-biphenyl)-4-yl]-sulfonyl}-amino-5-(3-morpholinophenyl)-pent-4-ynoic acid a. Methyl 2-N-boc-amino-5-(3-morpholinophenyl)-pent-4-ynoate: 3-Iodoaniline is converted to 3-iodophenylmorpholine as described for 4a. The residue is then adsorbed onto silica and eluted through flash silica with hexanes:EtOAc (1:1 to 0:1) to give 3-iodophenylmorpholine as a yellow gum.

The starting free acetylene 4e (1.4 g, 6.1 mmol) and the 4-iodophenylmorpholine (1.68 g, 5.81 mmol) are coupled as described for 4a. The crude product is adsorbed onto silica and eluted through a column of flash silica with hexanes:EtOAc (4:1) to give a yellow gum.

ESI MS: m/z (rel intensity) 389.1 (100, M+H$^+$).

b. Methyl 2-(4-iodophenylsulfonyl)-amino-5-(3-morpholinophenyl)-pent-4-ynoate: The starting t-butylcarbamate 5a (1.58 g, 4.07 mmol) is converted to the title sulfonamide upon treatment with 4-iodobenzene sulfonyl chloride (1.11 g, 3.66 mmol) as described for example 1a. The crude residue is adsorbed onto silica and then eluted through a column of flash silica with Hexanes:EtOAc (4:1 to 0:1) to give a pale yellow solid.

ESI MS: m/z (rel intensity) 554.8 (100, M+H$^+$).

c. Methyl 2-{[4'-methoxy-(1,1'-biphenyl)-4-yl]-sulfonyl}-amino-5-(3-morpholino-phenyl)-pent-4-ynoate:

The starting sulfonamide 5b (367 mg, 0.66 mmol) is converted to the title compound with 4-methoxyphenylboronic acid (151 mg. 1.14 mmol) as described. for compound 3b. The crude product is adsorbed onto silica and then eluted through a column of flash silica with Hexanes:EtOAc (4:1 to 1:1) to give a pale orange-yellow, foamy solid.

ESI MS: m/z (rel intensity) 535.0 (100, M+H$^+$).

d. The methyl ester 5c (250 mg, 0.47 mmol) is hydrolyzed to its relative carboxylic acid as described for example 4d. The solid residue is eluted through a short silica gel column with EtOAc:MeOH (1:0 to 4:1) to give a brownish solid ESI MS: m/z (rel intensity) 521.0 (100, M+H$^+$).

Example 6

Preparation of 2-{[(1,1'-4',1"-Triphenyl)-4-yl]-sulfonyl}-amino-5-phenylpent-4-ynoic acid a. Methyl 2-{[(1,1'-4',1"-Triphenyl)-4-yl]-sulfonyl}-amino-5-phenylpent-4-ynoate: The starting sulfonamide 3a (1.0 g, 2.13 mmol) and biphenylboronic acid (633 mg, 3.2 mmol) are coupled as described for compound 3b. The residue is recrystallized from hexanes:EtOAc (1:10) to give an off-white solid.

ESI MS: m/z (rel intensity) 513.2 (30, M+NH$_4^+$), 496.1 (25, M+H$^+$).

b. The methyl ester 6a (497 mg, 1.0 mmol) is hydrolyzed to its relative carboxylic acid as described for example 1b. The solid residue is recrystallized from EtOAc:Hexanes (2:1) to give a tan solid.

ESI MS: m/z (rel intensity) 505.0 (12, M+Na$^+$), 499.0 (40, M+NH$_4^+$), 482.0 (100, M+H$^+$).

Example 7

Preparation of 2-{[4'-Methylthio-(1,1'-biphenyl)p-4-yl]-sulfonyl}-amino-5-phenylpent-4-ynoic acid a. Methyl 2-{[4'-Methylthio-(1,1'-biphenyl)p-4-yl]-sulfonyl}-amino-5-phenylpent-4-ynoate: The starting sulfonamide 3a (1.0 g, 2.13 mmol) and 4-methylthiophenylboronic acid (540 mg, 3.2 mmol) are coupled as described for compound 3b. The residue is recrystallized from hexanes:EtOAc (1:5) to give an orange solid.

ESI MS: m/z (rel intensity) 483.0 (20, M+NH$_4^+$), 466.0 (60, M+H$^+$), 279.0 (100).

b. The methyl ester 7a (665 mg, 1.4 mmol) is hydrolyzed to its relative carboxylic acid as described for example 1b. The solid residue is recrystallized from EtOAc:Hexanes (2:1) to give a yellowish solid.

ESI MS: m/z (rel intensity) 469.0 (3 0, M+NH$_4^+$), 452.0 (60, M+H$^+$), 279.0 (100).

Example 8

Preparation of 2-{[3',4'-Methylenedioxy-(1,1'-biphenyl)-4-yl]-sulfonyl}-amino-5-phenylpent-4-ynoic acid a. Methyl 2-{[3',4'-Methylenedioxy-(1,1'-biphenyl)-4-yl]-sulfonyl}-amino-5-phenylpent-4-ynoate: The starting sulfonamide 3a (804 mg, 1.72 mmol) and 4-methylenedioxyphenylboronic acid (430 mg, 2.59 mmol) are coupled to give the title compound as described for compound 3b. The crude product is adsorbed onto silica and eluted through flash silica with hexanes:EtOAc (2:1 to 1:3) to give a pale yellow solid.

ESI MS: m/z (rel intensity) 481.0 (100, M+NH$_4^+$), 464.0 (7, M+H$^+$).

b. Methyl ester 8a (391 mg, 0.84 mmol) is hydrolyzed to its relative carboxylic acid as described for example 1b. The solid residue is recrystallized from EtOAc:Hexanes (2:1), to give white crystals.

ESI MS: m/z (rel intensity) 466.9 (70, M+NH$_4^+$), 449.9 (100, M+H$^+$).

Example 9

Preparation of 2-{[4'-Phenyloxy-(1,1'-biphenyl)-4-yl]-sulfonyl}-amino-5-phenylpent-4-ynoic acid See: to M. D. Vleeschauwer and J. Y. Gauthier, Synlett, 1997, 375.

a. 4-Phenyloxyphenyl boronic acid: Mg turnings (820 mg, 34.2 mmol) are suspended in THF (60 mL) in a three-necked flask fitted with addition funnel and condenser. A crystal of iodine is added to the suspension. Phenyloxy phenyl bromide (5 mL, 28.5 mmol) in THF (15 mL) is added dropwise using the addition funnel to the Mg/I$_2$ suspension, maintaining a slow reflux of the solvent, then after the completion of addition the mixture is brought to reflux for the next 3 hrs. After allowing the mixture to cool down to room temperature, triethyl borate (5.8 mL, 34.20 mmol) in THF (15 mL) is added dropwise via the addition funnel. To the mixture is added 10% ammonium chloride (50 mL), the layers are separated and the aqueous layer is extracted with EtOAc (50 mL). The combined organic extracts are dried over MgSO$_4$, filtered and the solvents removed by rotary evaporation. The crude solid product is recrystallized from EtOAc/hexanes mixtures to afford an off-white boronic acid product, which is stored under refrigeration.

b. Methyl-[4'-phenyloxy-(1,1'-biphenyl)-4-yl]-sulfide: Bromothioanisole (500 mg, 2.39 mmol) and Pd(PPh$_3$)$_4$ (138 mg, 0.12 mmol) are mixed in degassed benzene (20 mL). 2 M Na$_2$CO$_3$ (3 mL, 6.0 mmol) is added to the mixture followed by boronic acid (563 mg, 2.63 mmol). The biphasic mixture is refluxed overnight. To the cooled reaction mixture is added water (10 mL). The layers are separated and the aqueous layer is extracted with EtOAc (2×10 mL). The combined organic extracts are dried over MgSO$_4$. Filtration of the mixture followed by removal of the solvent by rotary evaporation affords a crude solid product, which is filtered through a plug of silica using EtOAc as solvent. The filtrate is evaporated and the solid residue is recrystallized using methanol to afford the title compound c. Methyl-[4'-phenyloxy-(1,1'-biphenyl)-4-yl]-sulfoxide: The sulfide (460 mg, 1.58 mmol) is dissolved in CH$_2$Cl$_2$ (50 mL). The solution is cooled to 0° C., and mCPBA ( 388 mg, 1.58 mmol) is added in 4 portions over 10 mins. The reaction mixture is quenched with 10% Na$_2$S$_2$O$_3$ (10 mL). The layers are separated and the organic layer is washed with satd NaHCO$_3$ (5 mL). The washed organic layer is dried over MgSO$_4$, filtered and concentrated via rotary evaporation to afford a crude sulfoxide which is taken directly to the next step without further purification.

d. Acetoxymethyl-[4'-phenyloxy-(1,1'-biphenyl)-4-yl]-sulfide: The above crude sulfoxide is mixed with NaOAc (750 mg, excess) in Ac$_2$O (5 mL). The suspension is heated to 140° C. for 3 hrs. The solvent is removed via rotary evaporation and the residue is dissolved in EtOAc (10 mL). The solution is washed with satd NaHCO$_3$, the layers separated and the organic layer dried with MgSO$_4$. Filtration of the solvent followed by concentration by rotary affords the a-acetoxy sulfide which is taken as crude to the next step.

e. Acetoxymethyl-[4'-phenyloxy-(1,1'-biphenyl)-4-yl]-sulfone: The crude sulfide 9d is dissolved in 1:2 MeOH/CH$_2$Cl$_2$ (12 mL) and cooled to 0° C. MMPP (1.08 g, 1.74 mmol) is added in one portion. The reaction mixture is stirred at 0° C. for 30 mins. Water (5 mL) and CH$_2$Cl$_2$ (5 mL) are added to the reaction mixture and the layers separated. The organic layer is washed with satd NaHCO$_3$ solution and then dried with MgSO$_4$. Filtration followed by removal of the solvent by rotary evaporation affords a solid which is purified by recrystallization from EtOAc/hexanes mixtures to give a white solid.

f. [4'-phenyloxy-(1,1'-biphenyl)-4-yl]-sulfonate: The sulfone (400 mg, 1.09 mmol) is dissolved in 1:2 MeOH/THF (9 mL). The solution is cooled to 0° C. and 1 M NaOH (1.1 mL, 1.1 mmol) is added dropwise. The solvents are removed by rotary evaporation and the residual water is removed by azeotroping with benzene. The solid is taken as crude to the next step.

g. [4'-phenyloxy-(1,1'-biphenyl)-4-yl]-sulfonyl chloride: The above crude sulfinate is dissolved in $CH_2Cl_2$ (10 mL) at 0° C. To the solution is added 1 M sulfuryl chloride (1.1 mL, 1.1 mmol). After the addition is complete, the reaction mixture is stirred at 0° C. for another 30 mins. To the reaction mixture is added water (5 mL). The layers are separated, the organic layer is dried with $MgSO_4$ and finally filtered. Removal of the organic solvent by rotary evaporation affords the crude sulfonyl chloride which is purified by chromatography on silica gel (3:1 hexanes/EtOAc) to afford the pure sulfonyl chloride.

h. The sulfonyl chloride 9g is coupled to methyl ester 1c as described for compound 1a. This material is then saponified and purified as described for example 1.

Example 10

Preparation of 2-{[4'-(2-Methoxyethoxy)-(1,1'-biphenyl)-4-yl]-sulfonyl}-amino-5-phenylpent-4-ynoic acid a. [4'-(2-Methoxyethoxy)-(1,1'-biphenyl)-4-yl]-sulfonyl chloride: 1-Bromo-4-(2-Methoxyethoxy)-benzene is converted to the title sulfonyl chloride according to the sequence of procedures listed for compounds 9a–g.

b. The sulfonyl chloride 10e is coupled to methyl ester 1c as described for compound 1a. This material is then saponified and purified as described for example 1.

ESI MS: m/z (rel intensity) 497.0 (50, $M+NH_4^+$), 479.9 (50, $M+H^+$).

Example 11

Preparation of 2-{[4'-(2-N-pyrrolidino-ethoxy)-(1,1'-biphenyl)-4-yl]-sulfonyl}-amino-5-phenylpent-4-ynoic acid a. [4'-(2-N-pyrrolidino-ethoxy)-(1,1'-biphenyl)-4-yl]-sulfonyl chloride: 1-Bromo-4-(2-N-pyrrolidino-ethoxy)-benzene is converted to the title sulfonyl chloride according to the sequence of procedures listed for compounds 9a–g.

b. The sulfonyl chloride 11e is coupled to methyl ester 1c as described for compound 1a. This material is then saponified and purified as described for example 1.

ESI MS: m/z (rel intensity) 519.1 (100, $M+H^+$).

Example 12

Preparation of 2-{[3'-Ethoxy-(1,1'-biphenyl)-4-yl]-sulfonyl}-amino-5-phenylpent-4-ynoic acid a. Methyl 2-{3'-Ethoxy-(1,1'-biphenyl)-4-yl]-sulfonyl}-amino-5-phenylpent-4-ynoate: The starting sulfonamide 3a (1.0 g, 2.13 mmol) and 3-ethoxyphenylboronic acid (532 mg, 3.2 mmol) are coupled as described for compound 3b. The residue is adsorbed onto silica and eluted through a flash silica column with hexanes:ETOAc (9:1 to 4:1) to give a yellow-orange gum.

ESI MS: m/z (rel intensity) 498.0 (25), 466.0 (100, $M-H^+$).

b. The methyl ester 12a (526 mg, 1.1 mmol) is hydrolyzed to its relative carboxylic acid as described for example 1b. The solid residue is adsorbed onto silica and eluted through a flash silica column with EtOAc:MeOH (1:0 to 4:1) to give a yellow solid.

ESI MS: m/z (rel intensity) 467.0 (30, $M+NH_4^+$), 449.9 (35, $M+H^+$), 279.0 (100).

Example 13

Preparation of 2-[4-(4-Methylphenyl)-acetylenylbenzenesulfonyl]-amino-5-phenylpent-4-ynoic acid a. Methyl 2-[4(4-Methylphenyl)-acetylenylbenzenesulfonyl]-amino-5-phenylpent-4-ynoate: The starting iodo sulfonamide 3a (0.7 g, 1.49 mmol) and 4-ethynyltoluene (0.21 g, 1.79 mmol) are taken in 10 mL of DMF in the presence of 0.42 mL of $Et_3N$, $Pd(PPh_3)_2Cl_2$ (26.1 mg, 0.037 mmol), and CuI (15 mg, 0.074 mmol). The mixture is then heated to 50° C. for 18 hr. and then partitioned between EtOAc and $H_2O$. The organic layer is washed with 1N HCl, aqueous $NaHCO_3$ and brine, dried over $MgSO_4$, filtered and evaporated to give a red residue which is adsorbed onto silica and eluted through a column of flash silica with hexanes: EtOAc (4:1) to give a pale yellow solid.

ESI MS: m/z (reel intensity) 475.1 (10, $M+NH_4^+$), 458.1 (100, $M+H^+$).

b. The methyl ester 13a (330 mg, 0.72 mmol) is hydrolyzed to its relative carboxylic acid as described for example 1b. The solid residue is triturated from EtOAc:hexane to give white crystals.

ESI MS: m/z (rel intensity) 444.1 (I100, $M+H^+$).

Example 14

Preparation of 2-[4-(4-Methoxyphenyl)-acetylenylbenzenesulfonyl]-amino-5-phenylpent-4-ynoic acid a. Methyl 2-[4-(4-Methoxyphenyl)-acetylenylbenzenesulfonyl]-amino-5-phenylpent-4-ynoate: The starting iodo sulfonamide 3a (0.54 g, 1.15 mmol) and 4-methoxyphenylacetylene (0.2 g, 1.49 mmol) are taken in 10 mL of DMF in the presence of 0.32 mL of $Et_3N$, $Pd(PPh_3)_2Cl_2$ (40.4 mg, 0.058 mmol), and CuI (24 mg, 0.128 mmol). The mixture is then heated to 55° C. for 18 hr. and then partitioned between EtOAc and $H_2O$. The organic layer is washed with 1N HCl, aqueous $NaHCO_3$ and brine, dried over $MgSO_4$, filtered and evaporated to give a residue which is adsorbed onto silica and eluted through a column of flash silica with hexane:EtOAc (4:1 to 2:1) to give the desired product.

ESI MS: m/z (rel intensity) 474.1 (100, $M+H^+$).

b. The methyl ester 14a (260 mg, 0.55 mmol) is hydrolyzed to its relative carboxylic acid as described for example 1b. The solid residue is recrystallized from EtOAc:hexane to give the desired product.

ESI MS: m/z (rel intensity) 477.1 (66, $M+NH_4^+$), 460.1 (100, $M+H^+$).

Example 15

2-(4-Phenylazobenzenesulfonyl)-amino-5-phenylpentynoic acid a. Methyl 2-(4-Phenylazobenzenesulfonyl)-amino-5-phenylpentynoate: The starting t-butyl-carbamate 1c (500 mg, 2.09 mmol) is converted to the title sulfonamide upon treatment with 4-phenylazobenzene sulfonyl chloride (700 mg, 2.5 mmol) as described for example 1a. The crude residue is adsorbed onto silica and then eluted through a column of flash silica with Hexanes:$Et_2O$ (7:3 to 2:3) to give a yellow gum which solidified upon standing.

ESI MS: m/z (rel intensity) 465.3 (16, M+Na), 448.3 (100, $M+H^+$).

b. The methyl ester 15a (0.46 g, 1.04 mmol) is treated with LiOH (132 mg, 3.1 mmol, in 10 mL of THF:$H_2O$ (1:1) and stirred for 17 hr at room temperature. The solution is acidified to pH 2–3 with 1N HCl, then extracted with EtOAc. The organic layer is washed with brine, dried over $MgSO_4$, filtered and evaporated. The solid residue is recrystallized from EtOAc:Hexanes (1:2) to give the title compound as an orange solid.

ESI MS: m/z (rel intensity) 451.3 (21, $M+NH_4^+$), 434.2 (100, $M+H^+$).

Example 16
Preparation of 2-{[4'-Phenyloxy(1,1'-biphenyl)-4-yl]-sulfonyl}-amino-5-(pyridin-3-yl)-pent-4-ynoic acid The starting Methyl 2-N-boc-amino-5-(pyridin-3-yl)-pent-4-ynoate 16a (prepared as described in *Tetrahedron Lett.*, 1994, 35, 3669), is converted to the title compound as described for example 9.

Example 17
Preparation of 2-[4-(4-Methoxyphenyl)-acetylenylbenzenesulfonyl]-amino-5-(pyridin-3-yl)-pent-4-ynoic acid The starting Methyl 2-N-boc-amino-5-(pyridin-3-yl)-pent-4-ynoate 16a is converted to the title compound as described for example 14.

Example 18
Preparation of 2-{[4'-Methoxy-(1,1'-biphenyl)-4-yl]-sulfonyl}-amino-5-(pyridin-3-yl)-pent-4-ynoic acid The starting Methyl 2-N-boc-amino-5-(pyridin-3-yl)-pent-4-ynoate 16a is converted to the title compound as described for example 1.

Example 19
Preparation of 2-{[4'-Methoxy-(1,1'-biphenyl)-4-yl]-sulfonyl)-amino-5-(furan-2-yl)-pent-4-ynoic acid The starting Methyl 2-N-boc-amino-5-(furan-2-yl)-pent-4-ynoate 19a (prepared as described in *Tetrahedron Lett.*, 1994, 35, 3669), is converted to the title compound as described for example 1.

Example 20
Preparation of 2-{[4'-(2-Methoxyethoxy)-(1,1'-biphenyl)-4yl]-sulfonyl}-amino-5-(furan-2-yl)-pent-4-ynoic acid The starting Methyl 2-N-boc-amino-5-(furan-2-yl)-pent-4-ynoate 19a is converted to the title compound as described for example 10.

Example 21
Preparation of 2-{[4'-(2-N-pyrrolidino-ethoxy)-(1,1'-biphenyl)-4-yl]-sulfonyl}-amino-5-(furan-2-yl)-pent-4-ynoic acid The starting Methyl 2-N-boc-amino-5-(furan-2-yl)-pent-4-ynoate 19a is converted to the title compound as described for example 11.

Example 22
Preparation of 2-{[4'-Methoxy-(1,1'-biphenyl)-4-yl]-sulfonyl}-amino-5-(thiophen-2-yl)-pent-4-ynoic acid The starting Methyl 2-N-boc-amino-5-(thiophen-2-yl)-pent-4-ynoate 22a (prepared as described in *Tetrahedron Lett.*, 1994, 35, 3669), is converted to the title compound as described for example 1.

Example 23
Preparation of 2-{[4'-Methoxy-(1,1'-biphenyl)-4-yl]-sulfonyl)-amino-5-(N-methylpyrrol-2-yl)-pent-4-ynoic acid The starting Methyl 2-N-boc-amino-5-(N-methylpyrrol-2-yl)-pent-4-ynoate 19a (prepared as described in *Tetrahedron Lett.*, 1994, 35, 3669), is converted to the title compound as described for example 1.

Example 24
Preparation of 2-(4-n-Butoxybenzene)-sulfonylamino-5-phenylpent-4-ynoic acid The starting tert-butyl-carbamate 1c is deprotected and coupled to n-butoxybenzenesulfonyl chloride as described for compound 1a and then converted to its relative hydroxamic acid as described for compound 1b.

Examples 25–30

The following chemical formula along with Table 2 shows the structure of compounds made according to the description in Examples 25–30 described below:

TABLE 2

| Example | R₁ | R₂ | R₃ |
|---|---|---|---|
| 25 | 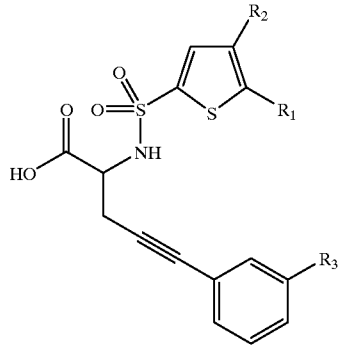 | —H | —H |

TABLE 2-continued

[Structure: central scaffold with HO-C(=O)-CH(NH-SO2-thiophene(R1,R2))-CH2-C≡C-phenyl(R3)]

| Example | R₁ | R₂ | R₃ |
|---------|-----|-----|-----|
| 26 | —C≡C—(4-methoxyphenyl) | —H | —H |
| 27 | —H | —SO₂—phenyl | —H |
| 28 | —SO₂—phenyl | —H | —H |
| 29 | —(4-methoxyphenyl) | —H | —N-morpholine |
| 30 | —(4-methoxyphenyl) | —H | —NMe₂ |

Example 25

Preparation of 2-{5-(4-Methoxyphenyl)-thiophen-2-yl]-sulfonyl}-amino-5-phenylpent-4-ynoic acid:

a. Methyl 2-[(5-bromothiophen-2-yl)-sulfonyl]-amino-5-phenylpent-4-ynoate:

The starting t-butyl-carbamate 1c (3.38 g, 11.2 mmol) is converted to the title sulfonamide upon treatment with 5-bromothiophen-2-yl sulfonyl chloride (4.05 g, 13.4 mmol) as described for example 1a. The crude residue is adsorbed onto silica and then eluted through a column of flash silica with Hexanes:Et₂O (7:3 to 2:3) to give 3.9 of yellow gum which solidified upon standing.

ESI MS: m/z (rel intensity) 447.1 (100, M⁺+Na⁺), 445.2 (85, M⁺+Na⁺), 430.1 (45, M+H⁺), 428.1 (42, M+H⁺).

b. Methyl 2-{[5-(4-Methoxyphenyl)-thiophen-2-yl]-sulfonyl}-amino-5-phenylpent-4-ynoate: The starting sulfonamide 25a (430 mg, 1.0 mmol) and 4-methoxyphenylboronic acid (230 mg, 1.5 mmol) is taken in 15 mL of benzene, 0.5 mL of EtOH and 1 mL of water and treated with Pd(PPh₃)₄ (35 mg, 0.03 mmol) and Na₂CO₃ (0.21 g, 2 mmol). The mixture is brought to a mild reflux for 18 hr and then partitioned between EtOAc and 1N HCl. The organic layer is washed with brine, dried over MgSO₄, filtered and evaporated. The residue is recrystallized from hexanes:EtOAc (7:3) to give 270 mg of off-white solid.

ESI MS: m/z (rel intensity) 473 (100, M+NH₄⁺), 456 (75, M+H⁺).

c. The methyl ester 25b (237 mg, 0.5 mmol) is hydrolyzed to its relative carboxylic acid as described for example 1b.

The solid residue is recrystallized from EtOAc:hexane to give 130 mg of desired product.

ESI MS: m/z (rel intensity) 459 (100, M+NH$_4^+$), 442 (94, M+H$^+$).

Example 26
Preparation of 2-{[5-(4methoxyphenylacetylenyl)-thiophen-2-yl]-sulfonyl}-amino-5-phenylpent-4-ynoic acid a. Methyl 2-{[5-(4-methoxyphenylacetylenyl)-thiophen-2-yl]-sulfonyl}-amino-5-phenyl-pent-4-ynoate: The starting bromo thiophene sulfonamide 25a (0.47 g, 1.1 mmol) and 4-methoxyphenylacetylene (0.19 g, 1.42 mmol) are taken in 10 mL of DMF in the presence of 0.31 mL of Et$_3$N, Pd(PPh$_3$)$_2$Cl$_2$ (38.6 mg, 0.055 mmol), and CuI (21 mg, 0.11 mmol). The mixture is then heated to 55° C. for 18 hr. and then partitioned between EtOAc and H$_2$O. The organic layer is washed with 1N HCl, aqueous NaHCO$_3$ and brine, dried over MgSO$_4$, filtered and evaporated to give a red residue which is adsorbed onto silica and eluted through a column of flash silica with hexanes:EtOAc (4:1) to give 0.21 g of pale yellow solid.

ESI MS: m/z (rel intensity) 497.1 (28, M+NH$_4^+$), 480.3 (100, M+H$^+$).

b. The methyl ester 26a (110 mg, 0.23 mmol) is hydrolyzed to its relative carboxylic acid as described for example 1b. The solid residue is recrystallized from EtOAc:hexane to give 80 mg of white crystals.

ESI MS: m/z (rel intensity) 483.3 (16, M+NH$_4^+$), 466.2 (100, M+H$^+$).

Example 27
Preparation of 2-{[(4benzenesulphonyl)-thiophen-2-yl]-sulfonyl}-amino-5-phenylpent-4-ynoic acid:

a. Methyl 2-{[(4-benzenesulphonyl)-thiophen-2-yl]-sulphonyl}-amino-5-phenylpentynoate: The starting t-butyl-carbamate 1c (0.276 mg, 1.16 mmol) is converted to the title sulfonamide upon treatment with 2-{[(4-benzenesulphonyl)-thiophen-2-yl]-sulphonyl} chloride (340 mg, 1.05 mmol) as described for example 1a.

ESI MS: m/z (rel intensity) 507 (46, M+NH$_4^+$), 490 (100, M+H$^+$).

b. The methyl ester 27a (0.15 g, 0.30 mmol) is treated with NaOH (61 mg, 1.5 mmol) in 3 mL of methanol and 5 ml of water, and stirred for 17 h at room temperature. The solution is acidified to pH 2–3 with 1N HCl, then extracted with EtOAc. The organic layer is washed with brine, dried over MgSO$_4$, filtered and evaporated. The solid residue is recrystallized from EtOAc/Hexanes (1:4) to give the desired product.

ESI MS: m/z (rel intensity) 493 (100, M+NH$_4^+$), 476 (12, M+H$^+$).

Example 28
Preparation of 2-{[(5-benzenesulphonyl)-thiophen-2-yl]-sulphonyl}-amino-5-phenylpent-4-ynoic acid a. Methyl 2-{[(5-benzenesulphonyl)-thiophen-2-yl]-sulphonyl}-amino-5-phenylpentynoate: The starting t-butyl-carbamate 1c (0.42 g, 1.75 mmol) is converted to the title sulfonamide upon treatment with 2-{[(5-benzenesulphonyl)-thiophen-2-yl]-sulphonyl} chloride (620 mg, 1.93 mmol as described for example 1a.

ESI MS: m/z (rel intensity) 507 (75, M+NH$_4^+$), 490 (100, M+H$^+$).

b. The methyl ester 28a (0.185 g, 0.39 mmol) is converted to the title acid as described for compound 27b.

ESI MS: m/z (rel intensity) 493 (86, M+NH$_4^+$), 476 (100, M+H$^+$).

Example 29
Preparation of 2-{[5-(4-Methoxyphenyl)-thiophen-2-yl]-sulfonyl}-amino-5-(3-N-morpholino)-phenylpent-4-ynoic acid The methyl ester 5a is converted to the title compound as described for example 25.

Example 30
Preparation of 2-{[5-(4-Methoxyphenyl)-thiophen-2-yl]-sulfonyl}-amino-5-(3-N,N-dimethylamino)-phenylpent-4-ynoic acid The dimethylamino-analog of methyl ester 5a is prepared as described for compound 5a and then converted to the title compound as described for example 25.

Examples 31–58

The following chemical formula along with Table 3 shows the structure of compounds made according to the description in Examples 31–58 described below:

TABLE 3

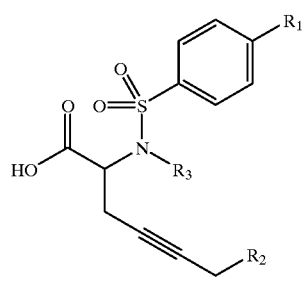

| Example | R$_1$ | R$_2$ | R$_3$ |
|---|---|---|---|
| 31 | 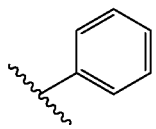 | 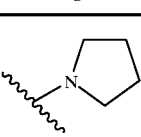 | —H |

TABLE 3-continued

| Example | R₁ | R₂ | R₃ |
|---------|----|----|----|
| 32 | 4-MeO-phenyl | pyrrolidin-1-yl | —H |
| 33 | phenyl | morpholin-4-yl | —H |
| 34 | 4-MeO-phenyl | morpholin-4-yl | —H |
| 35 | 4-MeS-phenyl | morpholin-4-yl | —H |
| 36 | 4-MeO-phenyl-ethynyl | morpholin-4-yl | —H |
| 37 | 4-PhO-phenyl | morpholin-4-yl | —H |
| 38 | 4-MeO-phenyl | 4-phenylpiperazin-1-yl | —H |

TABLE 3-continued

| Example | R₁ | R₂ | R₃ |
|---------|----|----|----|
| 39 | 4-OMe-C₆H₄- | 4-(Boc)piperazin-1-yl | —H |
| 40 | 4-OMe-C₆H₄- | 4-(methanesulfonyl)piperazin-1-yl | —H |
| 41 | 4-OMe-C₆H₄- | 4-acetylpiperazin-1-yl | —H |
| 42 | 4-OPh-C₆H₄- | pyrrolidin-1-yl | —H |
| 43 | 4-OPh-C₆H₄- | N(CH₃)₂ | —H |
| 44 | 4-MeO-C₆H₄-C(O)NH- | morpholin-4-yl | —H |
| 45 | 4-(n-BuO)-C₆H₄-C(O)NH- | morpholin-4-yl | —H |

TABLE 3-continued

| Example | R₁ | R₂ | R₃ |
|---|---|---|---|
| 46 | 4-MeO-C₆H₄- | phenyl | —H |
| 47 | 4-(2-methoxyethoxy)-C₆H₄- | phenyl | —H |
| 48 | 4-(2-(pyrrolidin-1-yl)ethoxy)-C₆H₄- | phenyl | —H |
| 49 | 4-MeO-C₆H₄- | phenoxy | —H |
| 50 | 4-MeO-C₆H₄- | methoxy | —H |
| 51 | 4-Br-C₆H₄- | methoxy | —H |
| 52 | 4-MeO-C₆H₄- | methoxy | —Me |
| 53 | 4-MeO-C₆H₄- | —O-CH₂-O-CH₂CH₂-O-Me | —H |

TABLE 3-continued

[Structure: sulfonamide with R1-phenyl-SO2-N(R3)-CH(COOH)-CH2-C≡C-CH2-R2]

| Example | R₁ | R₂ | R₃ |
|---|---|---|---|
| 54 | 4-Br-phenyl | -O-phenyl | —H |
| 55 | 4-OPh-phenyl | -OMe | —H |
| 56 | 4-OMe-phenyl | -S-phenyl | —H |
| 57 | 4-OMe-phenyl | -S-(cyclopentadienyl-phenyl) | —H |
| 58 | 4-OMe-phenyl | -S-(5-pyrrolidinyl-1,3,4-thiadiazol-2-yl) | —H |

Example 31

Preparation of 2-[(1,1'-Biphenyl-4-yl)-sulfonyl]-amino-6-pyrrolidinohex-4-ynoic acid a. Methyl tert-butoxycarbonylamino-6-pyrrolidinohex-4-ynoate: Pyrrolidine (936 mL, 11.2 mmol) is taken in 6 mL of dioxane and treated with paraformaldehyde (337 mg, 11.2 mmol wrt. monomer) and the resulting mixture is allowed to stir for 30 min. The free acetylene 4e (1.7 g, 7.49 mmol) is separately dissolved in dioxane and added to the previous solution, treated with Cu(acac)₂ (392 mg, 1.5 mmol), heated to 90° C. for 3 hr., and partitioned between EtOAc and dil. Na₂CO₃. The organic layer is washed with brine, dried over MgSO₄, filtered and evaporated. The crude residue is then adsorbed onto silica and eluted through a column of flash silica with EtOAc:MeOH (1:0 to 5:1) to give a pale yellow syrup.

ESI MS: m/z (rel intensity) 31 1.1 (100, M+H⁺), 255.0 (65), 211.0 (10).

b. Methyl 2-(4-iodophenylsulfonyl)-amino-6-pyrrolidinohex-4-ynoate: The starting t-butyl-carbamate 31a (1.04 g, 3.35 mmol) is taken in 15 mL of MeOH and treated with 2 mL of SOCl₂. The resulting mixture is stirred for 30 min. and evaporated to dryness. The residue is then taken in CH₂Cl₂ and 3 mL of Et₃N and treated with pipsyl chloride (1.32 g, 4.36 mmol) and the mixture is stirred for 18 hr. and then partitioned between CHCl₃ and dil. Na₂CO₃. The organic layer is dried over MgSO₄, filtered and evaporated and the crude product is adsorbed onto silica and eluted through flash silica with EtOAc:MeOH (1:0 to 2:1) to give the title compound 31b as well as unsulfonylated free amine 31c.

31b: ESI MS: m/z (rel intensity) 476.9 (100, M+H⁺), 211.1 (20).

31c: ESI MS: m/z (rel intensity) 211.1 (100, M+H⁺), 102.1 (100).

d. Methyl 2-[(1,1'-Biphenyl-4-yl)-sulfonyl]-amino-6-pyrrolidinohex-4-ynoate:

The free amine 31c (132 mg, 0.628 mmol) and biphenylsulfonyl chloride (190 mg, 0.754 mmol) is taken in 3 mL of CHCl₃ in the presence of 0.5 mL of Et₃N and stirred for 18 hr. It is then partitioned between $CHCl_3$ and dil. $CHCl_3$. The organic layer is dried over $MgSO_4$, filtered and evaporated. The residue is adsorbed onto silica and eluted through a column of flash silica with EtOAc:MeOH (1:0 to 5:1) to give a pale yellow syrup.

ESI MS: m/z (rel intensity) 457.0 (7, M+H$^+$).

e. The methyl ester 31d (105 mg, 0.25 mmol) is taken in 10 mL of MeOH:$H_2O$ (10:1) and treated with KOH (115 mg, 2.05 mmol). The resulting mixture is stirred for 18 hr., evaporated to dryness and partitioned between sat. $NaH_2PO_4$ and $CHCl_3$:MeOH (15:1). The layers are separated and the aqueous layer similarly twice extracted. Combined organic layers are dried over $MgSO_4$, filtered and evaporated. The crude pale orange residue is then recrystallized from MeOH:EtOAc (4:1) to give an off-white solid.

ESI MS: m/z (rel intensity) 443.0 (100, M+H$^+$).

Example 32

Preparation of 2-{[4'-Methoxy(1,1'-biphenyl)-4-yl]-sulfonyl}-amino-6-pyrrolidinohex-4-ynoic acid a. Methyl 2-{[4'-Methoxy(1,1'-biphenyl)-4-yl]-sulfonyl}-amino-6-pyrrolidinohex-4-ynoate: The starting sulfonamide 31b (403 mg, 0.847 mmol) and 4-methoxyphenylboronic acid (193 mg, 1.27 mmol) are taken in 10 mL of benzene, 1.5 mL of EtOH and 1.5 mL of water in the presence of Pd(PPh$_3$)$_4$ (29 mg, 0.025 mmol) and 200 mg of $Na_2CO_3$ and brought to reflux for 18 hr. The mixture is then partitioned between EtOAc and dil. $Na_2CO_3$. The organic layer is washed with brine, dried over $MgSO_4$, filtered and evaporated. The crude product is adsorbed onto silica and eluted through flash silica with EtOAc:MeOH (1:0 to 4:1) to give a pale orange tar.

ESI MS: m/z (rel intensity) 457.0 (100, M+H$^+$).

b. The methyl ester 32a (201 mg, 0.44 mmol) is saponified as described for compound 31e. The crude pale orange residue is then recrystallized from MeOH:EtOAc (4:1) to give a pale orange solid.

ESI MS: m/z (rel intensity) 443. (100, M+H$^+$).

Example 33

Preparation of 2-[(1,1'-Biphenyl)-4yl-sulfonyl]-amino-6-morpholinohex-4-ynoic acid a. Methyl 2-N-tert-butoxycarbonylamino-6-morpholinohex-4-ynoate: Morpholine (3.23 mL, 37.1 mmol) is coupled with paraformaldehyde (1.12 mg, 37.1 mmol wrt monomer) and free acetylene 4e (5.62 g, 24.8 mmol) as described for compound 31a to give the title compound as a pale yellow syrup.

ESI MS: m/z (rel intensity) 327.1 (85, M+H$^+$), 227.1 (100).

b. Methyl 2-[(1,1'-biphenyl)-4-yl-sulfonyl]-amino-6-morpholinhex-4-ynoate: The starting t-butyl-carbamate 33a (614 mg, 1.39 mmol) is deprotected and coupled with biphenylsulfonyl chloride (702 mg, 2.78 mmol) as described for compound 31b to give the title compound as a pale yellow tar.

ESI MS: m/z (rel intensity) 476.9 (100, M+H$^+$), 211.1 (20).

c. The methyl ester 33b (252 mg, 0.57 mmol) is hydrolyzed as described for compound 31e to give the title compound.

ESI MS: m/z (rel intensity) 429.0 (100, M+H$^+$).

Example 34

Preparation of 2-{[4'-Methoxy-(1,1'-biphenyl)-4-yl]-sulfonyl}-amino-6-morpholinohex-4-ynoic acid a. Methyl 2-(4-iodophenylsulfonyl)-amino-6-morpholinohex-4-ynoate: The starting t-butyl-carbamate 31a (6.10 g, 18.7 mmol) is deprotected and coupled with pipsyl chloride (5.11 g, 16.84 mmol) as described for compound 31b to give the title compound as a pale yellow tar.

ESI MS: m/z (rel intensity) 492.9 (100, M+H$^+$).

b. Methyl 2-{[4'-methoxy-(1,1'-biphenyl)-4-yl]-sulfonyl}-amino-6-morpholinohex-4-ynoate: The starting sulfonamide 34a (500 mg, 1.02 mmol) is coupled to 4-methoxyphenyl-boronic acid (233 mg, 1.53 mmol) as described for compound 32a to give the title compound as a light brown solid.

ESI MS: m/z (rel intensity) 473.0 (100, M+H$^+$).

c. The methyl ester 34b (36 mg, 0.076 mmol) is hydrolyzed as described for compound 31e to give the title compound as a yellow solid.

ESI MS: m/z (rel intensity) 459.1 (100, M+H$^+$).

Example 35

Preparation of 2-{[4'-Methylthio-(1,1'-biphenyl)-4-yl]-sulfonyl}-amino-6-morpholinohex-4-ynoic acid a. Methyl 2-{[4'-Methylthio-(1,1'-biphenyl)-4-yl]-sulfonyl}-amino-6-morpholinohex-4-ynoate: The starting sulfonamide 34a (500 mg, 1.02 mmol) is coupled to 4-methylthiophenyl-boronic acid (257 mg, 1.53 mmol) as described for compound 32a to give the title compound as a light orange solid.

ESI MS: m/z (rel intensity) 489.0 (100, M+H$^+$).

b. The methyl ester 35a (40 mg, 0.081 mmol) is hydrolyzed as described for compound 31e to give 16 mg of the title compound as a yellow solid.

ESI MS: m/z (rel intensity) 475.0 (100, M+H$^+$).

Example 36

Preparation of 2-[4-(4-Methoxyphenyl)-acetylenylbenzenesulfonyl]-amino-6-morpholinohex-4-ynoic acid a. Methyl 2-[4-(4-Methoxyphenyl)-acetylenylbenzenesulfonyl]-amino-6-morpholinohex-4-ynoate: The starting sulfonamide 31b (1.00 g, 2.03 mmol) and 4-methoxyphenylacetylene (350 mg, 2.64 mmol) are taken in 20 mL of DMF, in the presence of Pd(PPh$_3$)$_2$Cl$_2$ (72 mg, 0.102 mmol), CuI (40 mg, 0.20 mmol) and Et3N (0.565 mL, 4.06 mmol) and stirred at 55° C. for 16 hr. The mixture is then diluted in EtOAc and washed three times with dil. $Na_2CO_3$, one time with brine, dried over $MgSO_4$, filtered and concentrated. The crude product is adsorbed onto silica and eluted through flash silica with EtOAc:hexanes (1:1 to 1:0) to give a pale orange tar.

ESI MS: m/z (rel intensity) 497.4 (100, M+H$^+$).

b. The methyl ester 36a (920 mg, 1.85 mmol) is hydrolyzed as described for compound 30e to give the title compound as a solid.

ESI MS: m/z (rel intensity) 521.0 (100, M+K$^+$).

Example 37

Preparation of 2-{[4'-Phenyloxy-(1,1'-biphenyl)-4-yl]-sulfonyl}-amino-6-morpholinohex-4-ynoic acid The sulphonyl chloride 9g is coupled with t-butyl-carbamate 33a as described for compound 31b and the resulting sulfonamide is hydrolyzed as described for compound 31e to give the title compound.

Example 38

Preparation of 2-{[4'-Methoxy-(1,1'-biphenyl)-4-yl]-sulfonyl}-amino-6-(4N-phenylpiperazin-1N-yl)-hex-4-ynoic acid a. Methyl 2-{[4'-methoxy-(1,1'-biphenyl)-4-yl]-sulfonyl}-amino-pent-4-ynoate: (±)-Propargyl glycene (2.15 g, 18.9 mmole) is taken in 50 mL of MeOH and treated with 3 mL of $SOCl_2$. The resulting mixture is stirred at RT for 16 hr and the evaporated to dryness. The resulting residue is dissolved in 40 mL of $CHCl_3$, 20 mL of DMF and 25 mL of $NEt_3$, treated with 4-methoxybiphenylsulfonyl chloride and stirred for 16 hr at RT. It is then partitioned between 5% $NaHCO_3$ and Hexanes:EtOAc (1:3). The organic layer is washed 2x with 5% NaHCO3, 1x with brine, dried over MgSO4, filtered and evaporated to give a yellowish-brown solid which is recrystallized from i-PrOH:Hex to give a tan solid.

b. Methyl 2-{[4'-methoxy-(1,1'-biphenyl)-4-yl]-sulfonyl}-amino-6-(4N-phenylpiperazin-1N-yl)-hex-4-ynoate: N-Phenyl-1,4-piperazine (478 mg, 2.95 mmol) is coupled with paraformaldehyde (96 mg, 3.21 mmol wrt. monomer) and free acetylene 38e (1.0 g, 2.68 mmole) as described for compound 31a to give the title compound as a white solid.

ESI MS: m/z (rel intensity) 548.2 (100, M+H$^+$).

c. 2-{[4'-Methoxy-(1,1'-biphenyl)-4-yl]-sulfonyl}-amino-6-(4N-phenylpiperazin-1N-yl)-hex-4-ynoic acid: The methyl ester 38a is hydrolyzed to give the title acid as described for compound 31e.

ESI MS: m/z (rel intensity) 556.1 (25, M+Na$^+$), 534.1 (100, M+H$^+$).

Example 39

Preparation of 2-{[4'-Methoxy-(1,1'-biphenyl)-4-yl]-sulfonyl}-amino-6-(4N-tert-butoxycarbonylpiperazin-1N-yl)-hex-4-ynoic acid a. Methyl 2-{[4'-methoxy-(1,1'-biphenyl)-4-yl]-sulfonyl}-amino-6-(4N-tert-butylcarbonylpiperazin-1N-yl)-hex-4ynoate: N-tert-butoxycarbonyl-1,4-piperazine (8.14 g, 4.37 mmol) is coupled with paraformaldehyde (143 mg, 4.7 mmol wrt. monomer) and free acetylene 38e (1.48 g, 3.97 mmol) as described for compound 31a to give the title compound as a pale yellow syrup which soildified upon standing.

ESI MS: m/z (rel intensity) 572.2 (100, M+H$^+$).

b. 2-{[4'-Methoxy-(1,1'-biphenyl)-4-yl]-sulfonyl}-amino-6-(4N-tert-butoxy-carbonylpiperazin-1N-yl)-hex-4-ynoic acid: The methyl ester 39a is hydrolyzed to give the title acid as described for compound 31e.

ESI MS: m/z (rel intensity) 558.2 (100, M+H$^+$).

Example 40

Preparation of 2-{[4'-Methoxy-(1,1'-biphenyl)-4-yl]-sulfonyl}-amino-6-(4N-methanesulfonylpiperazin-1N-yl)-hex-4ynoic acid a. Methyl 2-{[4'-methoxy-(1,1'-biphenyl)-4-yl]-sulfonyl}-amino-6-(4N-methane sulfonylpiperazin-1N-yl)-hex-4-ynoate: The protected piperazine 31a (213 mg, 0.37 mmole) is taken in 25 mL of $CH_2Cl_2$ and treated with 4 mL of trifluoroacetic acid at RT. The resulting mixture is stirred for 3 Hr and then evaporated to dryness and triturated with $CHCl_3$. The residue is dissolved in 25 mL of $CH_2Cl_2$ and treated with 3 mL of $NEt_3$ and then methanesulfonyl chloride (0.032 mL, 0.41 mmole). The resulting mixture is stirred for 3 hr and then partitioned between 5% $NaHCO_3$ and EtOAc. The organic layer is washed with brine, dried over $MgSO_4$, filtered and evaporated to give an off-white solid which is purified via flash chromatography with EtOAc to give a white solid.

ESI MS: m/z (rel intensity) 550.0 (100, M+H$^+$).

b. 2-{[4'-Methoxy-(1,1'-biphenyl)-4-yl]-sulfonyl}-amino-6-(4N-tert-butoxycarbonylpiperazin-1N-yl)-hex-4-ynoic acid: The methyl ester 40a is hydrolyzed to give the title acid as described for compound 31e.

ESI MS: m/z (rel intensity) 536.0 (100, M+H$^+$).

Example 41

Preparation of 2-{[4'-Methoxy-(1,1'-biphenyl)-4-yl]-sulfonyl}-amino-6-(4N-acetylpiperazin-1N-yl)-hex-4-ynoic acid a. Methyl 2-{[4'-methoxy-(1,1'-biphenyl)-4-yl]-sulfonyl}-amino-6-(4N-methane sulfonylpiperazin-1N-yl)-hex-4-ynoate: The protected piperazine 31a (210 mg, 0.37 mmole) is deprotected and converted to an acetate derivative upon treatment with acetic anhydride as described for compound 40a.

ESI MS: m/z (rel intensity) 514.1 (85, M+H$^+$).

b. 2-{[4'-Methoxy-(1,1'-biphenyl)-4-yl]-sulfonyl}-amino-6-(4N-tert-butoxycarbonylpiperazin-1N-yl)-hex-4-ynoic acid: The methyl ester 40a is hydrolyzed to give the title acid as described for compound 31e.

ESI MS: m/z (rel intensity) 500.1 (85, M+H$^+$).

Example 42

Preparation of 2-{[4'-Phenyloxy-(1,1'-biphenyl)-4-yl]-sulfonyl}-amino-6-pyrrolidinohex-4-ynoic acid The sulphonyl chloride 9g is coupled with t-butyl-carbamate 31a as described for compound 31b and the resulting sulfonamide is hydrolyzed as described for compound 31c to give the title compound.

Example 43

Preparation of 2-{[4'-Phenyloxy-(1,1'-biphenyl)-4-yl]-sulfonyl)-amino-6-(N,N-dimethylamino)-hex-4-ynoic acid a. Methyl tert-butoxycarbonylamino-6-(N,N-dimethylamino)-hex-4-ynoate: Dimethylamine is couplked with paraformaldehyde and free acetylene 4e as described for compound 30a to give the title compound.

b. The sulphonyl chloride 9g is coupled with t-butyl-carbamate 43a as described for compound 31b and the resulting sulfonamide is hydrolyzed as described for compound 31e to give the title compound.

Example 44

Preparation of 2-[4-(N-4-Methoxybenzoyl)-aminobenzenesulfonyl]-amino-6-morpholinohex-4-ynoic acid a. Methyl 2-(4-acetamidobenzenesulfonyl)-amino-6-morpholinohex-4-ynoate: The t-butylcarbamate 33a is deprotected and coupled to 4-acetamidobenzenesulfonyl chloride as described for compound 31b to give the title compound.

b. Methyl 2-[4-(N-4-methoxybenzoyl)-aminobenzenesulfonyl]-amino-6-morpholinohex-4-ynoate: The acetamide 44a is heated to reflux for 3h in 3N HCl and then concentrated to dryness and azeotroped with toluene. The resulting residue is dissolved in $CH_3OH$, followed by slow addition of thionyl chloride. The mixture is stirred for 18h, and solvent is removed under reduced pressure. The crude aniline sulfonamide intermediate is dissolved in $CH_2Cl_2$, cooled to 0° C. 4-Methylmorpholine is added, followed by 4-Methoxybenzoyl chloride. The reaction mixture is stirred for 18h, diluted with water, and extracted three times with EtOAc. The combined EtOAc layers are washed with dil $Na_2CO_3$, $H_2O$, brine, dried over $MgSO_4$, and concentrated to a solid which is eluted through flash silica with EtOAc to give the title compound.

ESI MS: m/z (rel intensity) 516.1 (100, M+H$^+$).

c. The methyl ester 44b is hydrolyzed as described for compound 31e to give the title compound as a solid.

ESI MS: m/z (rel intensity) 524.1 (25, M+Na$^+$), 502.1 (100, M+H$^+$).

Example 45
Preparation of 2-[4-(N-4-n-Butoxybenzoyl)-aminobenzenesulfonyl]-amino-6-morpholinohex-4-ynoic acid a. Methyl 2-[4-(N-4-n-Butoxybenzoyl)-aminobenzenesulfonyl]-amino-6-morpholinohex-4-ynoate: The acetamide 44a is converted to the title compound upon coulping with n-butoxybenzene as described for compound 44b.

b. The methyl ester 45a is hydrolyzed as described for compound 31e to give the title compound as a solid.

Example 46
Preparation of 2-{[4'-Methoxy-(1,1'-biphenyl)-4-yl]-sulfonyl}-amino-6-phenylhex-4-ynoic acid a. Butyl-2-hydroxy-6-phenylhex-4-ynylether: The starting 3-phenyl-1-propyne (2.71 g, 23.4 mmole) is taken in 100 mL of dry THF under argon and cooled to −78° C. A solution of n-butyl lithium (9.36 mL, 23.4 mmole) is added dropwise and the mixture is allowed to stir for 15 min. afterwhicb $BF_3OEt_2$ (2.91 mL, 23.4 mmole) is added dropwise and the solution allowed to stir for 15 min. Tert-Butyl glycidyl ether (3.01 mL, 21.2 mmole) is then added dropwise. The mixture is allowed to stir for 15 min. and then the cooliung bath is removed and the solution allowed to come to room temperature for 1 hr. The reaction is quenched with sat. $NH_4Cl$ and then partitioned between water and EtOAc. The organic layer is washed with brine, dried over $MgSO_4$, filtered and evaporated to give a crude syrup which is adsorbed onto silica, eluted through a flash silica column with hexanes:EtOAc (10:1 to 2:1) to give the title ether as a clear syrup.

b. tert-Butyl-2-methanesulfonyloxy-6-Phenylhex-4-ynylether: The starting alcohol 46a (2.61 g, 10.6 mmole) is taken in 100 mL of $CH_2Cl_2$ in the presence of 2 mL of $Et_3N$ and treated with methanesulfonyl chloride (1.64 mL, 21.2 mmole) and allowed to stir for 18 hr. The mixture is then partitioned $CHCl_3$ and 1N HCl. The organic layer is dried over $MgSO_4$, filtered and evaporated. The crude material is adsorbed onto silica and eluted through flash silica with hexanes:EtOAc (10:1 to 2:1) to give the desired material as a pale yellow syrup.

c. 1-hydroxy-2-azido-6-Phenylhex-4-yn: The methane sulfonate 46b (1.05 g, 3.24 mmole) is taken in 25 mL of $CH_2Cl_2$ and treated with 2 mL of trifluoroacetic acid and the resulting dark brown solution wis allowed to stir for 2 hr. The mixture is diluted with $CH_2Cl_2$, washed with dil. $NaHCO_3$, dried over $MgSO_4$, filtered and evaporated. The residue is taken in 10 mL of DMF, treated with 1 g of $NaN_3$ and heated to 65° C. for 18 hrs. The mixture is the diluted with hexanes:EtOAc (1:2) and washed 3x with water, 1x with brine, dried over $MgSO_4$, filtered and evaporated. The brown residue is adsorbed onto silica and eluted through a column of flash silica with hexanes:EtOAc (4:1 to 1:3) to give the title compound as a tan gum.

d. 1-Hydroxy-2-(4-bromobenzenesulfonyl)-amino-6-phenylhex-4-yn: The azide 46e (443 mg, 2.06 mmole) is taken in 5 mL of THF in the presence of $PPh_3$ (1.08 g, 4.12 mmole) and treated with a 0.3 mL of water. The mixture is stirred for 18 hr, diluted with 10 mL of dioxane, 1 mL of $H_2O$ and 2.5 mL of $Et_3N$ and then treated with 4-bromobenzenesulfonyl chloride. The mixture is stirred for 2 hr and then partitioned between EtOAc and 1N HCl. The organic layer is washed with brine, dried over $MgSO_4$, filtered and evaporated. The tan resigue is then adsorbed onto silica and eluted through a column of flesh silica with hexanes:EtOAc (4:1 to 1:4) to give the title compound as a pale yellow solid.

e. 1-Hydroxy-2-{[4'-methoxy-(1,1'-biphenyl)-4-yl]-sulfonyl}-amino-6-phenylhex-4-yn: The bromide 46d (330 mg, 0.81 mmole) is taken in 10 mL of benzene in the presence of 4-methoxybenzene boronic acid, palladium tetrakistriphenylphosphine (50 mg), $Na_2CO_3$ (150 mg), 1 mL of water and 1 mL of EtOH. The mixture is brought to reflux for 18 hr and then partitioned between water and hexanes:EtOAc (1:2). The organic layer is washed with brine, dried over $MgSO_4$, filtered and evaporated to give a residue which is adsorbed onto silica and eluted through flash silica with hexanes:EtOAc (2:1 to 1:3) to give the title compound as a pale yellow oil.

f. The alcohol 46e (159 mg, 0.36 mmole) is taken in 100 mL of acetone and treated dropwise with Jones reagent until an orange color persists. The mixture is stirred for 50 min. and then quenched with excess isopropyl alcohol and stirred for an additional 30 min. The fine green precipitate is filtered and the solvent evaporated. The residue eluted through a short column of flash silica with $CHCl_3$:MeOH (1:0 to 5:1) to give the title compound as an off-white solid.

Example 47
Preparation of 2-{[4'-(2-Methoxyethoxy)-(1,1'-biphenyl)-4-yl]-sulfonyl}-amino-6-phenylhex-4-ynoic acid a. 1-Hydroxy-2-{[4'-(2-methoxyethoxy)-(1,1'-biphenyl)-4-yl]-sulfonyl}-amino-6-phenylhex-4-yn: The azide 46c is coupled to sulfonyl chloride 10a is as described for compound 46d to give the title compound.

b. The alcohol 47a is oxidized to the title acid as described for compound 46f.

Example 48
Preparation of 2-{[4'-(2-N-Pyrrolidino-ethoxy)-(1,1'-biphenyl)-4-yl]-sulfonyl}-amino-6-phenylhex-4-ynoic acid a. 1-Hydroxy-2-{[4-(2-N-pyrrolidono-ethoxy)-(1,1'-biphenyl)-4-yl]-sulfonyl}-amino-6-phenylhex-4-yn: The azide 46c is coupled to sulfonyl chloride 11a is as described for compound 46d to give the title compound.

b. The alcohol 48a is oxidized to the title acid as described for compound 46f.

Example 49
Preparation of 2-{[4'-Methoxy-(1,1'-biphenyl)-4-yl]-sulfonyl}-amino-6-phenyloxyhex-4-ynoic acid a. tert-Butyl-2-hydroxy-6-phenyloxyhex-4-ynylether: The starting 3-phenyloxy-1-propyne is coupled with tert-Butyl glycidyl ether as described for compound 46a.

b. The title acid is prepared from compound 49a according to the sequence reactions described for compounds 46b–f

Example 50
Preparation of 2-{[4'-Methoxy-(1,1-'biphenyl)-4yl]-sulfonyl}-amino-6-methoxyhex-4-ynoic acid a. tert-Butyl-2-hydroxy-6-methoxyhex-4-ynylether: The starting 3-methoxy-1-propyne is coupled with tert-Butyl glycidyl ether as described for compound 46a.

b. 1-Hydroxy-2-azido-6-methoxyhex-4-ynylether: The starting ether 50a is carried for to the title azide as described for the sequence of reactions for 46b–c.

c. The title acid is prepared from compound 50b according to the sequence reactions described for compounds 46d–f.

Example 51
Preparation of 2-{[4'-Bromo-(1,1'-biphenyl)-4-yl]-sulfonyl}-amino-6-methoxyhex-4-ynoic acid a. tert-Butyl-2-hydroxy-6-methoxyhex-4-ynylether: The starting methoxy alkyne 50a is converted to its relative 2-azido derivative as described for the sequence of reactions described for compounds 46b–c.

b. 1-Hydroxy-2-{[4'-Bromo-(1,1'-biphenyl)-4-yl]-sulfonyl}-amino-6-phenylhex-4-yn: The azide 51c (2.5 g, 14.7 mmole) is taken in 30 mL of THF in the presence of $PPh_3$ (9.6 g, 37 mmole) and treated with a 5 mL of water. The mixture is partitioned between 1N HCl and hex:EtOAc (1:3). The organic layer is extracted with 1N HCl and the combined aqueous layers are neutralized with solid $NaHCO_3$, diluted with an equal volume of dioxane and treated with [4'-Bromo-(1,1'-biphenyl)-4-yl]-sulfonyl chloride (5.3 g, 16.7 mmole) and the resulting solution stirred 16 hr. and then partitioned between EtOAc and $H_2O$. The organic layer is washed with 1N HCl and then brine, dried over MgSO4, filtered and evaporated. The resulting solid is purified via column chromatography with hexanes:EtOAc (1:1) to give the title compound as a white solid.

b. The title acid is prepared from compound 51b as described for compound 46f

Example 52

Preparation of 2-{[4'-Methoxy-(1,1'-biphenyl)-4-yl]-sulfonyl}-N-methyl-amino-6-methoxyhex-4-ynoic acid a. Methyl 2-{[4'-Methoxy-(1,1'-biphenyl)-4-yl]-sulfonyl}-N-methyl-amino-6-methoxyhex-4-ynoate: The acid 51 (500 mg, 1.23 mmole) is dissolved in 20 mL of MeOH and treated with 8 mL of $SOCl_2$. The resulting mixture is stirred at RT for 18 hr. and then evaporated. The residual solid is dissolved in 10 mL of dimethylacetamide and treated with methyl iodide (0.092 mL, 1.47 mmole) in the presence of 600 mg of $Cs_2CO_3$. The resulting mixture is stirred for 2 hr and then partitioned between EtOAc and $H_2O$. The organic layer is washed with water and then brine, dried over $MgSO_4$, filtered and evaporated to give a yellow oil. The title acid is prepared from compound 52b as described for compound 46f.

Example 53

Preparation of 2-{[4'-Methoxy-(1,1'-biphenyl)-4-yl]-sulfonyl}-amino-6-(2-methoxyethoxy)-methoxyhex-4-ynoic acid a. tert-Butyl 2-hydroxy-6-tert-butyldimethylsiloxyhex-4-ynylether: The starting tert-butyldimethylsilyl-1-propyne (20 g, 133 mmole) is converted to the title ether as described for compound 46a.

b. tert-Butyl 2-methanesulfonyloxy-6-tert-butyldimethylsiloxyhex-4-ynylether: The starting alcohol 46a (34.3 g, 114 mmole) is converted to its relative mesylate as described for compound 46b.

c. tert-Butyl 2-methanesulfonyloxy-6-benzoyloxyhex-4-ynylether: The starting siloxyether (28 g, 74 mmole) is taken in 500 mL of tetrahydrofuran and treated with tetrabutylammonium flouride (96 mL, 96 mmole) and the resulting mixture is stirred at RT for 1 hr. and the partitioned between EtOAc and water. The organic layer is washed with water and then brine, dried over $MgSO_4$ and evaporated. The residue is taken in 100 mL of $CH_2Cl_2$ and 40 mL of pyridine and treated with benzoyl chloride (12 mL, 101 mmole). The resulting mixtuer is stirred at RT for 3 days and then evaporated. The residue is taken in hexane and filtered. The filtrate is taken in bexanes:EtOAc (1:4), washed with water and brine, dried over MgSO4, filtered and evaporated. The residue is purified by chromatography with hexanes:EtOAc (9:1) to give a yellow solid.

d. 2-{[4'-Methoxy-(1,1'-biphenyl)-4-yl]-sulfonyl}-amino-6-benzoyloxyhex-4-ynoic acid: The mesylate 53c (12 g, 32.6 mmole) is carried forward to the title acid as described for the sequence of reactions for 46c–f.

e. 2-{[4'-Methoxy-(1,1'-biphenyl)-4-yl]-sulfonyl}-amino-6-hydroxyhex-4-ynoic acid: The starting acid 53d (3.14 g, 6.36 mmole) is taken in 25 mL of methanol and treated with 1.9 mL of $SOCl_2$. The resulting mixture is stirred 16 hr at RT and then evaporated to dryness. The residue is purified by chromatography with hexanes:EtOAc (7:3 to 1:1) to give the product as a white solid.

f. Methyl 2-{[4'-Methoxy-(1,1'-biphenyl)-4-yl]-sulfonyl}-amino-6-(2-methoxyethoxy)-methoxyhex-4-ynoate: The starting alcohol 53e (419 mg, 1.04 mmole) is taken in 4 mL of $CH_2Cl_2$ in the presence of 0.3 mL of diisopropylethyl amine and treated with methoxyethoxymethyl chloride. The resulting solution is stirred for 16 hr and evaporated. The residue is purified by chromatography with hexanes:EtOAc (4:1 to 1:1) to give the product as a white foam.

g. The starting ester 53f (29 mg, 0.06 mmole) is taken in 70 mL of $THF:H_2O$ (1:1) and treated with LiOH (25 mg, 0.6 mmole). The resulting solution is stirred at RT for 1 hr and then partitioned between 1N HCl and EtOAc. The organic layer is dried over $MgSO_4$, filtered and evaporated to give the title acid as a colorless gum.

ESI MS: m/z (rel intensity) 495.0 (100, $M+NH_4^+$), 476.0 (100, $M-H^+$).

Example 54

Preparation of 2-{[4'-Bromo-(1,1'-biphenyl)-4-yl]-sulfonyl}-amino-6-phenyloxy-4-ynoic acid The starting tert-Butoxy-2-hydroxy-6-phenyloxyhex-4-ynylether 49a is converted to the title acid according to the sequence of reactions described for compound 46b–f.

Example 55

Preparation of 2-{[4'-Phenyloxy-(1,1'-biphenyl)-4-yl]-sulfonyl}-amino-6-methoxyhex-4-ynoic acid a. tert-Butyl 2-hydroxy-6-Methoxyhex-4-ynylether: The starting 3-phenyl-1-propyne is coupled with tert-Butyl glycidyl ether as described for compound 46a.

b. 1-hydroxy-2-azido-6-Methoxyhex-4-yn: The title azide is prepared from compound 55a according to the sequence of reactions described for 46b–c.

c. The azide 55b is decomposed and coupled to sulfonyl chloride 9g according to the procedure described for 46d and the resulting sulfonamide is subsequently oxidized according to the procedure described for 46f.

Example 56

Preparation of 2-{[4'-Methoxy-(1,1'-biphenyl)-4-yl]-sulfonyl}-amino-6-phenylthiohex-4-ynoic acid a. tert-Butyl 2-hydroxy-6-Phenylthiohex-4-ynylether: The starting 3-phenylthio-1-propyne is coupled with tert-Butyl glycidyl ether as described for compound 46a.

b. The title acid is prepared from compound 56a according to the sequence reactions described for compounds 46b–f.

Example 57

Preparation of 2-{[4'-Methoxy-(1,1'-biphenyl)-4-yl]-sulfonyl}-amino-6-[5-(furan-2-yl)-oxadiazol-2-yl]-thiohex-4-ynoic acid a. tert-Butyl 2-hydroxy-6-[5-(furan-2-yl)-oxadiazol-2-yl]-thiohex-4-ynylether: The starting 3-[5-(furan-2-yl)-oxadiazol-2-yl]-thio-1-propyne is coupled with tert-Butyl glycidyl ether as described for compound 46a.

b. The title acid is prepared from compound 57a according to the sequence reactions described for compounds 46b–f.

Example 58

Preparation of 2-{[4'-Methoxy-(1,1'-biphenyl)-4-yl]-sulfonyl}-amino-6-[5-(N-pyrrolidinyl)-thiadiazol-2-yl]-thiohex-4-ynoic acid a. tert-Butyl 2-hydroxy-6-[5-(N-pyrrolidinyl)-thiadiazol-2-yl]-thiohex-4-ynylether: The starting 3-[5-(N-pyrrolidinyl)-thiadiazol-2-yl]-thio-1-propyne is coupled with tert-Butyl glycidyl ether as described for compound 46a. The title acid is prepared from compound 58a according to the sequence reactions described for compounds 46b–f.

Examples 59–62

The following chemical formula along with Table 4 shows the structure of compounds made according to the description in Examples 59–62 described below:

TABLE 4

| Example | R$_1$ | R$_2$ | R$_3$ | R$_4$ |
|---|---|---|---|---|
| 59 | —H | —H | —Ph | —OMe |
| 60 | —CH$_2$OCH$_2$Ph | —H | —H | —OMe |
| 61 | —CH$_2$OCH$_2$Ph | —H | —H | —H |
| 62 | —H | (pyrrolidinyl-C(O)-) | —H | —OMe |

Example 59
Preparation of trans-2-{[4'-Methoxy-(1,1'-biphenyl)-4-yl]-sulfonyl}-amino-5-phenylpent-4-enoic acid a. trans-Methyl 2-(4-Iodophenylsulfonyl)-amino-5-phenylpentenoate: The starting trans-methyl 2-N-boc-amino-5-phenylpent-4-enoate (700 mg, 2.3 mmol, prepared as described in *Tetrahedron Lett.*, 1994, 35, 3669) is deprotected and sulfonylated with pipsyl chloride (626 mg, 2.07 mmol) as described for 3a to give 217 mg of white solid.

ESI MS: m/z (rel intensity) 488.9 (100, M+NH$_4^+$), 471.9 (50, M+H$^+$).

b. trans-Methyl 2-{[4'-Methoxy-(1,1'-biphenyl)-4-yl]-sulfonyl)-amino-5-phenylpentenoate: The starting sulfonamide 59a (217 mg, 0.46 mmol) and 4-methoxyphenylboronic acid (105 mg, 0.69 mmol) are coupled as described for compound 3b to give 130 mg of the title compound as a pale orange solid.

ESI MS: m/z (rel intensity) 499.0 (70, M+NH$_4^+$), 452.0 (100, M+H$^+$).

c. The starting sulfonamide 59b (43 mg, 0.46 mmol) is dissolved in pyridine in the presence of lithium iodide (152 mg, 1.14 mmol) and refluxed for 5 hr. The mixture is then concentrated to dryness, taken up in EtOAc, washed 3x with 1N HCl, 1x with brine, dried over MgSO$_4$, filtered and evaporated. The crude material is purified over flash silica with EtOAc:MeOH (1:0 to 4:1) to give 24 mg of yellow oil which solidified on standing.

ESI MS: m/z (rel intensity) 455.0 (50, M+NH$_4^+$), 438.0 (100, M+H$^+$).

Example 60
Preparation of 2-{[4'-Methoxy-(1,1'-biphenyl)-4-yl]-sulfonyl}-amino-3-benzyloxymethyl-pent-4-enoic acid a. N-boc-Glycene-(cis-4-benzyloxybut-2-enyl) ester: The N-boc-glycine (21.9 g, 0.125 mol), cis-4-benzyloxy-2-buten-1-ol (25 mL, 0.15 mol), and 4-dimethylaminopyridine (1.5 g, 0.013 mol) are dissolved in CH$_2$Cl$_2$ and stirred at 0° C. Then N,N-dicyclohexylcarbodiimide (31 g, 0.15 mol) in 30 mL of CH$_2$Cl$_2$ is added and the reaction stirred at 0° C. for five minutes. The reaction is then stirred for twelve hours at 25° C. Additional CH$_2$Cl$_2$ is added and the reaction is washed with 1N HCl, sodium bicarbonate and then with brine. The organic extract is dried over magnesium sulfate and the solvent evaporated in vacuo.to give an orange oil which is absorbed onto silica gel and applied to a dry silica column which is eluted with hexane:EtOAc (9:1) then with hexane:EtOAc (8:2). Product fractions are combined and dried in vacuo to give the title compound as a solid.

b. 2-N-boc-amino-3-benzyloxymethyl-pent4-enoic acid: LDA solution (37.3 mmol) is prepared from N,N-diisopropylamine (5.2 mL, 37.2 mmol) in THF (30 ml, cooled to –20° C.) and n-BuLi (3.7 mL, 10 M in hexanes, 37.3 mmol). The LDA solution in THF is added to a stirred solution of allylic ester 60a (5.0 g, 14.9 mmol) and ZnCl$_2$ (17.9 mmol) in 100 mL of THF at –78° C. The mixture is allowed to come to room temperature overnight. The crude mixture is partitioned between 700 mL of ethyl acetate and 700 mL of 1N HCl. The organic layer is washed with 150 mL dilute NaHCO$_3$ solution (3x's). The bicarbonate washes are acidified with conc. HCl to pH1 and extracted with 700 mL of ethyl acetate. The ethyl acetate layer is dried over magnesium sulfate and the solvent removed in vacuo to give a white solid.

c. Methyl-2-N-(4bromobenzenesulfonyl)-amino-3-benzyloxymethyl-pent-4-enoate: The olefin substrate 60b (1.8 g, 5.37 mmol) is dissolved in 54 mL of methanol and 8.3 mL of thionyl chloride is added dropwise to the mixture and stirred at room temperature until the reaction is complete by tlc. The crude reaction is dried and re-evaporated from methanol (3 X's). The dried reaction is taken up in CH$_2$Cl$_2$ (30 ml ) and triethylamine (7 ml). 4-Bromophenylsulfonyl chloride (1.23 g, 4.83 mmol) is added and the reaction stirred overnight. The reaction solvent is removed in vacuo and the oil is taken up in ethyl acetate, washed with 1N HCl, followed with sodium bicarbonate solution, and finally with brine, then dried over magnesium sulfate and the solvent removed in vacuo. The crude material is adsorbed onto silica gel and purified over a silica column eluting with hexane followed with hexane:ethyl acetate (8:2). Product fractions are combined and dried to give a yellow oil.

d. Methyl 2-N-{[4'-methoxy-(1,1'-biphenyl)-4-yl]-sulfonyl)-amino-3-benzyloxymethyl-pent-4-enoate: The olefin substrate 60c (320 mg, 0.683 mmol) is dissolved in benzene (4 mL) and sodium carbonate (148 mg), in water (0.6 mL) is added along with tetrakis (triphenyl-phosphine) palladium. 4-Methoxyphenylboronic acid (157 mg, 1.03 mmol), in methanol (0.4 ml), is added and the mixture is refluxed overnight. Ether is added to the reaction which is washed with water (2x's) and brine (1x), the organic layer is dried over magnesium sulfate and the solvent stripped in vacuo.to give a yellow solid. The crude material is adsorbed onto silica gel and purified over a silica column eluting with with hexane:ethyl acetate (9:1) followed with hexane:ethyl acetate (1:1). Product fractions are combined and dried to give the title compound as a yellow oil.

e. The olefin substrate 60d (207 mg, 0.42 mmol) is dissolved in methanol:water (10:1) (5.5 mL) and potassium hydroxide (424 mg, 7.52 mmol) is added, then the mixture is stirred at room temperature until the reaction is complete. Ethyl acetate is added and the crude reaction is washed with 1N HCl (1x) and brine (1x). The organic layer is dried over magnesium sulfate and the solvent removed in vacuo. The crude material is adsorbed onto silica and purified over a silica column eluting with ethyl acetate:hexane (1:1) followed with ethyl acetate. The product is then eluted with ethyl acetate:methanol (9:1) and the product fractions are combined and the solvent is removed in vacuo to give the title compound as a mixture of isomers.

ESI MS: m/z (rel intensity) 482.6 (100, M+H$^+$).

Example 61

Preparation of 2-[(1,1'-biphenyl)4-yl]-sulfonyl-amino-3-benzyloxymethyl-pent-4-enoic acid a. Methyl 2-[(1,1'-bipheny)-4-yl]-sulfonyl-amino-3-benzyloxymethyl-pent-4-enoate: The olefin substrate 60b (200 mg, 0.597 mmol) is dissolved in methanol (5.4 ml) and thionyl chloride (830 ml) is added dropwise to the mixture and stirred at room temperature until the reaction is complete by tlc. The crude reaction is dried and re-evaporated from methanol (3x's). The dried reaction is taken up in CH$_2$Cl$_2$ (3 mL) and triethylamine (0.7 mL) and biphenyl-4-sulfonyl chloride (136 mg, 0.537 mmol) is added and the reaction stirred overnight. The reaction solvent is removed in vacuo and the oil is taken up in ethyl acetate, washed with 1N HCl, followed with sodium bicarbonate solution, and finally with brine, then dried over magnesium sulfate and the solvent removed in vacuo. The crude material is adsorbed onto silica gel and purified over a silica column eluting with hexane followed with hexane:ethyl acetate (8:2). Product fractions are combined and dried to give a yellow oil.

b. The methyl ester 61a (40 mg, 0.086 mmol) is dissolved in methanol:water (10:1) (1.1 mL) and potassium hydroxide (90 mg, 1.6 mmol) added, then the mixture is stirred at room temperature until the reaction is complete. Ethyl acetate is added and the crude reaction is washed with 1N HCl (1x) and brine (1x). The organic layer is dried over magnesium sulfate and the solvent removed in vacuo. The crude material is adsorbed onto silica and purified over a silica column eluting with ethyl acetate:hexane (1:1) followed with ethyl acetate. Product is eluted with ethyl acetate:methanol (9:1), product fractions are combined and the solvent removed in vacuo to give the title compound.

ESI MS: m/z (rel intensity) 469.1 (45, M+NH$_4^+$), 452.1 (100, M+H$^+$).

Example 62

Preparation of cis-2-{[4'-Methoxy-(1,1'-biphenyl)-4-yl]-sulfonyl}-amino-5-(N-pyrrolidinocarbonyl)-pent-4-enoic acid a. cis-2-Bromo-N-pyrrolidinocarbonylethene: Ethyl-cis-3-bromopentenoate is taken in CH$_2$Cl$_2$ and treated with excess pyrrolidine for 2 hr to give the desired amide.

b. tert-Butyl 2-hydroxy-6-Phenylhex-4-enylether: The starting bromoalkene 62a is taken in dry THF under argon and cooled to −78° C. A solution of 2 eq of tert-butyl lithium is added dropwise and the mixture is allowed to stir for 20 min. afterwhich a solution of 1 eq of tert-Butyl glycidyl ether in THF is the added dropwise. The mixture is allowed to stir for 15 min. and then the cooling bath is removed and the solution allowed to come to room temperature for 1 hr. The reaction is quenched with sat. NH$_4$Cl and then partitioned between water and EtOAc. The organic layer is washed with brine, dried over Mg$_2$SO$_4$, filtered and evaparated to give a crude material which is adsorbed onto silica and eluted through a flash silica column to give the title amide.

c. The amide 62b is carried forward to the title acid as described for compounds 46b–f.

Examples 63–68

The following chemical formula along with Table 5 shows the structure of compounds made according to the description in Examples 63–68 described below:

TABLE 5

| Example | R$_1$ | R$_2$ | R$_3$ |
|---|---|---|---|
| 63 | 4-MeO-C$_6$H$_4$– | C$_6$H$_5$– | —Me |
| 64 | 4-MeS-C$_6$H$_4$– | C$_6$H$_5$– | —Me |

TABLE 5-continued

| Example | R₁ | R₂ | R₃ |
|---|---|---|---|
| 65 | 4-MeO-C₆H₄- | Ph- | —CH₂Ph |
| 66 | 4-MeO-C₆H₄- | Ph- | —CH₂CH₂OMe |
| 67 | 4-PhO-C₆H₄- | Ph- | —CH₂CH₂OMe |
| 68 | 4-MeO-C₆H₄- | PhS- | —CH₂CH₂OMe |

Example 63

(2R)-{[4'-Methoxy-(1,1'-biphenyl)-4-yl]-sulfonyl)-amino-(3S)-methoxy-5-phenylpent-4ynoic acid a. t-Butyl (4S,1'R)-2,2-dimethyl-4(1'-hydroxy-3'-phenylprop-2'-ynyl)-oxazolidine-3-carboxylate: A solution of phenylacetylene (1.73 g, 17 mmol) in THF (75 mL) is cooled to −78° C. and then n-butyllithium (2.5 M, 6.3 mL, 15.7 mmol) is added. The resulting mixture is warmed to −20° C. and stirred for 15 minutes. The mixture is re-cooled to −78° C. and then 1-butyl (S)-4-formyl-2,2-dimethyl-3-oxazolidinecarboxylate (3 g, 13.1 mmol) in THF (10 mL) is slowly added. The mixture is then warmed to −20° C. and stirred for 30 minutes. The reaction is quenched by the addition of saturated ammonium chloride solution (30 mL). The mixture is then poured into water and extracted with methylene chloride. The organic extracts are dried (MgSO₄) and then concentrated to an oil under reduced pressure. The oil is purified by chromatography on silica gel using 9:1 hexane:EtOAc as the eluent to provide 2.20 g of the desired compound as a pale oil.

ESI MS: m/z (rel intensity) 332 (100, M+H⁺).

b. t-Butyl (4S,1'R)-2,2-dimethyl-4-(1'-methoxy-3'-phenylprop-2'-ynyl)-oxazolidine-3-carboxylate: The alcohol 63a (10.04 g, 30.3 mmol) in THF (150 mL) is stirred at 0° C. and then sodium hexamethyldisilazide (0.6 M, 60 mL, 36.4 mmol) is added. The mixture is stirred at 0° C. for 15 min. and then iodomethane (4.73 g, 33.3 mmol) is added. The resulting mixture is stirred at room temperature overnight and then the reaction is quenched by the addition of saturated ammonium chloride solution (20 mL). The mixture is poured into water and then extracted with methylene chloride. The organic extracts are dried (Na₂SO₄) and then concentrated to an oil under reduced pressure. Purification of the oil is accomplished by chromatography on silica gel using 9:1 hexane:EtOAc as the eluent to provide the desired product as a colorless oil.

ESI MS: m/z (rel intensity) 346 (100, M+H⁺).

c. t-Butyl (1S,2R)-N-[2-Methoxy-1-(hydroxymethyl)-4-phenylbut-2-ynyl)-carbamate: The acetonide 63b (9.22 g, 26.7 mmol) in methanol (150 mL) is stirred at room temperature and then Amberlyst 15 (15 g) is added. The resulting heterogeneous mixture is stirred at room temperature for 24 hr. The mixture is filtered through celite with the aid of methanol. The product is purified by chromatography on silica gel using 7:3 hexane:EtOAc as the eluent. The product is obtained as a colorless oil which solidified to a white solid upon standing.

ESI MS: m/z (rel intensity) 306 (100, M+H⁺).

d. (1S,2R)-N-[2-Methoxy-1-(hydroxymethyl)-1-amino-4-phenylbut-2-yne: The carbamate 63c (5.0 g, 16.4 mmol) in dioxane is stirred at room temperature and then 4 N HCl (15 mL) is added. The resulting mixture is stirred at room temperature for 14 hr. The reaction mixture is made basic by the addition of saturated sodium bicarbonate solution. The resulting mixture is extracted with methylene chloride. The organic extracts are dried (MgSO$_4$) and then concentrated to an oil under reduced pressure.

ESI MS: m/z (rel intensity) 206 (100, M+H$^+$).

e. [(2R)-Methoxy-1-(hydroxymethyl)-(1S)-(4'-iodophenylsulfonyl)-amino-4-phenylbut-2-yne: The amino alcohol 63d (3.30 g, 16.1 mmol) in dioxane (30 mL) and water (30 mL) is stirred at room temperature and then triethylamine (3.25 g, 32.2 mmol) followed by pipsyl chloride (5.3 g, 17.7 mmol) are added. The resulting mixture is stirred at room temperature overnight. The reaction is diluted with 1N HCl and then extracted with methylene chloride. The organic extracts are dried and then concentrated to an oil under reduced pressure.

ESI MS: m/z (rel intensity) 472 (100, M+H$^+$).

f. Methyl (2R)-(4'-Iodophenylsulfonyl)-amino-(3S)-methoxy-5-phenylpent-4-ynoate: The alcohol 63e (2.0 g, 4.24 mmol) in acetone (100 mL) is stirred at room temperature and then the Jones reagent (8N, 30 mL, excess) is slowly added. The resulting mixture is stirred at room temperature for 4 hr. and then the reaction is quenched by the addition of isopropanol. A green precipitate formed after the mixture is stirred for 30 min. The solution is then filtered through celite with the aid of acetone. The filtrate is concentrated to an oil under reduced pressure. The oil is dissolved in methanol and then an ethereal solution of diazomethane is added. The mixture became slightly yellow when excess diazomethane had been added. The mixture is concentrated to a light yellow solid. Purification of the solid is accomplished by chromatography on silica gel using 8:2 hexane:EtOAc as the eluent to provide the product as a yellow solid.

ESI MS: m/z (rel intensity) 500 (100, M+H$^+$).

g. Methyl (2R)-{[4'-Methoxy-(1,1'-biphenyl)-4-yl]-sulfonyl}-amino-(3S)-methoxy-5-phenylpent-4ynoate: The starting sulfonamide 63f (510 mg, 1.02 mmol) and 4-methoxyphenylboronic acid (230 mg, 1.53 mmol) are taken up in 10 mL of benzene, 1.5 mL of EtOH and 1.5 mL of water in the presence of Pd(PPh$_3$)$_4$ (35 mg, 0.03 mmol) and 200 mg of Na$_2$CO$_3$ and brought to reflux for 18 hr. The mixture is cooled to room temperature, poured into water, and extracted with methylene chloride. The organic layer is dried over MgSO$_4$, filtered and evaporated. The crude product is purified by silica gel chromatography using 9:1 hexane:EtOAc to give the desired product as a colorless oil.

ESI MS: m/z (rel intensity) 480.0 (100, M+H$^+$).

h. (2R)-{[4'-Methoxy-(1,1'-biphenyl)-4-yl]-sulfonyl}-amino-(3S)-methoxy-5-phenylpent-4-ynoic acid: The methyl ester 63 g (350 mg, 0.73 mmol) is dissolved in water:methanol:THF (5 mL:5 mL:5 mL) and then lithium hydroxide (1 g, excess) is added. The resulting mixture is stirred overnight at room temperature. The reaction is acidified with 1N HCl and then the mixture is extracted with methylene chloride. The organic extracts are dried (MgSO$_4$) and then concentrated to an oil under reduced pressure. Purification is accomplished on reverse phase HPLC using a gradient from water to acetonitrile. The product is obtained as a white powder.

ESI MS: m/z (rel intensity) 464. (100, M–H$^+$).

Example 64

(2R)-{[4'-Thiomethoxy-(1,1'-biphenyl)-4-yl]-sulfonyl}-amino-(3S)-methoxy-5-phenylpent-4-ynoic acid a. Methyl (2R)-(4'-Thiomethoxybiphenylsulfonyl)-amino-(3S)-methoxy-5phenylpent-4-ynoate: The starting sulfonamide 63f (620 mg, 1.24 mmol) and 4-thiomethoxyphenylboronic acid (310 mg, 1.86 mmol) is taken up in 10 mL of benzene, 1.5 mL of EtOH and 1.5 mL of water in the presence of Pd(PPh$_3$)$_4$ (43 mg, 0.03 mmol) and 262 mg of Na$_2$CO$_3$ and brought to reflux for 4 hr. The mixture is cooled to room temperature, poured into water, and extracted with methylene chloride. The organic layer is dried over MgSO$_4$, filtered and evaporated. The crude product is purified by silica gel chromatography using 9:1 hexane:EtOAc to the desired product as a colorless oil.

ESI MS: m/z (rel intensity) 496.0 (35, M+H$^+$).

b. (2R)-{[4'-Methoxy-(1,1-biphenyl)-4-yl]-sulfonyl}-amino-(3S)-methoxy-5-phenylpent-4-ynoic acid: The methyl ester 64a (450 mg, 0.91 mmol) is dissolved in water/methanol/THF (5 mL/5 mL/5 mL) and then lithium hydroxide (1 g, excess) is added. The resulting mixture is stirred overnight at room temperature. The reaction is acidified with 1N HCl and the product crashed out of solution. The product is obtained as a white powder.

ESI MS: m/z (rel intensity) 480. (100, M=H$^+$).

Example 65

(2R)-{[4'-Methoxy-(1,1'-biphenyl)-4-yl]-sulfonyl}-amino-(3S)-benzyloxy-5-phenylpent-4-ynoic acid a. t-Butyl (4S,1'R)-2,2-dimethyl-4-(1'-benzyloxy-3'-phenylprop-2'-ynyl)-oxazolidine-3-carboxylate: The alcohol 63a (7.80 g, 23.5 mmol) in DME (150 mL) is stirred at 0° C. and then sodium hydride (1.13 g, 28.2 mmol) is added. The mixture is stirred at 0° C. for 15 min. and then benzylbromide (4.43 g, 25.9 mmol) is added. The resulting mixture is stirred at room temperature overnight and then the reaction is quenched by the addition of saturated ammonium chloride solution (20 mL). The mixture is poured into water and then extracted with methylene chloride. The organic extracts are dried (Na$_2$SO$_4$) and then concentrated to an oil under reduced pressure. Purification of the oil is accomplished by chromatography on silica gel using 9:1 hexane:EtOAc as the eluent to provide the desired product as a colorless oil.

ESI MS: m/z (rel intensity) 422 (100, M+H$^+$).

b. t-Butyl (1S,2R)-N-[2-Benzyloxy-1-(hydroxymethyl)-4-phenylbut-2-ynyl)-carbamate: The acetonide 65a (8.80 g, 20.9 mmol) in methanol (150 mL) is stirred at room temperature and then Amberlyst 15 (12 g) is added. The resulting heterogeneous mixture is stirred at room temperature for 24 hr. The mixture is filtered through celite with the aid of methanol. The product is purified by chromatography on silica gel using 7:3 hexane:EtOAc as the eluent. The product is obtained as a colorless oil.

ESI MS: m/z (rel intensity) 382 (20, M+H$^+$).

c. (1S,2R)-N-[2-Benzyloxy-1-(hydroxymethyl)-1-amino-4-phenylbut-2-yne: The carbamate 65b (5.60 g, 14.6 mmol) in dioxane is stirred at room temperature and then 4 N HCl (15 mL) is added. The resulting mixture is stirred at room temperature for 14 hr. The reaction mixture is made basic by the addition of saturated sodium bicarbonate solution. The resulting mixture is extracted with methylene chloride. The organic extracts are dried (MgSO$_4$) and then concentrated to an oil under reduced pressure.

ESI MS: m/z (rel intensity) 282 (100, M+H$^+$).

d. 1(2R)-Benzyloxy-1-(hydroxymethyl)-(1S)-(4'-bromophenylsulfonyl)-amino-4-phenylbut-2-yne: The amino alcohol 65c (4.0 g, 14.2 mmol) in dioxane (30 mL) and water (30 mL) is stirred at room temperature and then triethylamine (2.88 g, 28.4 mmol) followed by 4-bromophenylsulfonyl chloride (3.81 g, 14.9 mmol) are added. The resulting mixture is stirred at room temperature overnight. The reaction is diluted with 1N HCl and then extracted with methylene chloride. The organic extracts are dried and then concentrated to an oil under reduced pressure.

ESI MS: m/z (rel intensity) 501 (100, M+H$^+$).

e. Methyl (2R)-(4'-Bromophenylsulfonyl)-amino-(3S)-benzyloxy-5-phenylpent-4-ynoate: The alcohol 65d (5.30 g, 10.6 mmol) in acetone (100 mL) is stirred at room temperature and then the Jones reagent (8N, 40 mL, excess) is slowly added. The resulting mixture is stirred at room temperature for 4 hr. and then the reaction is quenched by the addition of isopropanol. A green precipitate forms after the mixture is stirred for 30 min. The solution is then filtered through celite with the aid of acetone. The filtrate is concentrated to an oil under reduced pressure. The oil is dissolved in methanol and then an ethereal solution of diazomethane is added. The mixture becomes slightly yellow when excess diazomethane has been added. The mixture is concentrated to a light yellow solid. Purification of the solid is accomplished by chromatography on silica gel using 8/2 hexane/EtOAc as the eluent to provide the product as a yellow solid.

ESI MS: m/z (rel intensity) 545, 547 (100, M+NH$_3^+$).

f. Methyl (2R)-{[4'-Methoxy-(1,1'-biphenyl)-4-yl]-sulfonyl}-amino-(3S)-benzyl-oxy-5-phenyl-pent-4-ynoate: The starting sulfonamide 65e (927 mg, 1.75 mmol) and 4-methoxyphenylboronic acid (400 mg, 2.63 mmol) are taken up in 25 mL of benzene, 1.5 mL of EtOH and 1.5 mL of water in the presence of Pd(PPh$_3$)$_4$ (61 mg, 0.05 mmol) and 371 mg of Na$_2$CO$_3$ and brought to reflux for 4 hr. The mixture is cooled to room temperature, poured into water, and extracted with methylene chloride. The organic layer is dried over MgSO$_4$, filtered and evaporated. The crude product is purified by silica gel chromatography using 9:1 hexane:EtOAc to give the desired product as a colorless oil.

ESI MS: m/z (rel intensity) 556.0 (20, M+H$^+$).

g. (2R)-{[4'-Methoxy-(1,1'-biphenyl)-4-yl]-sulfonyl}-amino-(3S)-benzyloxy-5-phenylpent-4-ynoic acid: The methyl ester 65f (630 mg, 1.13 mmol) is dissolved in water:methanol:THF (5 mL:5 mL:5 mL) and then lithium hydroxide (1 g, excess) is added. The resulting mixture is stirred overnight at room temperature. The reaction is acidified with 1N HCl and then the product crashes out of solution. The product is obtained as a light tan powder.

ESI MS: m/z (rel intensity) 540. (100, M−H$^+$).

Example 66

Preparation of (2R)-{[4'-Methoxy-(1,1'-biphenyl)-4-yl]-sulfonyl}-amino-(3S)-(2-methoxyethoxy)-5-phenylpent-4-ynoic acid a. t-Butyl (4S,1'R)-2,2-dimethyl-4-[1'-(2-methoxyethoxy)-3'-phenylprop-2'-ynyl]-oxazolidine-3-carboxylate: The alcohol 63a is coupled with 1-chloro-2-methoxyethane to give the title ether as described for compound 65a.

b. The ether 66a is converted to the title acid according to the sequence of reactions described for 65b–g.

Example 67

Preparation of (2R)-{[4'-Phenyloxy-(1,1'-biphenyl)-4-yl]-sulfonyl}-amino-(3S)-(2-methoxyethoxy)-5-phenylpent-4-ynoic acid a. (1S,2R)-N-[2-(2-Methoxyethoxy)-1-(hydroxymethyl)-1-amino-4-phenylbut-2-yne: The ether 66a is converted to the title amine according to the sequence of reactions described for 65b–c.

b. [(2R)-(2-Methoxyethoxy)-1-(hydroxymethyl)-(1S)-{[4'-phenyloxy-(1,1'-biphenyl)-4-yl]-sulfonyl)-amino-4-phenylbut-2-yne: The amine 67a is coupled to sulfonyl chloride 9 g according to the procedure described for 65d.

c. The alcohol 67b is oxidized to the title acid according to the procedure described for compound 65e.

Example 68

Preparation of (2R)-{[4'-Methoxy-(1,1'-biphenyl)-4yl]-sulfonyl}-amino-(3S)-(2-methoxyethoxy)-5-phenylthiomethyl-pent-4ynoic acid a. t-Butyl (4S,1'R)-2,2-dimethyl-4-(1'-hydroxy-3'-phenylthiomethyl-prop-2'-ynyl)-oxazolidine-3-carboxylate: The phenylthiomethylacetylene is nucleophillically coupled with t-butyl (S)-4-formyl-2,2-dimethyl-3-oxazolidinecarboxylate as described for compound 63a to give the title compound.

b. t-Butyl (4S,1'R)-2,2-dimethyl-4(1'-(2-methoxyethoxy)-3'-phenylprop-2'-ynyl)-oxazolidine-3-carboxylate: The alcohol 68a is coupled with 1-chloro-2-methoxyethane according to the procedure described for 63b to give the title ether.

c. The oxazolidine 68b is carried forward to the title acid according to the sequence of reactions described for 63c–h.

Examples 69–94

The following chemical formula along with Table 6 shows the structure of compounds made according to the description in Examples 69–94 described below:

TABLE 6
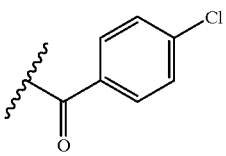
| Example | R₁ | R₂ |
|---|---|---|
| 69 | 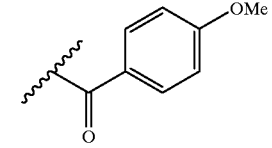 | —Ph |
| 70 | 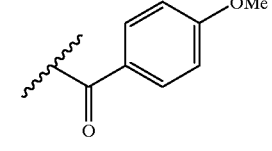 | —Ph |
| 71 | 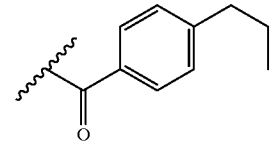 | —CH₂OMe |
| 72 | 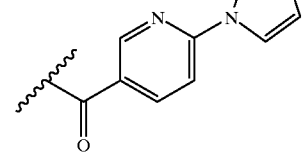 | —Ph |
| 73 | 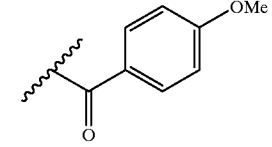 | —Ph |
| 74 | 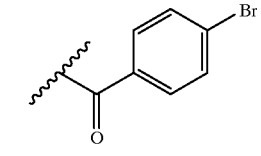 | —CH₂OPh |
| 75 | 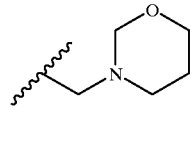 |  |

TABLE 6-continued

| Example | R₁ | R₂ |
|---|---|---|
| 76 | 4-Cl-phenyl-C(=O)- | —CH₂OMe |
| 77 | 4-Br-phenyl-C(=O)- | —CH₂OMe |
| 78 | 6-(CF₃)-pyridin-3-yl-C(=O)- | —CH₂OPh |
| 79 | 6-(CF₃)-pyridin-3-yl-C(=O)- | —CH₂OPh |
| 80 | 6-(OCH₂CF₃)-pyridin-3-yl-C(=O)- | —CH₂OPh |
| 81 | 5-methyl-pyrazin-2-yl-C(=O)- | CH₂OPh |
| 82 | 5-methoxy-1H-indol-2-yl-C(=O)- | CH₂OPh |

TABLE 6-continued
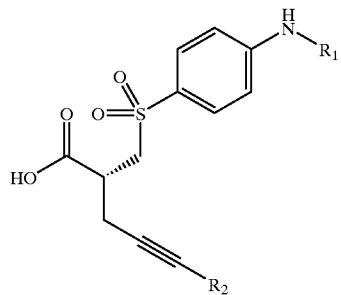
| Example | R₁ | R₂ |
| --- | --- | --- |
| 83 | (2-methyl-2H-indolizin-3-yl)carbonyl | CH₂OPh |
| 84 | morpholin-4-ylcarbonyl | —Ph |
| 85 | morpholin-4-ylcarbonyl | —CH₂OPh |
| 86 | morpholin-4-ylcarbonyl | —CH₂OMe |
| 87 | pyrrolidin-1-ylcarbonyl | —Ph |
| 88 | pyrrolidin-1-ylcarbonyl | —CH₂OMe |
| 89 | phenylaminocarbonyl | —Ph |

TABLE 6-continued

[Structure: central scaffold with HOOC-CH(CH2-SO2-C6H4-NH-R1)-CH2-C≡C-R2]

| Example | R₁ | R₂ |
|---------|----|----|
| 90 | —C(O)—N(Me)(Ph) | —Ph |
| 91 | —C(O)—NH-(5-methylisoxazol-2-yl) | —Ph |
| 92 | —C(O)—NH-(benzothiazol-2-yl) | —Ph |
| 93 | —C(O)—CH₃ (acetyl) | —CH₂OMe |
| 94 | —SO₂-(4-methoxyphenyl) | —CH₂OMe |

Example 69
Preparation of 2-{[4-(4-Chlorobenzoyl)amino]-benzenesulfonyl}-amino-5-phenylpent-4-ynoic acid:

a. Methyl 2-(4-acetamidobenzenesulfonyl)-amino-5-pheny-pent-4ynoate: To a solution of boc-amine 1c (0.6 g, 2.5 mmol) in CH₂Cl₂ (15 mL) is added TFA (1 mL). The mixture is allowed to stir for 1 hr and then it is concentrated unde reduced pressure to give a residue which is taken in dioxane (8 mL), water (5 mL) and Et₃N (1.39 mL, 10 mmol). To this, 4-acetamidobenzenesulfonyl chloride (650 mg, 3.0 mmol) is added slowly at room temperature. The reaction mixture is stirred overnight, diluted with water, and extracted three times with EtOAc. The combined EtOAc layers are washed with 1 N HCl, H₂O, brine, dried over MgSO₄, and concentrated to give the desired product as an off-white solid.

b. Methyl 2-{[4-(4-chlorobenzoyl)amino]-benzene sulfonyl}-amino-5-phenylpent-4-yn-oate: To a solution of acetomide 69a (0.21 g, 0.5 mmol) in water (5 mL) is added concentrated HCl (1 mL, 12 mmol) slowly. The reaction mixture is heated to reflux for 3 h then concentrated to dryness and azeotroped with toluene. The resulting residue is dissolved in 10 mL of CH₃OH, followed by slow addition of 0.5 mL of thionyl chloride. The mixture is stirred overnight, and solvent is removed under reduced pressure. The crude aniline intermediate is dissolved in CH₂Cl₂ (3 mL) and cooled to 0° C. 4-Methylmorpholine (0.16 mL, 1.4 mmol) is added, followed by 4-chlorobenzoyl chloride (0.091 mL, 0.71 mmol). The reaction mixture is stirred overnight, diluted with water, and extracted three times with EtOAc. The combined EtOAc layers are washed with 1 N HCl, H₂O, brine, dried over MgSO₄, and concentrated to a solid which is purified by column chromatography eluting with hexane:EtOAc (6:4) to give the desired product as a solid.

c. The methyl ester 69b (120 mg, 0.24 mmol) is treated with lithium hydroxide monohydrate (100 mg, 2.4 mmol) in 3 mL of THF and 3 mL of water and stirred for 2 hr at room temperature, then concentrated to dryness and diluted with water. The mixture is extracted twice with Et$_2$O The Et$_2$O layers are discarded and the aqueous layer is diluted with 0.5 mL of dil. NaH$_2$PO$_4$ and neutralized carefully with 1N HCl to pH 6, then extracted three times with EtOAc. The combined EtOAc layers are washed with brine, dried over MgSO$_4$, and concentrated to a solid which is recrystallized from EtOAc/hexane to the desired product as a white solid.

Example 70

Preparation of 2-{[4-(4-Methoxybenzoyl)amino]-benzenesulfonyl}-amino-5-phenylpent-4-ynoic acid:

a. Methyl 2-{[4-(4-methoxybenzoyl)amino]-benzenesulfonyl}-amino-5-phenyl-pent-4-ynoate: The acetamide 69a is hydrolyzed, esterified and converted to the title amide with 4-methoxybenzoyl chloride as described for compound 69b to give the title ester.

b. The starting ester 70a is saponified according to the procedure described for compound 69c to give the title acid.

Example 71

Preparation of 2-{[4-(4-Methoxybenzoyl)amino]-benzenesulfonyl}-amino-6-methoxyhex-4-ynoic acid:

a. 1-Hydroxy-2-(4-acetamidobenzenesulfonyl)-amino-6-methoxyhex-4-yn: The starting azide 50b is decomposed and coupled with 4-acetamidobenzene-sulfonyl chloride as described for compound 46d to give the title sulfonamide.

b. 2-(4-acetamidobenzenesulfonyl)-amino-6-methoxyhex-4-ynoic acid: The starting alcohol 71a is oxidized to its relative carboxylic acid as described for compound 46f.

c. Methyl 2-(4-aminobenzenesulfonyl)-amino-6-methoxyhex-4-ynoate: The starting amide 71b (2.12 g, 6 mmole) is taken in 25 mL of methanol, treated with 10 drops of con. H$_2$SO$_4$, stirred for 24 hr, neutralized with Na$_2$CO$_3$ and evaporated. The residue is partitioned between EtOAc and 5% NaHCO$_3$. The organic layer is washed with brine, dried over MgSO$_4$, filtered and evaporated to give a yellow oil which is carried forward without purification.

d. Methyl 2-{[4-(4-Methoxybenzoyl)amino]-benzenesulfonyl}-amino-6-methoxyhex-4-ynoate: The starting amine 71c (500 mg, 1.5 mmole) is taken in 10 mL of CH$_2$Cl$_2$ in the presence of 1 mL of NEt$_3$ and treated with 4-methoxybenzenesulfonyl chloride (341 mg, 1.65 mmole). The resulting solution is stirred for 16 hr and then partitioned between 1N HCl and EtOAc. The organic layer is washed with brine, dried over MgSO$_4$, filtered and evaporated. The crude material is chromatographed over flash silica with hexanes:EtOAc (1:1) to give a white solid.

e. The starting ester 71d is hydrolyzed as described for compound 69c to give the title acid.

ESI MS: m/z (rel intensity) 402.0 (100, M−H$^+$).

Example 72

Preparation of 2-{[4-(5-n-propylpyridin-2-oyl)-amino]-benzenesulfonyl}-amino-5-phenylpent-4-ynoic acid:

a. Methyl 2-{[4-(5-n-propylpyridin-2-oyl)-amino]-benzenesulfonyl}-amino-5phenyl-pent-4-yn-oate: The acetamide 69a is hydrolyzed and esterified described for compound 69b. This crude material is then taken in CH$_2$Cl$_2$ in the presence of DCC and HOBT and treated with 5-n-propylpyridin-2-yl-carboxylic acid to generate the title amide.

b. The starting ester 72a is saponified according to the procedure described for compound 69c to give the title acid.

Example 73

Preparation of 2-{[4-(6-N-pyrrolylpyridin-3-oyl)-amino]-benzenesulfonyl}-amino-5-phenylpent-4-ynoic acid:

a. Methyl 2-{[4-(6-N-pyrrolidylpyridin-3-oyl)-amino]-benzenesulfonyl}-amino-5-phenylpent-4-yn-oate : The acetamide 69a is hydrolyzed and esterified described for compound 69b. This crude material is then taken in CH$_2$Cl$_2$ in the presence of DCC and HOBT and treated with 6-N-pyrrolylpyridin-3-yl-carboxylic acid to generate the title amide.

b. The starting ester 73a is saponified according to the procedure described for compound 69c to give the title acid.

Example 74

Preparation of 2-{[4-(4-Methoxybenzoyl)amino]-benzenesulfonyl}-amino-6-phenyloxyhex-4-ynoic acid:

a. 1-Hydroxy-2-azido-6-phenyloxyhex-4-yn: The starting alcohol 49a is converted to the title azide as described the sequence of reactions for compounds 46b–c.

b. 1-Hydroxy-2-(4-acetamidobenzenesulfonyl)-amino-6-phenyloxyhex-4-yn: The starting azide 74a is decomposed to its relative amine with PPh$_3$ and then coupled with 4-acetamidobenzenesulfonyl chloride as described for compound 46d to give the title sulfonamide c. 2-(4-acetamidobenzenesulfonyl)-amino-benzenesulfonyl}-amino-6-phenyl-oxyhex-4-ynoic acid: The starting alcohol 74b is oxidized with Jones reagent as described for compound 46f to give the title acid.

d. Methyl 2-{[4-(4-Methoxybenzoyl)amino]-benzenesulfonyl}-amino-6-phenyloxyhex-4-ynoate: The acetamide 74c is hydrolyzed, esterified and converted to the title amide with 4-methoxybenzoyl chloride as described for compound 69b to give the title ester.

e. The starting ester 74d is saponified according to the procedure described for compound 69c to give the title acid.

ESI MS: m/z (rel intensity) 526.0 (50, M+NH$_4^+$), 509.0 (100, M+H$^+$).

Example 75

Preparation of 2-{[4-(4-Bromobenzoyl)amino]-benzenesulfonyl}-amino-6-morpholinohex-4-ynoic acid The starting acetamide 44a is deprotected, coupled to 4-bromobenzoyl chloride, and hydrolyzed as described for compounds 71c–e to give the title acid.

ESI MS: m/z (rel intensity) 571.8 (23, M+Na$^+$), 573.8 (50, M+Na$^+$), 549.9 (100, M+H$^+$), 551.9(100,M+H$^+$).

Example 76

Preparation of 2-{[4-(4-Chlorobenzoyl)amino]-benzenesulfonyl}-amino-6-methoxyhex-4-ynoic acid The starting amine 71c is coupled to 4-chlorobenzoyl chloride, and hydrolyzed as described for compounds 71d–e to give the title acid.

Example 77

Preparation of 2-{[4-(4-Bromobenzoyl)amino]-benzenesulfonyl}-amino-6-methoxyhex-4-ynoic acid The starting amine 71c is coupled to 4-bromobenzoyl chloride, and hydrolyzed as described for compounds 71d–e to give the title acid.

Example 78

Preparation of 2-{[4-(6-trifluoromethylpyridin-3-oyl)-amino]-benzenesulfonyl}-amino-6-phenyloxyhex-4ynoic acid a. Methyl 2-{[4-(6-trifluoromethylpyridin-3-oyl)-amino]-benzenesulfonyl}-amino-6-phenyloxyhex-4-ynoate: The acetamide 74a is hydrolyzed and esterified as described for compound 69b. This crude material is then taken in CH$_2$Cl$_2$ in the presence of DCC and HOBT and treated with 6-trifluoromethylpyridin-2-yl-carboxylic acid to generate the title amide.

b. The starting ester 78a is saponified according to the procedure described for compound 69c to give the title acid.

Example 79
Preparation of 2-{[4-(6-cyanopyridin-3-oyl)-amino]-benzenesulfonyl}-amino-6-phenyloxyhex-4ynoic acid:

a. Methyl 2-{[4-(6-cyanopyridin-3-oyl)-amino]-benzenesulfonyl}-amino-6-phenyloxy-hex-4-ynoate: The acetamide 74a is hydrolyzed and esterified as described for compound 69b. This crude material is then taken in CH$_2$Cl$_2$ in the presence of DCC and HOBT and treated with 6-cyanopyridin-2-yl-carboxylic acid to generate the title amide.

b. The starting ester 79a is saponified according to the procedure described for compound 69c to give the title acid.

Example 80
Preparation of 2-{[4-(6-trifluoromethylmethoxypyridin-3-oyl)-amino]-benzenesulfonyl}-amino-6-phenyloxyhex-4-ynoic acid:

a. Methyl 2-{[4-(6-trifluoromethylmethoxypyridin-3-oyl)-amino]-benzenesulfonyl}-amino-6-phenyloxy-hex-4-ynoate: The acetamide 74a is hydrolyzed and esterified as described for compound 69b. This crude material is then taken in CH$_2$Cl$_2$ in the presence of DCC and HOBT and treated with 6-trifluoromethylmethoxypyridin-2-yl-carboxylic acid to generate the title amide.

b. The starting ester 80a is saponified according to the procedure described for compound 69c to give the title acid.

Example 81
Preparation of 2-{[4-(5-methylpyrizin-2-oyl)-amino]-benzenesulfonyl}-amino-6-phenyloxyhex-4-ynoic acid:

a. Methyl 2-{[4(5-methylpyrizin-2-oyl)-amino]-benzenesulfonyl}-amino-6-phenyl-oxyhex-4-ynoate: The acetamide 74a is hydrolyzed and esterified as described for compound 69b. This crude material is then taken in CH$_2$Cl$_2$ in the presence of DCC and HOBT and treated with 5-methylpyrizin-2-yl-carboxylic acid to generate the title amide.

b. The starting ester 81a is saponified according to the procedure described for compound 69c to give the title acid.

Example 82
Preparation of 2-{[4-(5-methoxyindol-2-oyl)-amino]-benzenesulfonyl}-amino-6-phenyloxyhex-4-ynoic acid:

a. Methyl 2-{[4-(5-methoxyindol-2-oyl)-amino]-benzenesulfonyl}-amino-6-phenyl-oxyhex-4-ynoate3 The acetamide 74a is hydrolyzed and esterified as described for compound 69b. This crude material is then taken in CH$_2$Cl$_2$ in the presence of DCC and HOBT and treated with 5-methoxyindol-2-yl-carboxylic acid to generate the title amide.

b. The starting ester 82a is saponified according to the procedure described for compound 69c to give the title acid.

Example 83
Preparation of 2-{[4-(1N-methylindol-2-oyl)-amino]-benzenesulfonyl}-amino-6-phenyloxyhex-4-ynoic acid:

a. Methyl 2-{[4-(1N-methylindol-2-oyl)-amino]-benzenesulfonyl}-amino-6-phenyl-oxyhex-4-ynoate: The acetamide 74a is hydrolyzed and esterified as described for compound 69b. This crude material is then taken in CH$_2$Cl$_2$ in the presence of DCC and HOBT and treated with 1N-methylindol-2-yl-carboxylic acid to generate the title amide.

b. The starting ester 83a is saponified according to the procedure described for compound 69c to give the title acid.

Example 84
Preparation of 2-{[4-(N-morpholinocarbonyl)-amino]-benzenesulfonyl}-amino-5-phenylpent-4-ynoic acid:

a. Methyl 2-{[4-(chlorocarbonylamino]-benzenesulfonyl}-amino-5-phenyl-pent-4-yn-- oate: The acetamide 69a is hydrolyzed and esterified described for compound 69b. This crude material is then taken in CH$_2$Cl$_2$ in the presence of Et$_3$N and treated with an excess of triphosgene to give the title carbamoyl chloride.

b. Methyl 2-{[4-(N-morpholinocarbonyl)-amino]-benzenesulfonyl}-amino-5-phenyl-pent-4-yn-oate: The carbamoyl chloride 84a is taken in CH$_2$Cl$_2$ in the presence of Et$_3$N at 0° C. and treated with I eq of morpholine to give the title urea.

c. The starting ester 84b is saponified according to the procedure described for compound 69c to give the title acid.

Example 85
Preparation of 2-{[4-(N-morpholinocarbonyl)-amino]-benzenesulfonyl}-amino-5-phenyloxyhex-4-ynoic acid:

a. Methyl 2-{[4(chlorocarbonylamino]-benzenesulfonyl}-amino-5-phenyloxyhex-4-yn-oate: The acetamide 74a is hydrolyzed and esterified described for compound 69b. This crude material is then taken in CH$_2$Cl$_2$ in the presence of Et$_3$N and treated with an excess of triphosgene to give the title carbamoyl chloride.

b. Methyl 2-{[4-(N-morpholinocarbonyl)-amino]-benzenesulfonyl}-amino-5phenyl-hex-4-yn-oate: The carbamoyl chloride 85a is taken in CH$_2$Cl$_2$ in the presence of Et$_3$N at 0° C. and treated with 1 eq of morpholine to give the title urea.

c. The starting ester 82b is saponified according to the procedure described for compound 69c to give the title acid.

Example 86
Preparation of 2-{[4-(N-morpholinocarbonyl)-amino]-benzenesulfonyl}-amino-5-methoxyhex-4-ynoic acid The starting amine 71c is coupled to N-morpholinecarbonyl chloride, and hydrolyzed as described for compounds 71d–e to give the title acid.

ESI MS: m/z (rel intensity) 448.1 (25, M+NH$_4^+$), 426.2 (10, M+H$^+$).

Example 87
Preparation of 2-{[4-(N-pyrrolidinocarbonyl)-amino]-benzenesulfonyl}-amino-5-phenylpent-4-ynoic acid:

a. Methyl 2-{[4-(N-pyrrolidinocarbonyl)-amino]-benzenesulfonyl}-amino-5-phenylpent-4-yn-oate: The carbamoyl chloride 84a is taken in CH$_2$Cl$_2$ in the presence of Et$_3$N at 0° C. and treated with 1 eq of morpholine to give the title urea.

b. The starting ester 87a is saponified according to the procedure described for compound 69c to give the title acid.

Example 88
Preparation of 2-{[4-(N-pyrrolidinocarbonyl)-amino]-benzenesulfonyl}-amino-6-methoxyhex-4-ynoic acid The starting amine 71c is coupled to N-pyrrolidinecarbonyl chloride, and hydrolyzed as described for compounds 71d–e to give the title acid.

ESI MS: m/z (rel intensity) 427.2 (40, M+NH$_4^+$), 410.2 (100, M+H$^+$).

Example 89
Preparation of 2-{[4-(N-phenylaminocarbonyl)-amino]-benzenesulfonyl}-amino-5-phenylpent-4-ynoic acid:

a. Methyl 2-{[4-(N-phenylaminocarbonyl)-amino]-benzenesulfonyl}-amino-5-phenylpent-4-yn-oate: The carbamoyl chloride 84a is taken in CH₂Cl₂ in the presence of Et₃N and treated with 1 eq of aniline to give the title urea.

b. The starting ester 89a is saponified according to the procedure described for compound 69c to give the title acid.

Example 90
Preparation of 2-{[4-(N,N-methylphenylaminocarbonyl)-amino]-benzenesulfonyl}-amino-5-phenylpent-4-ynoic acid:

a. Methyl 2-{[4-{[4-(N,N-methylphenylaminocarbonyl)-amino]-benzenesulfonyl}-amino-5-phenyl-pent-4-yn-oate: The carbamoyl chloride 84a is taken in CH₂Cl₂ in the presence of Et₃N and treated with 1 eq of methylaniline to give the title urea.

b. The starting ester 90a is saponified according to the procedure described for compound 69c to give the title acid.

Example 91
Preparation of 2-{[4-(N-[4-methyloxazol-2-yl]-carbonyl)-amino]-benzenesulfonyl}-amino-5-phenylpent-4-ynoic acid:

a. Methyl 2-{[4-(N-[4-methyloxazol-2-yl]-carbonyl)-amino]-amino-5-phenyl-pent-4-yn-oate: The carbamoyl chloride 84a is taken in CH₂Cl₂ in the presence of Et₃N and treated with 1 eq of 2-amino-4-methyloxazole to give the title urea.

b. The starting ester 91a is saponified according to the procedure described for compound 69c to give the title acid.

Example 92
Preparation of 2-{[4-(N-[benzthiazol-2-yl]-carbonyl)-amino]-benzenesulfonyl}-amino-5-phenylpent-4-ynoic acid:

a. Methyl 2-{[4-(N-[benzthiazol-2-yl]-carbonyl)-amino]-amino-5-phenyl-pent-4-yn-oate: The carbamoyl chloride 84a is taken in CH₂Cl₂ in the presence of Et₃N and treated with 1 eq of 2-amino-benzthiazole to give the title urea.

b. The starting ester 92a is saponified according to the procedure described for compound 69c to give the title acid.

Example 93
Preparation of 2-(4-acetylamino)-benzenesulfonyl-amino-6-methoxyhex-4-ynoic acid The starting amine 71c is coupled to acetic anhydride, and hydrolyzed as described for compounds 71d–e to give the title acid.

Example 94
Preparation of 2-(4-(4-methoxybenzenesulfonyl)-amino)-benzenesulfonyl}-amino-6-methoxyhex-4ynoic acid The starting amine 71c is coupled to 4-methoxybenzenesulfonyl chloride, and hydrolyzed as described for compounds 71d–e to give the title acid.

IX. Examples

Compositions and Methods of Use

The compounds of the invention are useful to prepare compositions for the treatment of ailments associated with unwanted MP activity. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

The following abbreviations are used in this section:
EDTA: ethylenediaminetetracetic acid
SDA: synthetically denatured alcohol
USP: United States Pharmacopoeia

Example A

A tablet composition for oral administration, according to the present invention, is made comprising:

| Component | Amount |
|---|---|
| The compound of Example 1 | 15 mg |
| Lactose | 120 mg |
| Maize Starch | 70 mg |
| Talc | 4 mg |
| Magnesium Stuart | 1 mg |

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
|---|---|
| The compound of Example 4 | 15% |
| Polyethylene glycol | 85% |

A human male subject weighing 90 kg (198 lbs.), suffering from osteoarthritis, is treated by a method of this invention. Specifically, for 5 years, a capsule containing 70 mg of the compound of Example 3 is administered daily to said subject.

At the end of the treatment period, the patient is examined via x-ray, arthroscopy and/or MRI, and found to have no further advancement of erosion/fibrillation of the articular cartilage.

Example C

A saline-based composition for local administration, according to the present invention, is made comprising:

| Component | Amount (% w/w) |
|---|---|
| The compound of Example 7 | 5% |
| Polyvinyl alcohol | 15% |
| Saline | 80% |

A patient having deep corneal abrasion applies the drop to each eye twice a day. Healing is speeded, with no visual sequelae.

Example D

A topical composition for local administration, according to the present invention, is made comprising:

| Component | Composition (% w/v) |
|---|---|
| The compound of Example 9 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

A patient suffering from chemical burns applies the composition at each dressing change (b.i.d.). Scarring is substantially diminished.

Example E

An inhalation aerosol compositions according to the present invention, is made comprising:

| Component | Composition (% w/v) |
|---|---|
| Compound of Example 13 | 5.0 |
| Alcohol | 33.0 |
| Ascorbic acid | 0.1 |
| Menthol | 0.1 |
| Sodium Saccharin | 0.2 |
| Propellant (F12,F114) | q.s. |
| Total = | 100.0 |

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 16 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

A human male subject weighing 90 kg (198 lbs), suffering from corneal ulcerations, is treated by a method of this invention. Specifically, for 2 months, a saline solution containing 10 mg of the compound of Example 16 is administered to said subject's affected eye twice-daily.

Example G

A composition for parenteral administration is made comprising:

| Component | Amount |
|---|---|
| The compound of Example 12 | 100 mg/mL carrier |
| Carrier: | |
| Sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Example H

A mouthwash composition is prepared:

| Component | % w/v |
|---|---|
| The compound of Example 14 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses 1 mL of the mouthwash thrice daily to prevent further oral degeneration.

Example I

A lozenge composition is prepared:

| Component | % w/v |
|---|---|
| The compound of Example 35 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the lozenge to prevent loosening of an implant in the maxilla.

Example J

Chewing Gum Composition

| Component | w/v % |
|---|---|
| The compound of Example 55 | 0.03 |
| Sorbitol crystals | 38.44 |
| Paloja-T gum base | 20.00 |
| Sorbitol (70% aqueous solution) | 22.00 |
| Mannitol | 10.00 |
| Glycerine | 7.56 |
| Flavor | 1.00 |

A patient chews the gum to prevent loosening of dentures.

Example K

| Components | w/v % |
|---|---|
| Compound of Example 28 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

The composition is prepared by first mixing 80 kg of glycerin and all of the benzyl alcohol and heating to 65° C., then slowly adding and mixing together methylparaben, propylparaben, water, xanthan gum, and guar gum. Mix these ingredients for about 12 minutes with a Silverson in-line mixer, Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes. The patient takes the formulation to prevent flare up of colitis.

Example L

An obese human female subject, who is determined to be prone to osteoarthritis, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

Example M

A human male subject weighing 90 kg (198 lbs.), who suffers a sports injury, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

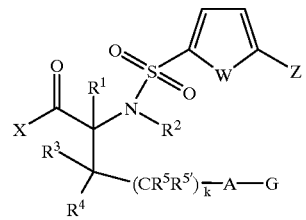

(I)

wherein (A) X is selected from —OH and —NHOH;

(B) W is selected from —S—, —O—, —N($R^{33}$)—, —C($R^{33}$)=C($R^{33'}$)—, —N=C($R^{33}$)—, and —N=N—, where $R^{33}$ and $R^{33'}$ each is independently selected from hydrogen, alkyl, alkenyl, alkynyl, heteroalkyl, aryl, heteroaryl, cycloalkyl, and heterocycloalkyl;

(C) $R^1$ is —(C$R^6R^{6'}$)$_l$—$R^{34}$, where l is from 0 to about 4; each $R^6$ and $R^{6'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{34}$ is selected from hydrogen, hydroxyl, alkoxy, alkyl, alkenyl, alkynyl, heteroalkyl, haloalkyl, cycloalkyl, heterocycloalkyl, aryl, heteroaryl, and halogen;

(D) $R^2$ is —(C$R^7R^{7'}$)$_m$—$R^{35}$ where m is from 0 to about 4; each $R^7$ and $R^{7'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{35}$ is selected from hydrogen, alkyl, alkenyl, alkynyl, heteroalkyl, haloalkyl, aryl, heteroaryl, cycloalkyl, and heterocycloalkyl;

(E) $R^3$ is —(C$R^8R^{8'}$)$_n$—$R^9$ where n is from 0 to about 4; each $R^8$ and $R^{8'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^9$ is selected from hydrogen, hydroxyl, alkoxy, alkyl, alkenyl, alkynyl, aryloxy, heteroalkyl, heteroaryloxy, haloalkyl, cycloalkyl, heterocycloalkyl, aryl, heteroaryl, and halogen;

(F) $R^4$ is —(C$R^{10}R^{10'}$)$_z$—A'—(C$R^{10''}R^{10'''}$)$_o$—$R^{11}$ where A' is selected from a covalent bond, —O—, —S— and $SO_2$; z is from 0 to about 4; o is from 0 to about 4; each $R^{10}$, $R^{10'}$, $R^{10''}$ and $R^{10'''}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{11}$ is selected from hydrogen, alkyl, alkenyl, alkynyl, heteroalkyl, haloalkyl, cycloalkyl, heterocycloalkyl, aryl, heteroaryl, and halogen;

(G) each $R^5$ and $R^{5'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and k is from 0 to about 4;

(H) A is selected from

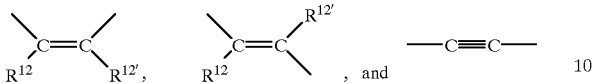

where $R^{12}$ and $R^{12'}$ each is independently selected from hydrogen, alkyl, alkenyl, alkynyl, haloalkyl, aryl, heteroalkyl, heteroaryl, heterocycloalkyl, cycloalkyl, halogen, and —C(=O)NR$^{13}$R$^{13'}$ where
  (1) $R^{13}$ and $R^{13'}$ each is independently selected from hydrogen, alkyl, alkenyl, alkynyl, heteroalkyl, aryl, and heteroaryl, or
  (2) $R^{13}$ and $R^{13'}$, together with the nitrogen atom to which they are bonded, join to form an optionally substituted heterocyclic ring containing from 5 to 8 ring atoms of which from 1 to 3 are heteroatoms;

(I) G is selected from
  (1) hydrogen;
  (2) —(CR$^{14}$R$^{14'}$)$_p$—R$^{15}$ where p is from 0 to about 4; each $R^{14}$ and $R^{14'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{15}$ is selected from hydrogen, alkyl, aryl, heteroaryl, cycloalkyl, heterocycloalkyl, arylalkyl, and heteroarylalkyl;
  (3) —(CR$^{16}$R$^{16'}$)$_q$—Y—(CR$^{17}$R$^{17'}$)$_r$—R$^{18}$ where q is from 1 to about 4 and r is from 0 to about 4; each $R^{16}$, $R^{16'}$, $R^{17}$, and $R^{17'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; Y is selected from —O— and —S—; and $R^{18}$ is selected from hydrogen, hydroxyl, alkoxy, alkyl, heteroalkyl, haloalkyl, cycloalkyl, heterocycloalkyl, aryl, and heteroaryl; provided that when r=0, $R^{18}$ is not hydroxyl or alkoxy;
  (4) —C(=O)NR$^{37}$R$^{37'}$ where (a) $R^{37}$ and $R^{37'}$ each is independently selected from hydrogen, alkyl, alkenyl, alkynyl, heteroalkyl, haloalkyl, aryl, heteroaryl, cycloalkyl, and heterocycloalkyl; or (b) $R^{37}$ and $R^{37'}$, together with the nitrogen atom to which they are bonded, join to form an optionally substituted heterocyclic ring containing from 5 to 8 ring atoms of which from 1 to 3 are heteroatoms; and
  (5) —(CR$^{19}$R$^{19'}$)$_s$—NR$^{20}$R$^{20'}$ where s is from 1 to about 4; each $R^{19}$ and $R^{19'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{20}$ and $R^{20'}$ each is independently selected from:
    (a) hydrogen, alkyl, alkenyl, alkynyl, heteroalkyl, haloalkyl, aryl, heteroaryl, cycloalkyl, and heterocycloalkyl;
    (b) —C(=O)R$^{21}$ where $R^{21}$ is selected from hydrogen, alkyl, alkenyl, alkynyl, heteroalkyl, haloalkyl, aryl, heteroaryl, cycloalkyl, and heterocycloalkyl; or $R^{21}$ and $R^{20}$, together with the amide group to which they are bonded, may join to form an optionally substituted heterocyclic ring containing from 5 to 8 ring atoms of which from 1 to 3 are heteroatoms;
    (c) —SO$_2$—(CR$^{22}$R$^{22'}$)$_t$—R$^{23}$ where t is from 0 to about 4; each $R^{22}$ and $R^{20'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and $R^{23}$ is selected from alkyl, heteroalkyl, haloalkyl, aryl, heteroaryl, cycloalkyl, and heterocycloalkyl; or $R^{23}$ and $R^{20}$, together with the sulfonamide group to which they are bonded, join to form an optionally substituted heterocyclic ring containing from 5 to 8 ring atoms of which from 1 to 3 are heteroatoms;
    (d) —C(=O)NR$^{24}$R$^{24'}$ where (i) $R^{24}$ and $R^{24'}$ are independently selected from hydrogen, alkyl, alkenyl, alkynyl, haloalkyl, heteroalkyl, aryl, heteroaryl, cycloalkyl, and heterocycloalkyl; or (ii) $R^{24}$ and $R^{24'}$, together with the nitrogen atom to which they are bonded, join to form an optionally substituted heterocyclic ring containing from 5 to 8 ring atoms of which from 1 to 3 are heteroatoms; and
    (e) —C(=O)OR$^{25}$ where $R^{25}$ is selected from alkyl, alkenyl, alkynyl, heteroalkyl, haloalkyl, aryl, heteroaryl, cycloalkyl, and heterocycloalkyl; or
    (f) $R^{20}$ and $R^{20'}$, together with the nitrogen atom to which they are bonded, join to form an optionally substituted heterocyclic ring containing from 5 to 8 ring atoms of which from 1 to 3 are heteroatoms; and (J) Z is selected from
  (1) cycloalkyl and heterocycloalkyl;
  (2) —D—(CR$^{26}$R$^{26'}$)$_u$R$^{27}$ where
    (a) u is from 0 to about 4;
    (b) D is selected from —C≡C—, —CH=CH—, —N=N—, —O—, —S— and —SO$_2$—;
    (c) each $R^{26}$ and $R^{26'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and
    (d) $R^{27}$ is selected from aryl, heteroaryl, alkyl, alkenyl, alkynyl, heteroalkyl, haloalkyl, heterocycloalkyl, cycloalkyl and, if D is —C≡C— or —CH=CH—, then $R^{27}$ may also be selected from —C(=O)NR$^{28}$R$^{28'}$ where (i) $R^{28}$ and $R^{28'}$ are independently selected from hydrogen, alkyl, alkenyl, alkynyl, haloalkyl, heteroalkyl, aryl, heteroaryl, cycloalkyl, and heterocycloalkyl, or (ii) $R^{28}$ and $R^{28'}$, together with the nitrogen atom to which they are bonded, join to form an optionally substituted heterocyclic ring containing from 5 to 8 ring atoms of which from 1 to 3 are heteroatoms;
  (3) —NR$^{29}$R$^{29'}$ where
    (a) $R^{29}$ and $R^{29'}$ each is independently selected from hydrogen; alkyl; alkenyl; alkynyl; heteroalkyl; haloalkyl; aryl; heteroaryl; cycloalkyl; heteroalkyl; and C(=O)—Q—(CR$^{30}$R$^{30'}$)$_v$R$^{31}$, where v is from 0 to about 4, Q is selected from a covalent bond and —N(R$^{32}$)—, each $R^{30}$ and $R^{30'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; $R^{31}$ and $R^{32}$ (i) each is independently selected from hydrogen, alkyl, alkenyl, alkynyl, heteroalkyl, haloalkyl, aryl, heteroaryl, cycloalkyl, and heterocycloalkyl, or (ii) $R^{31}$ and $R^{32}$, together with the nitrogen atom to which they are bonded, join to form an optionally substituted heterocyclic ring containing from 5 to 8 ring atoms of which from 1 to 3 are heteroatoms; or $R^{29}$ and $R^{32}$, together with the nitrogen atoms to which they are bonded, join to form an optionally substituted heterocyclic ring containing from 5 to 8 ring atoms of which from 1 to 3 are heteroatoms; or (b) $R^{29}$ and $R^{29'}$, together with the nitrogen atom to which they are bonded, join to form an optionally substituted heterocyclic ring containing from 5 to 8 ring atoms of which from 1 to 3 are heteroatoms; and

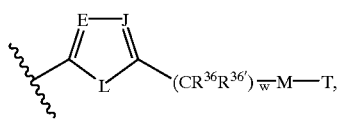
(4)

where
(a) E and J are independently selected from —CH— and —N—;
(b) L is selected from —S—, —O—, —N($R^{38}$)—, —C($R^{38}$)=C($R^{38'}$)—, N=C($R^{38}$)—, and —N=N—, where $R^{38}$ and $R^{38'}$ each is independently selected from hydrogen, alkyl, alkenyl, alkynyl, heteroalkyl, aryl, heteroaryl, cycloalkyl, and heterocycloalkyl;
(c) w is from 0 to about 4;
(d) each $R^{36}$ and $R^{36'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;
(e) M is selected from a covalent bond, —O—, —SO$_x$—, —C(O)—, —C(=O)N$R^{39}$—, —N($R^{39}$)—, and —N($R^{39}$)C(=O)—; where x is from 0 to 2; and $R^{39}$ is selected from hydrogen, alkyl, alkenyl, alkynyl, aryl, heteroaryl, heteroalkyl, heteroaryl, cycloalkyl, heterocycloalkyl, and haloalkyl; and
(f) T is —(C$R^{40}R^{40'}$)$_y$—$R^{41}$ where y is from 0 to about 4; each $R^{40}$ and $R^{40'}$ is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy; and $R^{41}$ is selected from hydrogen, alkyl, alkenyl, alkynyl, halogen, heteroalkyl, haloalkyl, aryl, heteroaryl, cycloalkyl, and heterocycloalkyl; or $R^{39}$ and $R^{41}$, together with the atoms to which they are bonded, join to form an optionally substituted heterocyclic ring containing from 5 to 8 atoms of which 1 to 3 are heteroatoms; or $R^{38}$ and $R^{41}$, together with the atoms to which they are bonded, join to form an optionally substituted heterocyclic ring containing from 5 to 8 atoms of which 1 to 3 are heteroatoms;

or an optical isomer, diastereomer or enantiomer for Formula (I), or a pharmaceutically-acceptable salt, or biohydrolyzable amide, ester, or imide thereof.

2. The compound of claim 1 wherein A is —C≡C—.
3. The compound of claim 1 wherein W is selected from —S— and —CH=CH—.
4. The compound of claim 3 wherein Z is selected from —D—(C$R^{26}R^{26'}$)$_u$$R^{27}$;

—N$R^{29}R^{29'}$; and

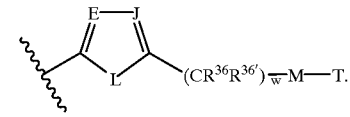

5. The compound of claim 4 wherein Z is —D—(C$R^{26}R^{26'}$)$_u$$R^{27}$ where D is selected from —C≡C—, —C=C— and —N=N—, u is 0, and $R^{27}$ is selected from aryl, heteroaryl, heterocycloalkyl and cycloalkyl.
6. The compound of claim 4 wherein Z is —N$R^{29}R^{29'}$ wherein $R^{29}$ is hydrogen and $R^{29'}$ is —C(O)—Q—(C$R^{30}R^{30'}$)$_v$$R^{31}$ where Q is a covalent bond and v is 0.
7. The compound of claim 6 wherein $R^{31}$ is selected from aryl, heteroaryl, cycloalkyl, and heterocycloalkyl.
8. The compound of claim 4 wherein Z is

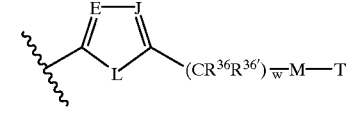

where E and J are both —CH—, w is 0, L is —C($R^{38'}$)=C($R^{38}$)— and $R^{38}$ and T join to form an optionally substituted 5-membered ring containing from 0 to 2 ring heteroatoms.
9. The compound of claim 4 wherein Z is

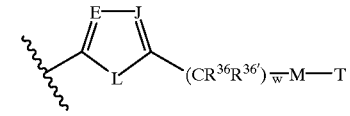

and wherein E and J are both —CH—, w is 0, and L is —HC=CH—.
10. The compound of claim 4 wherein M is selected from covalent bond, —O— and —S—.
11. The compound of claim 4 wherein T is —(C$R^{40}R^{40'}$)$_y$—$R^{41}$ where y is 0 and $R^{41}$ is selected from alkyl, heteroalkyl, aryl, heteroaryl, cycloalkyl and heterocycloalkyl.
12. The compound of claim 1 wherein k is 0.
13. The compound of claim 12 wherein $R^4$ is —(C$R^{10}R^{10'}$)$_z$—A'—(C$R^{10''}R^{10'''}$)$_o$—$R^{11}$ where A' is a covalent bond or —O—; o is 0 or 1; z is 0 or 1; each $R^{10}$, $R^{10'}$, and $R^{10'''}$ is hydrogen; and $R^{11}$ is selected from hydrogen, alkyl, heteroalkyl, haloalkyl, cycloalkyl, heterocycloalkyl, aryl, and heteroaryl.
14. The compound of claim 12 wherein A is selected from

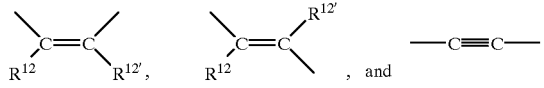

where $R^{12}$ and $R^{12'}$ each is independently selected from hydrogen, alkyl, aryl, heteroalkyl, heteroaryl, heterocycloalkyl, and cycloalkyl.
15. The compound of claim 12 wherein G is selected from
(1) hydrogen;
(2) —(C$R^{14}R^{14'}$)$_p$—$R^{15}$ where p is 0 or 1; each $R^{14}$ and $R^{14'}$ is hydrogen; and $R^{15}$ is selected from alkyl, aryl, heteroaryl, cycloalkyl, and heterocycloalkyl;

101

(3) —(CR$^{16}$R$^{16'}$)$_q$—Y—(CR$^{17}$R$^{17'}$)$_r$—R$^{18}$ where q is 1 and r is 0 or 1; each R$^{16}$, R$^{16'}$, R$^{17}$, and R$^{17'}$ is hydrogen; Y is selected from —O— and —S—; and R$^{18}$ is selected from hydrogen, alkyl, heteroalkyl, cycloalkyl, heterocycloalkyl, aryl, and heteroaryl; and (4) —(CR$^{19}$R$^{19'}$)$_s$—NR$^{20}$R$^{20'}$ where s is 1; each R$^{19}$ and R$^{19'}$ is hydrogen; and R$^{20}$ and R$^{20'}$ each is independently selected from:

(a) hydrogen, alkyl, heteroalkyl, aryl, heteroaryl, cycloalkyl, and heterocycloalkyl;

(b) —C(=O)R$^{21}$ where R$^{21}$ is selected from hydrogen, alkyl, heteroalkyl, aryl, heteroaryl, cycloalkyl, and heterocycloalkyl; or R$^{21}$ and R$^{20}$, together with the amide group to which they are bonded, may join to form an optionally substituted heterocyclic ring containing 5 or 6 ring atoms of which 1 or 2 are heteroatoms; and (c) —SO$_2$—(CR$^{22}$R$^{22'}$)$_t$—R$^{23}$ where t is 0 and R$^{23}$ is selected from alkyl, aryl, and heteroaryl; or (d) R$^{20}$ and R$^{20'}$, together with the nitrogen atom to which they are bonded, join to form an optionally substituted heterocyclic ring containing 5 or 6 ring atoms of which 1 or 2 are heteroatoms.

16. A compound having a structure according to Formula (II)

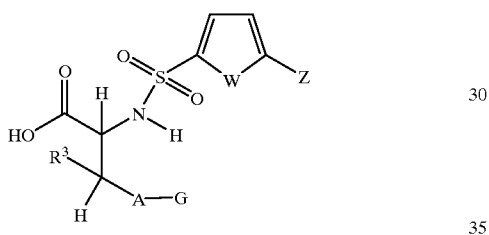

(II)

wherein (A) W is selected from —S—, —O—, —N(R$^{33}$)—, —C(R$^{33}$)=C(R$^{33'}$)—, —N=C(R$^{33}$)—, and —N=N—, where R$^{33}$ and R$^{33'}$ each is independently selected from hydrogen, alkyl, alkenyl, alkynyl, heteroalkyl, aryl, heteroaryl, cycloalkyl, and heterocycloalkyl;

(B) R$^4$ is —(CR$^{10}$R$^{10'}$)$_z$—A'—(CR$^{10''}$R$^{10'''}$)$_o$—R$^{11}$ where A' is selected from a covalent bond, —O—, —S— and SO$_2$; z is from 0 to about 4; o is from 0 to about 4; each R$^{10}$, R$^{10'}$, R$^{10''}$ and R$^{10'''}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and R$^{11}$ is selected from hydrogen, alkyl, alkenyl, alkynyl, heteroalkyl, haloalkyl, cycloalkyl, heterocycloalkyl, aryl, heteroaryl, and halogen;

(C) A is selected from

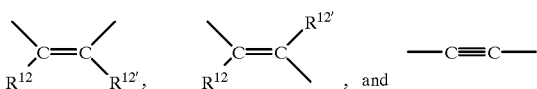

where R$^{12}$ and R$^{12'}$ each is independently selected from hydrogen, alkyl, alkenyl, alkynyl, haloalkyl, aryl, heteroalkyl, heteroaryl, heterocycloalkyl, cycloalkyl, halogen, and —C(=O)NR$^{13}$R$^{13'}$ where (1) R$^{13}$ and R$^{13'}$ each is independently selected from hydrogen, alkyl, alkenyl, alkynyl, heteroalkyl, aryl, and heteroaryl, or

102

(2) R$^{13}$ and R$^{13'}$, together with the nitrogen atom to which they are bonded, join to form an optionally substituted heterocyclic ring containing from 5 to 8 ring atoms of which from 1 to 3 are heteroatoms;

(D) G is selected from (1) hydrogen;

(2) —(CR$^{14}$R$^{14'}$)$_p$—R$^{15}$ where p is from 0 to about 4; each R$^{14}$ and R$^{14'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and R$^{15}$ is selected from hydrogen, alkyl, aryl, heteroaryl, cycloalkyl, heterocycloalkyl, arylalkyl, and heteroarylalkyl;

(3) —(CR$^{16}$R$^{16'}$)$_q$—Y—(CR$^{17}$R$^{17'}$)$_r$—R$^{18}$ where q is from 1 to about 4 and r is from 0 to about 4; each R$^{16}$, R$^{16'}$, R$^{17}$, and R$^{17'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; Y is selected from —O— and —S—; and R$^{18}$ is selected from hydrogen, hydroxyl, alkoxy, alkyl, heteroalkyl, haloalkyl, cycloalkyl, heterocycloalkyl, aryl, and heteroaryl; provided that when r=0, R$^{18}$ is not hydroxyl or alkoxy;

(4) —C(=O)NR$^{37}$R$^{37'}$ where (a) R$^{37}$ and R$^{37'}$ each is independently selected from hydrogen, alkyl, alkenyl, alkynyl, heteroalkyl, haloalkyl, aryl, heteroaryl, cycloalkyl, and heterocycloalkyl; or (b) R$^{37}$ and R$^{37'}$, together with the nitrogen atom to which they are bonded, join to form an optionally substituted heterocyclic ring containing from 5 to 8 ring atoms of which from 1 to 3 are heteroatoms; and (5) —(CR$^{19}$R$^{19'}$)$_s$—NR$^{20}$R$^{20'}$ where s is from 1 to about 4; each R$^{19}$ and R$^{19'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and R$^{20}$ and R$^{20'}$ each is independently selected from:

(a) hydrogen, alkyl, alkenyl, alkynyl, heteroalkyl, haloalkyl, aryl, heteroaryl, cycloalkyl, and heterocycloalkyl;

(b) —C(=O)R$^{21}$ where R$^{21}$ is selected from hydrogen, alkyl, alkenyl, alkynyl, heteroalkyl, haloalkyl, aryl, heteroaryl, cycloalkyl, and heterocycloalkyl; or R$^{21}$ and R$^{20}$, together with the amide group to which they are bonded, may join to form an optionally substituted heterocyclic ring containing from 5 to 8 ring atoms of which from 1 to 3 are heteroatoms;

(c) —SO$_2$—(CR$^{22}$R$^{22'}$)$_t$—R$^{23}$ where t is from 0 to about 4; each R$^{22}$ and R$^{22'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and R$^{23}$ is selected from alkyl, heteroalkyl, haloalkyl, aryl, heteroaryl, cycloalkyl, and heterocycloalkyl; or R$^{23}$ and R$^{20}$, together with the sulfonamide group to which they are bonded, join to form an optionally substituted heterocyclic ring containing from 5 to 8 ring atoms of which from 1 to 3 are heteroatoms;

(d) —C(=O)NR$^{24}$R$^{24'}$ where (i) R$^{24}$ and R$^{24'}$ are independently selected from hydrogen, alkyl, alkenyl, alkynyl, haloalkyl, heteroalkyl, aryl, heteroaryl, cycloalkyl, and heterocycloalkyl; or (ii) R$^{24}$ and R$^{24'}$, together with the nitrogen atom to which they are bonded, join to form an option-

103 ally substituted heterocyclic ring containing from 5 to 8 ring atoms of which from 1 to 3 are heteroatoms; and (e) —C(=O)OR$^{25}$ where R$^{25}$ is selected from alkyl, alkenyl, alkynyl, heteroalkyl, haloalkyl, aryl, heteroaryl, cycloalkyl, and heterocycloalkyl; or (f) R$^{20}$ and R$^{20'}$, together with the nitrogen atom to which they are bonded, join to form an optionally substituted heterocyclic ring containing from 5 to 8 ring atoms of which from 1 to 3 are heteroatoms; and (E) Z is selected from
(1) cycloalkyl and heterocycloalkyl;
(2) —D—(CR$^{26}$R$^{26'}$)$_u$R$^{27}$ where
   (a) u is from 0 to about 4;
   (b) D is selected from —C≡C—, —CH=CH—, —N=N—, —O—, —S— and —SO$_2$—;
   (c) each R$^{26}$ and R$^{26'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; and
   (d) R$^{27}$ is selected from aryl, heteroaryl, alkyl, alkenyl, alkynyl, heteroalkyl, haloalkyl, heterocycloalkyl, cycloalkyl and, if D is —C≡C— or —CH=CH—, then R$^{27}$ may also be selected from —C(=O)NR$^{28}$R$^{28'}$ where (i) R$^{28}$ and R$^{28'}$ are independently selected from hydrogen, alkyl, alkenyl, alkynyl, haloalkyl, heteroalkyl, aryl, heteroaryl, cycloalkyl, and heterocycloalkyl, or (ii) R$^{28}$ and R$^{28'}$, together with the nitrogen atom to which they are bonded, join to form an optionally substituted heterocyclic ring containing from 5 to 8 ring atoms of which from 1 to 3 are heteroatoms;
(3) —NR$^{29}$R$^{29'}$ where
   (a) R$^{29}$ and R$^{29'}$ each is independently selected from hydrogen; alkyl; alkenyl; alkynyl; heteroalkyl; haloalkyl; aryl; heteroaryl; cycloalkyl; heteroalkyl; and C(=O)—Q—(CR$^{30}$R$^{30'}$)$_v$R$^{31}$, where v is from 0 to about 4, Q is selected from a covalent bond and —NR$^{32}$—, each R$^{30}$ and R$^{30'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy; R$^{31}$ and R$^{32}$ (i) each is independently selected from hydrogen, alkyl, alkenyl, alkynyl, heteroalkyl, haloalkyl, aryl, heteroaryl, cycloalkyl, and heterocycloalkyl, or (ii) R$^{31}$ and R$^{32}$, together with the nitrogen atom to which they are bonded, join to form an optionally substituted heterocyclic ring containing from 5 to 8 ring atoms of which from 1 to 3 are heteroatoms; or R$^{29}$ and R$^{32}$, together with the nitrogen atoms to which they are bonded, join to form an optionally substituted heterocyclic ring containing from 5 to 8 ring atoms of which from 1 to 3 are heteroatoms; or
   (b) R$^{29}$ and R$^{29'}$, together with the nitrogen atom to which they are bonded, join to form an optionally substituted heterocyclic ring containing from 5 to 8 ring atoms of which from 1 to 3 are heteroatoms; and

104

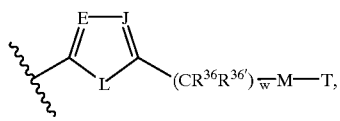

(4)

where
(a) E and J are independently selected from —CH— and —N—;
(b) L is selected from —S—, —O—, —N(R$^{38}$)—, —C(R$^{38}$)=C(R$^{38'}$)—, —N=C(R$^{38}$)—, and —N=N—, where R$^{38}$ and R$^{38'}$ each is independently selected from hydrogen, alkyl, alkenyl, alkynyl, heteroalkyl, aryl, heteroaryl, cycloalkyl, and heterocycloalkyl;
(c) w is from 0 to about 4;
(d) each R$^{36}$ and R$^{36'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy;
(e) M is selected from a covalent bond, —O—, —SO$_x$—, —C(=O)—, —C(=O)N(R$^{39}$)—, —N(R$^{39}$)—, and —N(R$^{39}$)C(=O)—; where x is from 0 to 2; and R$^{39}$ is selected from hydrogen, alkyl, alkenyl, alkynyl, aryl, heteroaryl, heteroalkyl, heteroaryl, cycloalkyl, heterocycloalkyl, and haloalkyl; and
(f) T is —(CR$^{40}$R$^{40'}$)$_y$—R$^{41}$ where y is from 0 to about 4; each R$^{40}$ and R$^{40'}$ is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy; and R$^{41}$ is selected from hydrogen, alkyl, alkenyl, alkynyl, halogen, heteroalkyl, haloalkyl, aryl, heteroaryl, cycloalkyl, and heterocycloalkyl; or R$^{39}$ and R$^{41}$, together with the atoms to which they are bonded, join to form an optionally substituted heterocyclic ring containing from 5 to 8 atoms of which 1 to 3 are heteroatoms; or R$^{38}$ and R$^{41}$, together with the atoms to which they are bonded, join to form an optionally substituted heterocyclic ring containing from 5 to 8 atoms of which 1 to 3 are heteroatoms;

or an optical isomer, diastereomer or enantiomer for Formula (I), or a pharmaceutically-acceptable salt, or biohydrolyzable amide, ester, or imide thereof.

17. The compound of claim 16 wherein (A) W is selected from —S— and —CH=CH—;
(B) R$^4$ is —(CR$^{10}$R$^{10'}$)$_z$—A'—(CR$^{10''}$R$^{10'''}$)$_o$—R$^{11}$ where A' is covalent bond or —O—; o is 0 or 1; z is 0 or 1; each R$^{10}$, R$^{10'}$, R$^{10''}$ and R$^{10'''}$ is hydrogen; and R$^{11}$ is selected from hydrogen, alkyl, heteroalkyl, haloalkyl, cycloalkyl, heterocycloalkyl, aryl, and heteroaryl;
(C) A is selected from

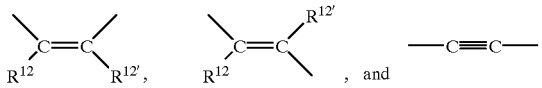

where R$^{12}$ and R$^{12'}$ each is independently selected from hydrogen, alkyl, aryl, heteroalkyl, heteroaryl, heterocycloalkyl, and cycloalkyl; and (D) G is selected from
(1) hydrogen;
(2) —(CR$^{14}$R$^{14'}$)$_p$—R$^{15}$ where p is 0 or 1; each R$^{14}$ and R$^{14'}$ is hydrogen; and R$^{15}$ is selected from alkyl, aryl, heteroaryl, cycloalkyl, and heterocycloalkyl;
(3) —(CR$^{16}$R$^{16'}$)$_q$—Y—(CR$^{17}$R$^{17'}$)$_r$—R$^{18}$ where q is 1 and r is 0 or 1; each R$^{16}$, R$^{16'}$, R$^{17}$, and R$^{17'}$ is hydrogen; Y is selected from —O— and —S—; and R$^{18}$ is selected from hydrogen, alkyl, heteroalkyl, cycloalkyl, heterocycloalkyl, aryl, and heteroaryl; and
(4) —(CR$^{19}$R$^{19'}$)$_s$—NR$^{20}$R$^{20'}$ where s is 1; each R$^{19}$ and R$^{19'}$ is hydrogen; and R$^{20}$ and R$^{20'}$ each is independently selected from:
(a) hydrogen, alkyl, heteroalkyl, aryl, heteroaryl, cycloalkyl, and heterocycloalkyl;
(b) —C(=O)R$^{21}$ where R$^{21}$ is selected from hydrogen, alkyl, heteroalkyl, aryl, heteroaryl, cycloalkyl, and heterocycloalkyl; or R$^{21}$ and R$^{20}$, together with the amide group to which they are bonded, may join to form an optionally substituted heterocyclic ring containing 5 or 6 ring atoms of which 1 or 2 are heteroatoms; and
(c) —SO$_2$—(CR$^{22}$R$^{22'}$)$_t$—R$^{23}$ where t is 0 and R$^{23}$ is selected from alkyl, aryl, and heteroaryl; or
(d) R$^{20}$ and R$^{20'}$, together with the nitrogen atom to which they are bonded, join to form an optionally substituted heterocyclic ring containing 5 or 6 ring atoms of which 1 or 2 are heteroatoms.

18. The compound of claim 17 wherein Z is selected from
—D—(CR$^{26}$R$^{26'}$)$_u$R$^{27}$;
—NR$^{29}$R$^{29'}$; and

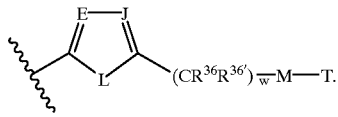

19. The compound of claim 18 wherein Z is —D—(CR$^{26}$R$^{26'}$)$_u$R$^{27}$ where D is selected from —C≡C—, —C=C— and —N=N—, u is 0, and R$^{27}$ is selected from aryl, heteroaryl, heterocycloalkyl and cycloalkyl.

20. The compound of claim 17 wherein Z is —NR$^{29}$R$^{29'}$ wherein R$^{29}$ is hydrogen and R$^{29'}$ is —C(O)—Q—(CR$^{30}$R$^{30'}$)$_v$R$^{31}$ where Q is a covalent bond and v is 0.

21. The compound of claim 20 wherein R$^{31}$ is selected from aryl, heteroaryl, cycloalkyl, and heterocycloalkyl.

22. The compound of claim 18 wherein Z is

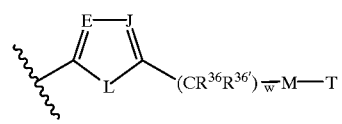

where E and J are both —CH—, w is 0, L is —C(R$^{38'}$)=C(R$^{38}$)— and R$^{38}$ and T join to form an optionally substituted 5-membered ring containing from 0 to 2 ring heteroatoms.

23. The compound of claim 18 wherein Z is

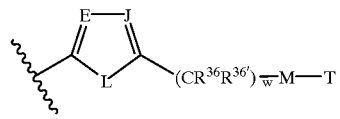

and wherein E and J are both —CH—, w is 0, and L is —HC=CH—.

24. The compound of claim 17 wherein M is selected from covalent bond, —O— and —S—.

25. The compound of claim 17 wherein T is —(CR$^{40}$R$^{40'}$)$_y$—R$^{41}$ where y is 0 and R$^{41}$ is selected from alkyl, heteroalkyl, aryl, heteroaryl, cycloalkyl and heterocycloalkyl.

26. A compound selected from the group consisting of:
2-{[4'-Fluoro-(1,1'-biphenyl)-4-yl]-sulfonyl}-amino-5-phenylpent-4-ynoic acid;
2-(4-Phenyloxyphenylsulfonyl)-amino-5-phenylpent-4-ynoic acid;
2-{[4'-Methoxy-(1,1'-biphenyl)-4-yl]-sulfonyl}-amino-5-phenylpent-4-ynoic acid;
2-{[4'-Methoxy-(1,1'-biphenyl)-4-yl]-sulfonyl}-amino-5-(4-morpholino-phenyl)-pent-4-ynoic acid;
2-{[4'-Methoxy-(1,1'-biphenyl)-4-yl]-sulfonyl}-amino-5-(3-morpholinophenyl)-pent-4-ynoic acid;
2-{[(1,1'-4',1"-Triphenyl)-4-yl]-sulfonyl}-amino-5-phenylpent-4-ynoic acid;
2-{[4'-Methylthio-(1,1'-biphenyl)p-4-yl]-sulfonyl}-amino-5-phenylpent-4-ynoic acid,
2-{[3',4'-Methylenedioxy-(1,1'-biphenyl)-4-yl]-sulfonyl}-amino-5-phenylpent-4-ynoic acid;
2-{[4'-Phenyloxy-(1,1'-biphenyl)-4-yl]-sulfonyl}-amino-5-phenylpent-4-ynoic acid;
2-{[4'-(2-Methoxyethoxy)-(1,1'-biphenyl)-4-yl]-sulfonyl}-3-amino-5-phenylpent-4-ynoic acid;
2-{[4'-(2-N-pyrrolidino-ethoxy)-(1,1'-biphenyl)-4-yl]-sulfonyl}-amino-5-phenylpent-4-ynoic acid;
2-{[3'-Ethoxy-(1,1'-biphenyl)-4-yl]-sulfonyl}-amino-5-phenylpent-4-ynoic acid;
2-[4-(4-Methylphenyl)-acetylenylbenzene sulfonyl]-amino-5-phenyl-pent-4-ynoic acid;
2-[4-(4-Methoxyphenyl)-acetylenylbenzene sulfonyl]-amino-5-phenyl-pent-4-ynoic acid;
2-(4-Phenylazobenzenesulfonyl)-amino-5-phenylpentynoic acid,
2-{[4'-Phenyloxy(1,1'-biphenyl)-4-yl]-sulfonyl}-amino-5-(pyridin-3-yl)-pent-4-ynoic acid;
2-[4-(4-Methoxyphenyl)-acetylenylbenzene sulfonyl]-amino-5-(pyridin-3-yl)-pent-4-ynoic acid;
2-{[4'-Methoxy-(1,1'-biphenyl)-4-yl]-sulfonyl}-amino-5-(pyridin-3-yl)-pent-4-ynoic acid;
2-{[4'-Methoxy-(1,1'-biphenyl)-4-yl]-sulfonyl}-amino-5-(furan-2-yl)-pent-4-ynoic acid;
2-{[4'-(2-Methoxyethoxy)-(1,1'-biphenyl)-4-yl]-sulfonyl}-amino-5-(furan-2-yl)-pent-4-ynoic acid;
2-{[4'-(2-N-pyrrolidino-ethoxy)-(1,1'-biphenyl)-4-yl]-sulfonyl}-amino-5-(furan-2-yl)-pent-4-ynoic acid;
2-{[4'-Methoxy-(1,1'-biphenyl)-4-yl]-sulfonyl}-amino-5-(thiophen-2-yl)-pent-4-ynoic acid;
-{[4'-Methoxy-(1,1'-biphenyl)-4-yl]-sulfonyl)-amino-5-(N-methylpyrrol-2-yl)-pent-4-ynoic acid;

2-(4-n-Butoxybenzene)-sulfonylamino-5-phenylpent-4-ynoic acid;

2-{[5-(4-Methoxyphenyl)-thiophen-2-yl]-sulfonyl}-amino-5-phenyl-pent-4-ynoic acid;

2-{[5-(4-methoxyphenylacetylenyl)-thiophen-2-yl]-sulfonyl}-amino-5-phenyl-pent-4-ynoic acid;

2-{[(4-benzenesulphonyl)-thiophen-2-yl]-sulphonyl}-amino-5-phenylpent-4-ynoic acid;

2-{[(5-benzenesulphonyl)-thiophen-2-yl]-sulphonyl}-amino-5-phenylpent-4-ynoic acid;

2-{[5-(4-Methoxyphenyl)-thiophen-2-yl]-sulfonyl}-amino-5-(3-N-morpholino)-phenylpent-4-ynoic acid;

2-{[5-(4-Methoxyphenyl)-thiophen-2-yl]-sulfonyl}-amino-5-(3-N,N-dimethylamino)-phenylpent-4-ynoic acid;

2-[(1,1'-Biphenyl-4-yl)-sulfonyl]-amino-6-pyrrolidinohex-4-ynoic acid;

2-{[4'-Methoxy(1,1'-biphenyl)-4-yl]-sulfonyl}-amino-6-pyrrolidinohex-4-ynoic acid, 2-[(1,1'-Biphenyl)-4-yl-sulfonyl]-amino-6-morpholinohex-4-ynoic acid;

2-{[4'-Methoxy-(1,1'-biphenyl)-4-yl]-sulfonyl}-amino-6-morpholinohex-4-ynoic acid;

2-{[4'-Methylthio-(1,1'-biphenyl)-4-yl]-sulfonyl}-amino-6-morpholinohex-4-ynoic acid;

2-[4-(4-Methoxyphenyl)-acetylenylbenzenesulfonyl]-amino-6-morpholinohex-4-ynoic acid;

2-{[4'-Phenyloxy-(1,1'-biphenyl)-4-yl]-sulfonyl}-amino-6-morpholinohex-4-ynoic acid;

2-{[4'-Methoxy-(1,1'-biphenyl)-4-yl]-sulfonyl}-amino-6-(4N-acetylpiperazin-1N-yl)-hex-4-ynoic acid;

4'-Methoxy-(1,1'-biphenyl)-4-yl]-sulfonyl}-amino-6-(4N-methanesulfonylpiperazin-1N-yl)-hex-4-ynoic acid;

2-{[4'-Methoxy-(1,1'-biphenyl)-4-yl]-sulfonyl}-amino-6-(4N-tert-butoxycarbonylpiperazin-1N-yl)-hex-4-ynoic acid;

2-{[4'-Methoxy-(1,1'-biphenyl)-4-yl]-sulfonyl}-amino-6-(4N-phenylpiperazin-1N-yl)-hex-4-ynoic acid;

2-{[4'-Phenyloxy-(1,1'-biphenyl)-4-yl]-sulfonyl}-amino-6-pyrrolidinohex-4-ynoic acid;

2-{[4'-Phenyloxy-(1,1'-biphenyl)-4-yl]-sulfonyl)-amino-6-(N,N-dimethylamino)-hex-4-ynoic acid;

2-[4-(N-4-Methoxybenzoyl)-aminobenzenesulfonyl]-amino-6-morpholinohex-4-ynoic acid;

2-[4-(N-4-n-Butoxybenzoyl)-aminobenzenesulfonyl]-amino-6-morpholinohex-4-ynoic acid;

2-{[4'-Methoxy-(1,1'-biphenyl)-4-yl]-sulfonyl}-amino-6-phenylhex-4-ynoic acid;

2-{[4'-(2-Methoxyethoxy)-(1,1'-biphenyl)-4-yl]-sulfonyl}-amino-6-phenylhex-4-ynoic acid;

2-{[4'-(2-N-Pyrrolidino-ethoxy)-(1,1'-biphenyl)-4-yl]-sulfonyl}-amino-6-phenylhex-4-ynoic acid;

2-{[4'-Methoxy-(1,1'-biphenyl)-4-yl]-sulfonyl}-amino-6-phenyloxyhex-4-ynoic acid;

2-{[4'-Methoxy-(1,1'-biphenyl)-4-yl]-sulfonyl}-amino-6-methoxyhex-4-ynoic acid;

2-{[4'-Bromo-(1,1'-biphenyl)-4-yl]-sulfonyl}-amino-6-methoxyhex-4-ynoic acid;

2-{[4'-Methoxy-(1,1'-biphenyl)-4-yl]-sulfonyl-N-methyl}-amino-6-methoxyhex-4-ynoic acid;

2-{[4'-Methoxy-(1,1'-biphenyl)-4-yl]-sulfonyl}-amino-6-(2-methoxyethoxy)-methoxyhex-4-ynoic acid;

2-{[4'-Bromo-(1,1'-bipbenyl)-4-yl]-sulfonyl}-amino-6-phenyloxy-4-ynoic acid;

2-{[4'-Phenyloxy-(1,1'-biphenyl)-4-yl]-sulfonyl}-amino-6-methoxyhex-4-ynoic acid;

2-{[4'-Methoxy-(1,1'-biphenyl)-4-yl]-sulfonyl}-amino-6-phenylthiohex-4-ynoic acid;

2-{[4'-Methoxy-(1,1'-biphenyl)-4-yl]-sulfonyl}-amino-6-[5-(furan-2-yl)-oxadiazol-2-yl]-thiohex-4-ynoic acid;

2-{[4'-Methoxy-(1,1'-biphenyl)-4-yl]-sulfonyl}-amino-6-[5-(N-pyrrolidinyl)-thiadiazol-2-yl]-thiohex-4-ynoic acid;

trans-2-{[4'-Methoxy-(1,1'-biphenyl)-4-yl]-sulfonyl}-amino-5-phenylpent-4-enoic acid;

2-{[4'-Methoxy-(1,1'-biphenyl)-4-yl]-sulfonyl}-amino-3-benzyloxymethyl-pent-4-enoic acid;

2-[(1,1'-biphenyl)-4-yl]-sulfonyl-amino-3-benzyloxymethyl-pent-4-enoic acid;

cis-2-{[4'-Methoxy-(1,1'-biphenyl)-4-yl]-sulfonyl}-amino-5-(N-pyrrolidinocarbonyl)-pent-4-enoic acid;

(2R)-{[4'-Methoxy-(1,1'-biphenyl)-4-yl]-sulfonyl)-amino-(3S)-methoxy-5-phenylpent-4-ynoic acid;

(2R)-{[4'-Thiomethoxy-(1,1'-biphenyl)-4-yl]-sulfonyl}-amino-(3S)-methoxy-5-phenylpent-4-ynoic acid;

(2R)-{[4'-Methoxy-(1,1'-biphenyl)-4-yl]-sulfonyl}-amino-(3S)-benzyloxy-5-phenylpent-4-ynoic acid;

(2R)-{[4'-Methoxy-(1,1'-biphenyl)-4-yl]-sulfonyl}-amino-(3 S)-(2-methoxyethoxy)-5-phenylpent-4-ynoic acid;

(2R)-{[4'-Phenyloxy-(1,1'-biphenyl)-4-yl]-sulfonyl}-amino-(3S)-(2-methoxyethoxy)-5-phenylpent-4-ynoic acid;

(2R)-{[4'-Methoxy-(1,1'-biphenyl)-4yl]-sulfonyl}-amino-(3S)-(2-methoxyethoxy)-5-phenylthiomethyl-pent-4-ynoic acid;

2-{[4-(4-Chlorobenzoyl)amino]-benzenesulfonyl}-amino-5-phenylpent-4-ynoic acid,

2-{[4-(4-Methoxybenzoyl)amino]-benzenesulfonyl}-amino-5-phenylpent-4-ynoic acid;

2-{[4-(5-n-propylpyridin-2-oyl)-amino]-benzenesulfonyl}-amino-5-phenylpent-4-ynoic acid, 2-{[4-(6-N-pyrrolylpyridin-3-oyl)-amino]-benzenesulfonyl}-amino-5-phenylpent-4-ynoic acid;

2-{[4-(4-Methoxybenzoyl)amino]-benzenesulfonyl}-amino-6-phenyloxyhex-4-ynoic acid;

2-{[4-(6-trifluoromethylpyridin-3-oyl)-amino]-benzenesulfonyl}-amino-6-phenyloxyhex-4-ynoic acid;

2-{[4-(6-cyanopyridin-3-oyl)-amino]-benzenesulfonyl}-amino-6-phenyloxyhex-4-ynoic acid, 2-{[4-(6-trifluoromethylmethoxypyridin-3-oyl)-amino]-benzenesulfonyl}-amino-6-phenyloxyhex-4-ynoic acid;

2-{[4-(5-methylpyrizin-2-oyl)-amino]-benzenesulfonyl}-amino-6-phenyloxyhex-4-ynoic acid;

2-{[4-(5-methoxyindol-2-oyl)-amino]-benzenesulfonyl}-amino-6-phenyloxyhex-4-ynoic acid;

2-{[4-(1N-methylindol-2-oyl)-amino]-benzenesulfonyl}-amino-6-phenyloxyhex-4-ynoic acid;

2-{[4-(N-morpholinocarbonyl)-amino]-benzenesulfonyl}-amino-5-phenylpent-4-ynoic acid;

2-{[4-(N-morpholinocarbonyl)-amino]-benzenesulfonyl-amino-5-phenyloxyhex-4-ynoic acid;

2-{[4-(N-pyrrolidinocarbonyl)-amino]-benzenesulfonyl}-amino-5-phenylpent-4-ynoic acid;

2-{[4-(N-phenylaminocarbonyl)-amino]-benzenesulfonyl}-amino-5-phenylpent-4-ynoic acid;

2-{[4-(N,N-methylphenylaminocarbonyl)-amino]-benzenesulfonyl}-amino-5-phenylpent-4-ynoic acid;

2-{[4-(N-[4-methyloxazol-2-yl]-carbonyl)-amino]-benzenesulfonyl}-amino-5-phenylpent-4-ynoic acid; and 2-{[4-(N-[benzthiazol-2-yl]-carbonyl)-amino]-benzenesulfonyl}-amino-5-phenylpent-4-ynoic acid.

27. A pharmaceutical composition comprising:
(a) a safe and effective amount of a compound of claim 1; and
(b) a pharmaceutically-acceptable carrier.

28. A pharmaceutical composition comprising:
(a) a safe and effective amount of a compound of claim 3; and
(b) a pharmaceutically-acceptable carrier.

29. A pharmaceutical composition comprising:
(a) a safe and effective amount of a compound of claim 12; and
(b) a pharmaceutically-acceptable carrier.

30. A pharmaceutical composition comprising:
(a) a safe and effective amount of a compound of claim 16; and
(b) a pharmaceutically-acceptable carrier.

31. A pharmaceutical composition comprising:
(a) a safe and effective amount of a compound of claim 26; and
(b) a pharmaceutically-acceptable carrier.

32. A method for treating a disease associated with unwanted metalloprotease activity, in a mammalian subject, the method comprising administering to said subject a safe and effective amount of a compound of claim 1.

33. A method for treating a disease associated with unwanted metalloprotease activity in a mammalian subject, the method comprising administering to said subject a safe and effective amount of a compound of claim 3.

34. A method for treating a disease associated with unwanted metalloprotease activity in a human or other animal subject, the method comprising administering to said subject a safe and effective amount of a compound of claim 16.

35. A method for treating a disease associated with unwanted metalloprotease activity in a mammalian subject, the method comprising administering to said subject a safe and effective amount of a compound of claim 26.

36. A method for treating a disorder modulated by metalloproteases, wherein the disorder is chosen from the group consisting of arthritis, cancer, cardiovascular disorders, skin disorders, ocular disorders, inflammation and gum disease, by administering to a mammal in need of such treatment a safe and effective amount of a metalloprotease inhibitor according to claim 1.

37. The method for treating a disorder according to claim 36, wherein the disorder is arthritis, and is chosen from the group consisting of osteoarthritis and rheumatoid arthritis.

38. The method for the treating a disorder according to claim 36, wherein the disorder is a cardiovascular disorder chosen from the group consisting of dilated cardiomyopathy, congestive heart failure, atherosclerosis, plaque rupture, reperfusion injury, ischemia, chronic obstructive pulmonary disease, angioplasty restenosis, and aortic aneurysm.

39. The method for the treating a disorder according to claim 36, wherein the disorder is an ocular disorder, and is chosen from the group consisting of corneal ulceration, lack of corneal healing, macular degeneration, retinopathy, and pterygium.

40. The method for treating a disorder according to claim 36, wherein the disorder is gum disease, and is chosen from the group consisting of periodontal disease and gingivitis.

41. The method for treating a disorder, according to claim 36, wherein the disorder is skin a disorder chosen from the group consisting of wrinkle repair and prevention, U.V. skin damage, epidermolysis bullosa, psoriasis, sclerodema, atopic dermatitis, and scarring.

42. The method for preventing the loosening of prosthetic devices chosen from the group consisting of joint replacements and dental prosthesis by administering to a mammal in need of such treatment, a safe and effective amount of a metalloprotease inhibitor according to claim 1.

43. A method for treating inflammatory conditions according to claim 36, wherein said inflammatory condition is chosen from the group consisting of inflammatory bowel disease, Crohn's Disease, ulcerative colitis, pancreatitis, diverticulitis, acne inflammation, bronchitis, arthritis, asthma.

44. A method of treating multiple sclerosis, comprising administering to a mammal in need of such treatment, a safe and effective amount of a metalloprotease inhibitor according to claim 1.

45. A method for treating musculoskeletal disease or cachexia comprising administering to a mammal in need of such treatment, a safe and effective amount of a metalloprotease inhibitor according to claim 1.

* * * * *

UNITED STATES PATENT AND TRADEMARK OFFICE
CERTIFICATE OF CORRECTION

PATENT NO. : 6,197,770 B1  Page 1 of 2
DATED : May 6, 2001
INVENTOR(S) : Michael George Natchus et al.

It is certified that error appears in the above-identified patent and that said Letters Patent is hereby corrected as shown below:

Column 37,
Table 1, Column W, Examples 16, 17 and 18, delete "-CH=CH-" and insert -- -CH=N- --.

Column 59,
Table 3, Column $R_2$, Example 57, delete: " 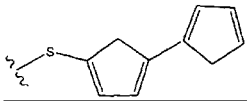 " and insert -- 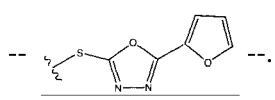 --.

Column 66,
Line 50, delete "4yl" and insert -- 4-yl --.

Column 67,
Line 56, delete "mixtures" and insert -- mixture --.

Column 70,
Line 19, delete "pent4" and insert -- pent-4 --.
Line 34, delete "4bromobenzenesulfonyl" and insert -- 4-bromobenzenesulfonyl --.

Column 77,
Line 6, delete "1" and insert -- [ --.

Column 89,
Line 47, delete "3".

Column 97,
Line 60, delete "-C(=O)$R^{21}$" and insert -- -C(O)$R^{21}$ --.

Column 101,
Line 11, delete "-C(=O)$R^{21}$" and insert -- -C(O)$R^{21}$ --.

UNITED STATES PATENT AND TRADEMARK OFFICE
CERTIFICATE OF CORRECTION

PATENT NO. : 6,197,770 B1
DATED : May 6, 2001
INVENTOR(S) : Michael George Natchus et al.

It is certified that error appears in the above-identified patent and that said Letters Patent is hereby corrected as shown below:

Column 102,
Line 42, delete "-C(=O)R$^{21}$" and insert -- -C(O)R$^{21}$ --.

Column 105,
Line 20, delete "-C(=O)R$^{21}$" and insert -- -C(O)R$^{21}$ --.

Signed and Sealed this

Seventeenth Day of August, 2004

JON W. DUDAS
*Acting Director of the United States Patent and Trademark Office*